US006310180B1

(12) United States Patent
Tam

(10) Patent No.: US 6,310,180 B1
(45) **Date of Patent: *Oct. 30, 2001**

(54) METHOD FOR SYNTHESIS OF PROTEINS

(75) Inventor: James P. Tam, Nashville, TN (US)

(73) Assignee: Vanderbilt University, Nashville, TN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/492,411

(22) Filed: Jun. 19, 1995

Related U.S. Application Data

(63) Continuation-in-part of application No. 08/490,932, filed on Jun. 16, 1995, now abandoned, which is a continuation-in-part of application No. 08/263,936, filed on Jun. 21, 1994, now abandoned, which is a continuation-in-part of application No. 08/081,412, filed on Jun. 21, 1993, now Pat. No. 5,589,356.

(51) Int. Cl.[7] .......................... A61K 38/00; A61K 38/04; C07K 1/00; C07K 14/00

(52) U.S. Cl. ........................... 530/339; 424/208.1; 435/4; 435/7.1; 436/518; 530/323; 530/324; 530/325; 530/326; 530/327; 530/328; 530/329; 530/330; 530/331; 530/334; 530/350; 530/387.1; 530/402; 530/403; 530/404

(58) Field of Search ............................. 424/208.1; 435/4, 435/7.1; 436/578; 530/323–331, 334, 339, 350, 387.1, 402–406, 341, 342

(56) References Cited

U.S. PATENT DOCUMENTS 5,589,356 * 12/1996 Tam .................................... 435/68.1

OTHER PUBLICATIONS

Dawson et al. Science, vol. 266, pp. 776–779, Nov. 1994.*

Kemp et al: J. Org. Chem., 1993, vol. 58, pp 2216–2222.*

Schnolzer et al: Science, 1992, vol. 256, pp 221–225.*

Kwiatkowski et al: Tetrahedron Lett., 1990, vol. 31, pp 2093–2096.*

Kemp et al: J. Org. Chem., 1989, vol. 54–1589–1603.*

* cited by examiner

*Primary Examiner*—Jyothsna Venkat
*Assistant Examiner*—Maurie E. Garcia
(74) *Attorney, Agent, or Firm*—Klauber & Jackson

(57) ABSTRACT

A method for peptide synthesis is disclosed that requires neither protecting groups nor activation of the C-α carboxyl groups. The method comprises ligating a first molecule to a second molecule by promoting the orthogonal coupling of the molecules to each other. In an aspect of this method, an acyl-type reaction occurs between the molecules. The method contemplates the joining of molecules of variant size to each other, as well as the coupling of multiple identical molecules. The invention also covers the ligation of unprotected peptide, proteins or nonpeptide segments to prepare therapeutic products and synthetic vaccines with linear, circularized, or branched backbone structures, as well as the site-specific modification of peptides or proteins by lipidation and pegylation.

13 Claims, 37 Drawing Sheets

| | X | Y | Z | R |
|---|---|---|---|---|
| thioester exchange | SR | - | S | H |
| mixed disulfide capture | $SSR_1$ | - | SS | H |
| thioesterification | - | Br, Tos | S | H |
| mixed disulfide capture | - | $SSR_2$ | SS | H |
| aldehyde capture | $OCH_2CHO$ | - | Thz | |

| | X | Y | Z | R |
|---|---|---|---|---|
| thioester exchange | SR | - | S | H |
| mixed disulfide capture | $SSR_1$ | - | SS | H |
| thioesterification | - | Br, Tos | S | H |
| mixed disulfide capture | - | $SSR_2$ | SS | H |
| aldehyde capture | $OCH_2CHO$ | - | Thz | |

IIa IIb IIc IId IIe

Scheme II.

i. DMF, 60-70° C, 24 h; ii. 30% TFA in $CH_2$ $Cl_2$ (2-5% $H_2O$); iii. $H_2O/CH_3CN$, pH2-5; iv. pH6-9.

IIIa IIIb IIIc

Scheme III. Mechanism of the acyl transfer reaction.

Scheme IV. Synthesis of a pentadecapeptide.

I (Peptide-Oxm-Map)

II (Peptide-Hdz-MAP)

III (Peptide-Thz-MAP)

1

2

3

4

MALDI-MS OF FIV9-Oxm-MAP

MALDI-MS OF FIV9- Hyz-MAP

MALDI-MS OF FIV9- Thz-MAP

FIG. 19
Reaction Scheme and Thiclaclones
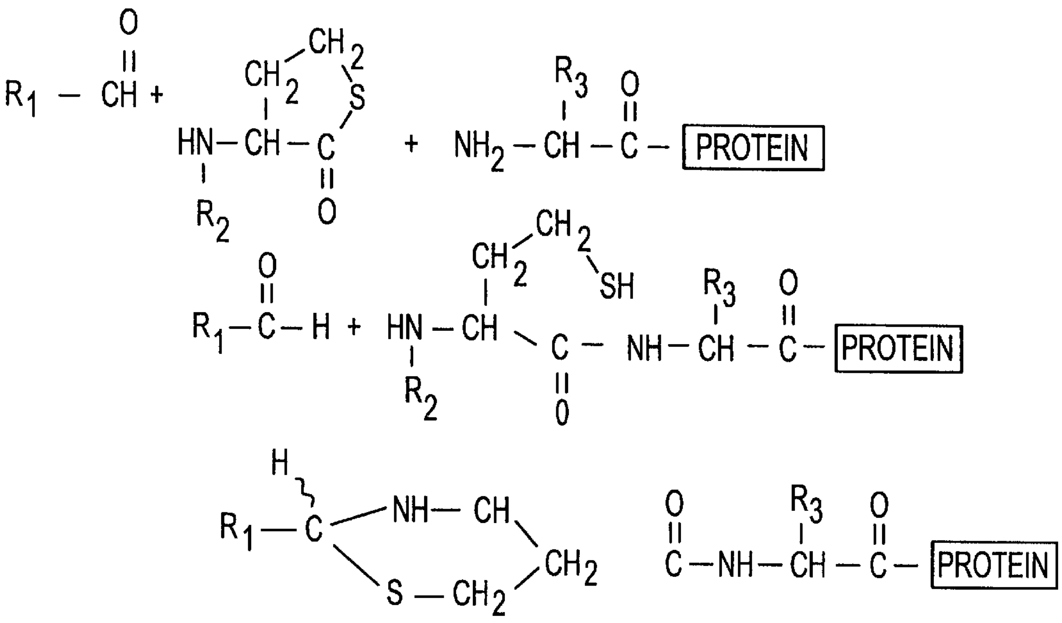
Substituted Thiolactone
1 —
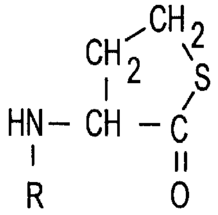
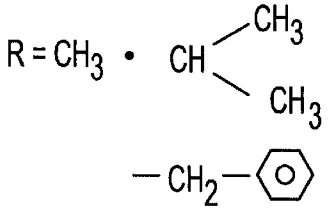
2 —
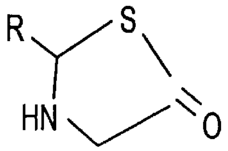
3 —
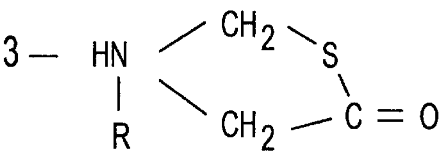

FIG. 20
A General Scheme for Site-specific Modification of Peptides and Proteins
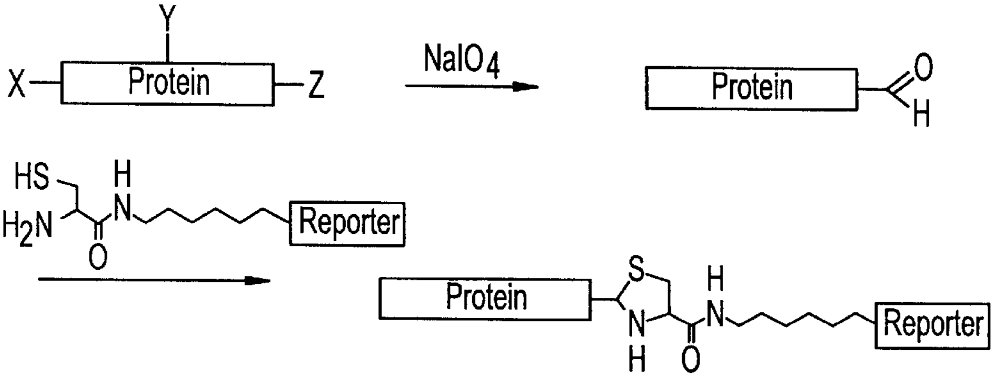
X,Y,Z Precursor carbonyl sites: X = Ser or Thr, Y = oligosaccharide, Z = δ-hydroxy-lysine
Design of the Capture Ligand Containing a Reporter Group (Biotin) and a Capture Moiety (1, 2-Aminothiol or Aldehyde)
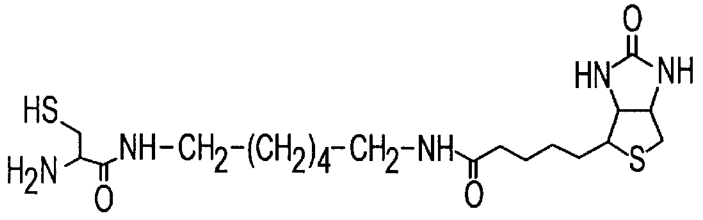
Capure site Spacer Reporter group Preparation of Biotion $-C_6$ -Cys(BCC) for site-specific Biotinylation

FIG. 22

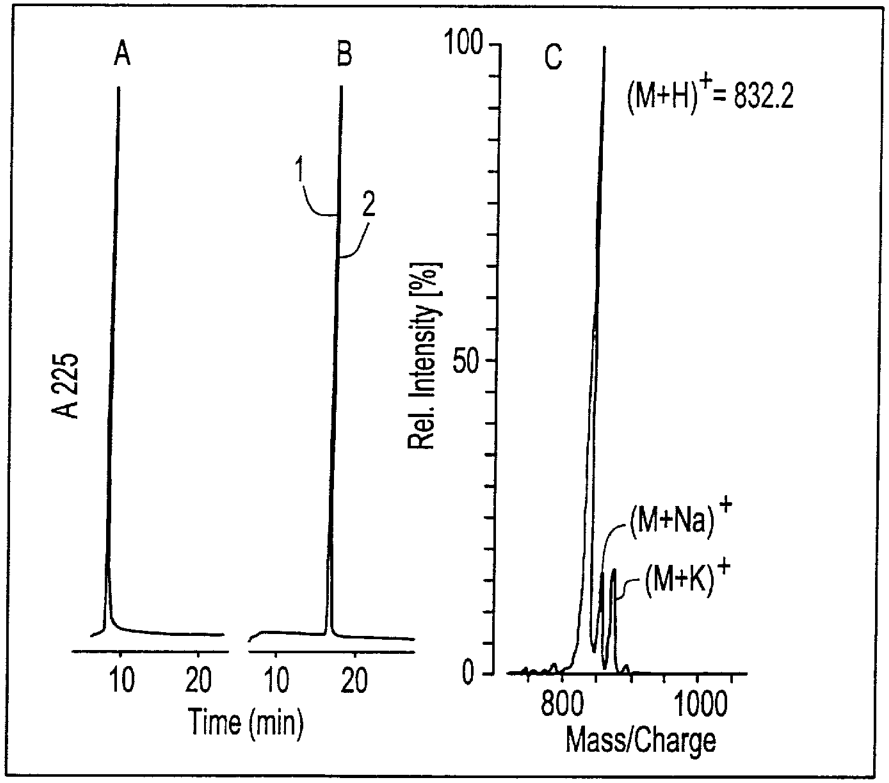

Pilot biotinylation of glyoxylyl-MKA analyzed by RP-HPLC and MALDI-MS. Panel A: glyoxylyl-MKA. Panel B: diastereomers (1, 2) of biotinylated MKA. Panel C: MALDI-MS shows the expected molecular mass, 832.2 ($M + H^+$). HPLC condition: Column, 250 x 4.6 mm i.d. (5μ, Vydac 218TP54). Flow rate: 1 ml/min. Buffer A, 0.046% TFA in water; Buffer B, 0.039% TFA in 60% ACN. Gradient: 0-1 min 10% B, isocratic: 1-31 min, linear gradient from 10% to 100% B. Detection: 225 nm.

RP-HPLC monitored progress of biotinylation of SSQFQIHGPR after 3h (A), 6h (B) and 9h (C). 1: BCC, 2: α-glyoxylyl-SQFQIHGPR, 3:Biotin-$C_6$-Thz-SQFQIHGPR.

RP-HPLC analysis of α-N-glyoxylyl-PTH (1-34, human) (A) and biotinylated PTH (B) and MALDI-MS of bitinylated PTH.

Detection of biotinylated $\alpha_1$-acid glycoprotein. 1 to 150 ng of $\alpha_1$-acid glycoprotein was biotinylated after oxidation for 30 min at 4°C with 10 mM $NaIO_4$ and incubation with 50 fold excess of BCC overnight. Triplicate samples were then subjected to ELISA and stained with an avidin-peroxidase conjugate.

1

2

3

METHOD FOR SYNTHESIS OF PROTEINS

CROSS REFERENCE TO RELATED APPLICATIONS

The present application is a Continuation-In-Part of application Ser. No. 08/490,932 filed Jun. 16, 1995 now abandoned, which is in turn, a Continuation-In-Part of application Ser. No. 08/263,936 filed Jun. 21, 1994, now abandoned which is in turn, a Continuation-In-Part of application Ser. No. 08/081,412, filed Jun. 21, 1993 now U.S. Pat. No. 5,589,356. Applicant claims the benefits under 35 USC 120, as to all prior applications.

This invention was made with government support under grant number A128701 from the National Institutes of Health (NIH). The United States government may have certain rights in the invention.

BACKGROUND OF THE INVENTION

The present invention relates generally to methods for the synthetic preparation of peptides, and more particularly to the preparation of peptides of improved activity and complex structure, and to the products, including bioactive agents, pharmaceutical compositions and vaccines, that may embody such constructs.

The synthesis of peptides or proteins has become highly efficient with the advances of the solid-phase peptide synthesis and recombinant DNA technology. Solid-phase peptide synthesis with the aid of automation and other mechanical devices can quickly produce a peptide of greater than 100 amino acids or a library of hundreds of short peptides. Likewise, recombinant DNA technology with an optimal expression system can produce proteins accurately and in large quantity. The development of a method of chemical ligation of peptide segments would be desirable, as it would incorporate both the efficiency of the solid-phase method to generate specific segments, and the availability of proteins generated by the recombinant method. The combination of the two types of production of peptide segments would enable engineered proteins to contain unusual structures or nongenetic encoded amino acids by a specific ligation method.

A strong impediment to the development of such an approach has been a lack of an efficient method for their synthesis. In particular, there is no effective chemical method to selectively couple two unprotected peptide segments to form an amide bond. In general, protecting groups are necessarily attached to nontarget functional groups on the first peptide segment prior to activation of the C-α of the carboxylic group by a coupling reagent and the consequent peptide bond formation with the N-α of the amino group of the second protected peptide segment. As a result, the development of various protecting group schemes has been the key for the conventional approach of ligating peptide segments.

However, the use of protected peptide segments is incompatible with the overall scheme of engineering proteins using proteins produced by means of recombinant DNA technology as a source. Such technique is also limited as it is labor-intensive and unpredictable, partly due to the solubility and coupling difficulties of protected peptide segments. Often, large protected peptide segments are minimally soluble in even the most powerful polar aprotic solvents such as dimethylsulfoxide (DMSO) and dimethylformamide (DMF).

The problem of the insolubility of protected peptide segments has been addressed with limited success in several ways, including the use of (1) a partial protecting group strategy which masks all side chains except those of Ser, Thr, and Tyr, and (2) a minimal protecting group strategy which masks only thiol and amino side chains. Protecting groups used in all these approaches alter peptide conformations. This creates a difficult problem in the synthesis of large peptides, since folding and renaturation are required after the completion of the synthesis and removal of the protecting groups. These limitations, coupled with the ease of obtaining proteins and protein domains through recombinant DNA technologies, have suggested the need to develop a new strategy for ligating unprotected peptides and proteins in order to engineer new proteins with unusual structures, architectures and functions.

Since protecting groups are the root of the problem, scientists have developed two ligation strategies in the past ten years which use unprotected segments. One of the methods requires the use of enzymes in the reverse proteolysis process in conjunction with a high content of water-miscible solvents. Although enzymatic synthesis has been successful with small peptides, enzymatic synthesis of large peptides has presented difficulties. The stringent criteria demanded by using high molar concentrations of peptide segments accompanied by rapid completion of the reverse proteolytic process without the attendant hydrolysis or transpeptidation have been prohibitive obstacles in the enzymatic synthesis of large peptides. Nevertheless, the use of enzymes in coupling unprotected peptide segments eliminates the necessity of activating the carboxylic group involved in the coupling reaction of the peptide segments. Furthermore, it also provides the ability to perform the reaction in an aqueous environment.

Another strategy uses a tricyclic aromatic template containing an aryl alcohol and a thiol to form an active ester with the carboxyl segment and a disulfide with the amino segment, respectively, in order to bring two unprotected peptide segments in close proximity with each other. Such positioning of the peptide segments enables them to undergo an O to N-acyl transfer reaction (Fotouhi, N. et al., 1989; Kemp, D. S. et al., 1991).

A problem with the currently accepted methods of protein synthesis which include both conventional liquid state and solid state peptide syntheses is that their application is limited to small straight chain peptide segments, whereas the need exists for such a method of synthesis to be available for long straight chain peptides, branched straight chain pep tides and circular peptides.

From the foregoing, it is apparent that a need exists for the development of an efficient and reliable strategy for peptide synthesis that facilitates the preparation of peptides and proteins without limitation as to their size and structural complexity, that results in the formation of stable and desirably active molecules. It is toward the fulfillment of this need that the present invention is directed.

SUMMARY OF THE INVENTION

In its broadest aspect, the present invention relates to a method for ligating a first molecule to a second molecule by promoting the orthogonal coupling of the molecules to each other. The method so stated may include within its mechanism of action, the occurrence of an acyl transfer-type reaction between the first and second molecules. More particularly, the invention extends to a method for ligating the carboxylic acid group of a first molecule with the amino group of a second molecule through an amide bond, wherein the functional groups of said first and second molecules are either minimally protected, partially protected, globally protected or not protected at all, which comprises promoting the orthogonal coupling of said first molecule to said second molecule.

Yet further, the present invention relates to methods for ligating peptide segments chemically without using protecting groups. A major handicap in developing a ligation method using unprotected peptides is that the carboxyl moiety cannot be activated in any form, even as a weak active ester, in the presence of unprotected side chain amines and other nucleophiles. However, if the N-α and C-α peptide segments can be brought close together, their proximity may enable peptide bond formation through an O to N-acyl rearrangement. The orthogonal coupling strategy of the present invention takes advantage of the O to N-acyl rearrangement reaction.

The coupling method of the instant invention does not require protecting groups or activation of the carboxyl component in the conventional sense.

This coupling strategy can be applied to circular proteins as well as branched straight-chain proteins. The former proteins are called circular rather than cyclic because they are connected end to end by a peptide bond while cyclization comprises nonspecific circularization. Circular proteins are difficult synthetic targets because several of them contain three disulfide bonds. In addition, they have potential therapeutic value, and circularization may improve their half life in vivo and increase their stability against proteolytic degradation, particularly by exopeptidases. Unlike cyclic peptides, synthetic circularized proteins are rare because they are not easily susceptible to synthetic methods presently available. One example of a circular protein is BPTI (bovine pancreatic trypsin inhibitor) which uses non-specific carbodiimide for its circularization.

The orthogonal coupling strategy can also be used in the construction of protein dendrimers and in the site-specific modification of proteins. Specially constructed dendrimers may form the basis for the assembly of effective vaccine modalities, including, for example, a multiple antigen peptide construction. Likewise, the invention extends to the ligation of peptide segments to materials comprising, but not limited to, DNA. Ligating proteins or peptides to DNA can be useful in biological studies.

In a particular embodiment, the method proceeds by means of incorporating a masked α-aldehyde ester on a carboxylic group and activating that group by releasing the aldehyde thus allowing the carboxylic group to interact with an amino group to form an amide bond. Other strategies such as thioesterification, disulfide exchange, as well as N-acylation and O-acylation, each involving suitable variant reactants, are likewise contemplated and included herein as set forth hereinafter.

The present method provides a specific and stable conjugation for peptide/protein antigen to a carrier, drug to a protein, reporter group to an antibody or enzyme, and many others.

Accordingly, it is a principal object of the present invention to provide a method for the facile preparation of peptides and proteins, that may be performed without the use of protecting groups associated with the peptide reactants.

It is a further object of the present invention to provide a method as aforesaid, that yields stable products even having complex conformations and structures.

It is still further object of the present invention to provide a method of ligation of two peptide segments from the group comprising, but not limited to, long straight chain peptides, branched chain peptides and circular peptides, without protecting the various functional groups and without activating the carboxyl group of a first peptide segment which will form a peptide bond with the amino group of a second peptide segment.

It is a still further object of the present invention to provide a method as aforesaid by which circular proteins may be readily prepared and thereby available for biochemical, biophysical, and therapeutic uses.

Yet a further object of the invention is to prepare branched proteins such as dendrimers by the present method, by linking multiple copies of unprotected peptides or proteins to a scaffold or template by an amide.

Furthermore, it is an object of this invention to provide a high effective molarity for peptide bond formation through the efficient O to N-acyl transfer reaction.

It is an additional object of this invention to provide a versatile means of enzymatic coupling to activate a carboxylic group.

It is also an object of this invention that the reactions required in this method may be run in one vessel in aqueous solution, require only pH changes, no intermediate purification steps and no harsh final deprotection, renaturation or disulfide bond formation.

Finally, it is an object of this invention to provide a means for the site-specific modification of a protein with a peptide, protein, or non-protein molecule such as a lipid or polyethylene glycol.

Other objects and advantages will become apparent to those skilled in the art from a consideration of the ensuing description taken in conjunction with the following illustrative drawings.

A. Reaction at pH 9: a. t=22 minutes; b. t=155 minutes; c. t=284 minutes; d. t=540 minutes B. Reaction at pH 6: a. t=2.5 h; b. t=11 h; c. t=26 h; d. t=61 h; Peaks 1,2,3 and 4 correspond to compounds IId1, Z-Ala-OH, IIe1, IIc1.

Figure 6:
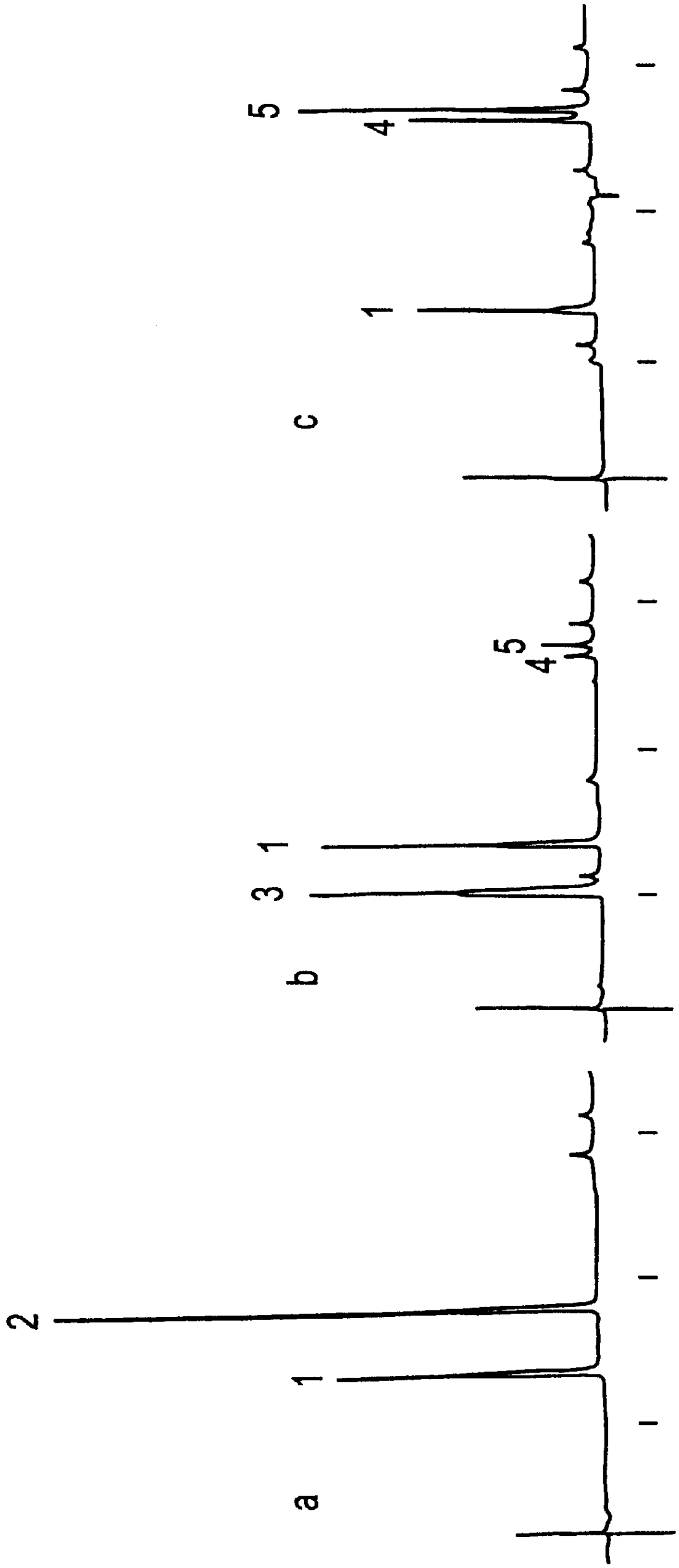

FIG. 6 is an HPLC profile for the segment synthesis of the model pentadecapeptide:

a. before TFA deprotection;

b. after TFA deprotection and upon redissolution in acetate buffer (pH 4);

c. ring formation product after 3 hours reaction;

d. purified ring product before rearrangement;

e. 20 hours at pH 5; and f. after 2 days at pH 5.

Figure 7:
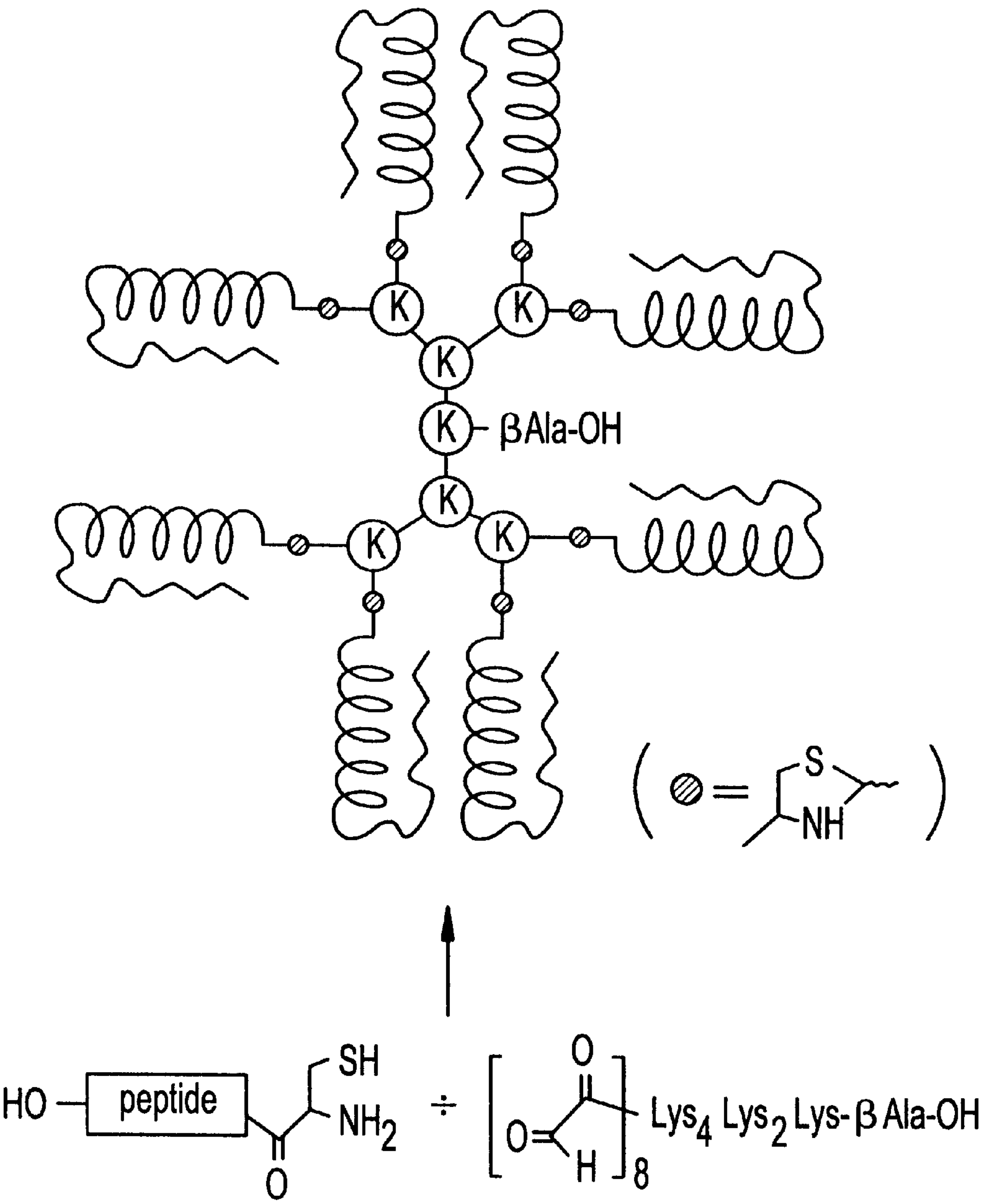

FIG. 7 is a schematic representation of a peptide dendrimer containing eight peptidyl branches anchored on a scaffolding of oligolysine (indicated by circled K) via a thiazolidine linkage (solid circles) which is obtained by reacting the N-terminal cysteine with a glyoxylyl scaffolding.

Figure 8:
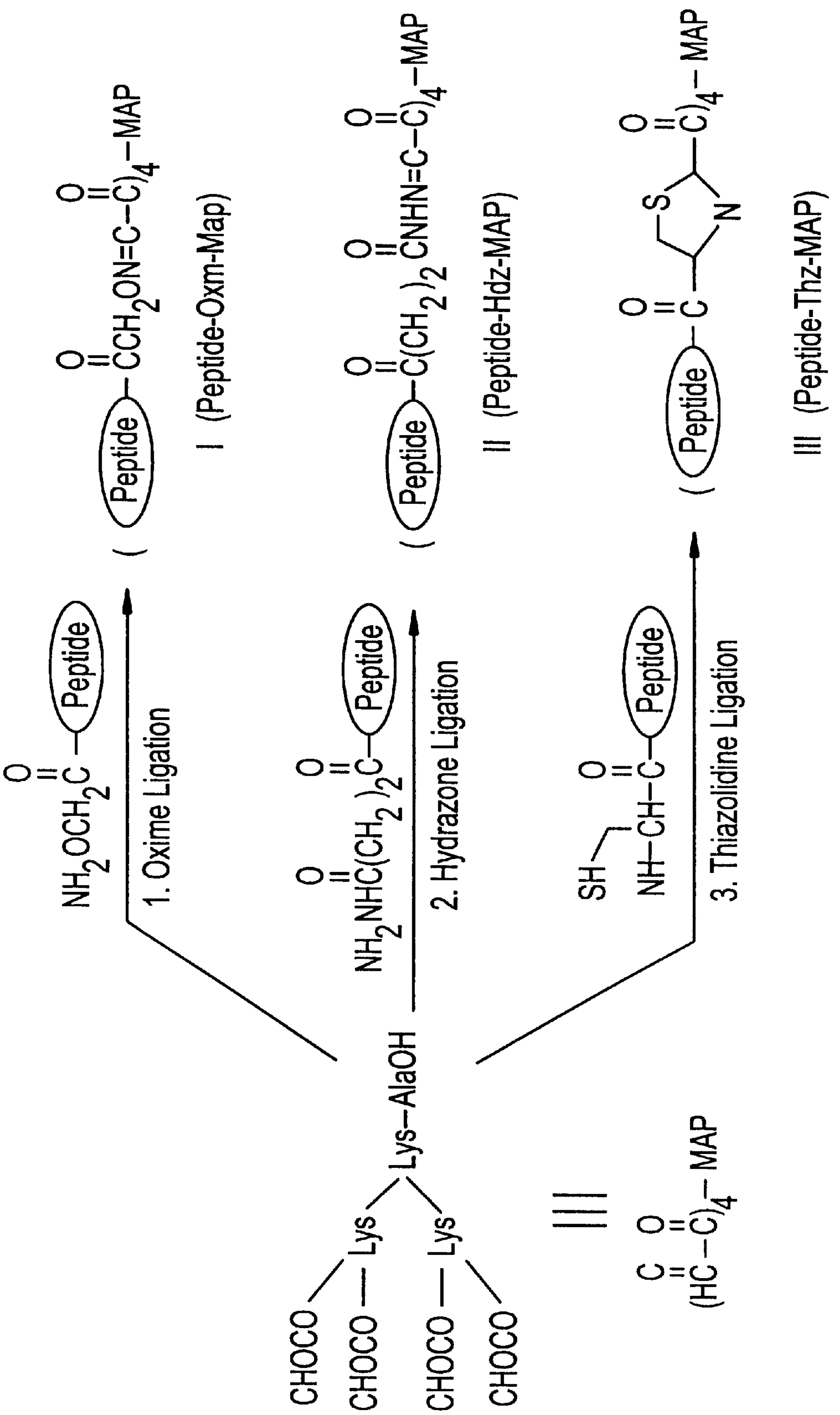

FIG. 8 is synthesis of MAPs with formation of 1): oxime-, 2): hydrazone-, and 3): thiazolidine- linkage. Peptide sequence: VA20=VMEYKARRKRAAIHVMLALA (SEQ ID NO:8). Reaction product: I): VA20-Oxm-MAP; II): VA20-Hdz-MAP; III): VA20-Thz-MAP.

Figure 9:
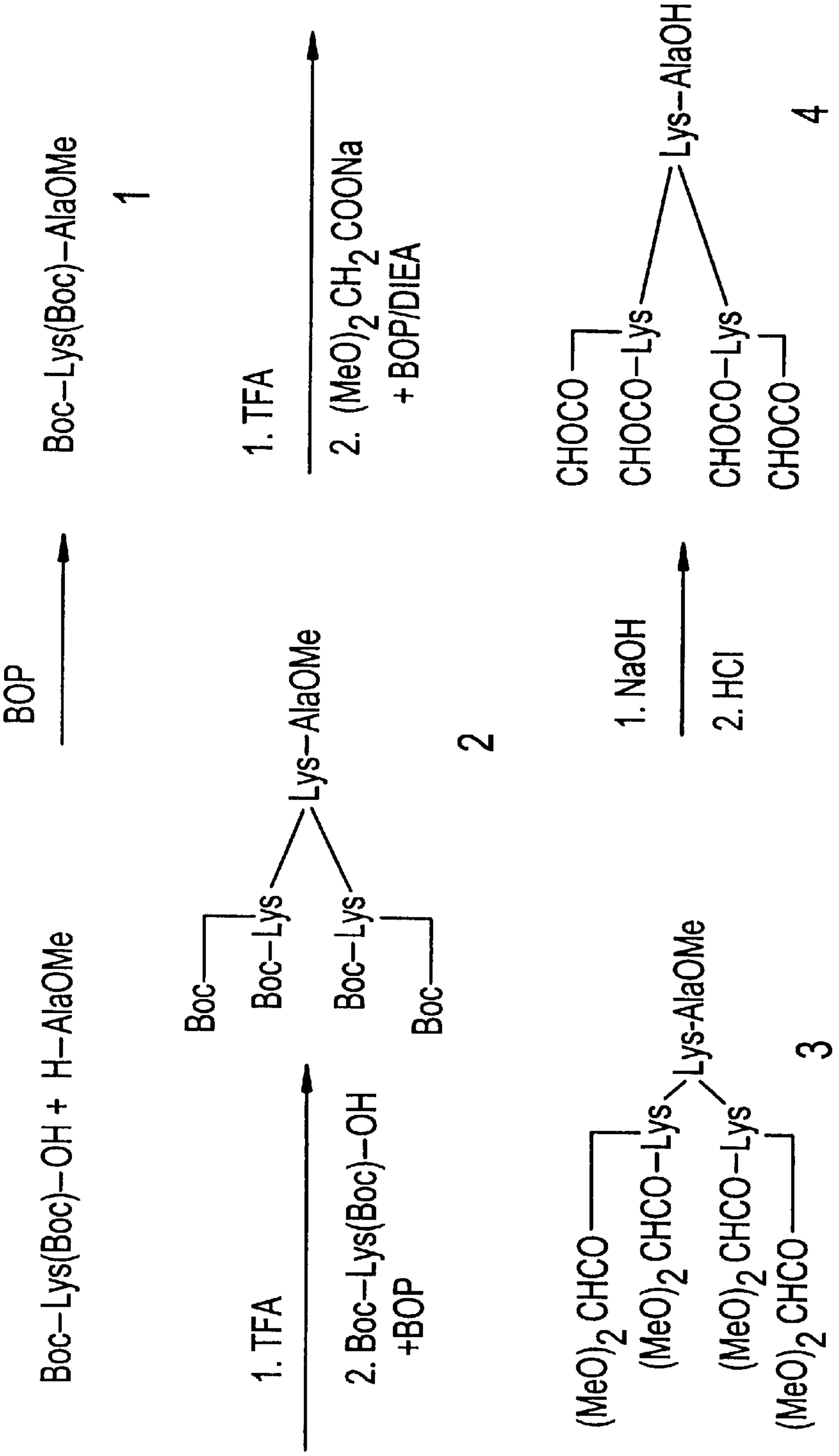

FIG. 9 is a scheme for preparation of glyoxylyl-MAP core matrix.

Figure 10:
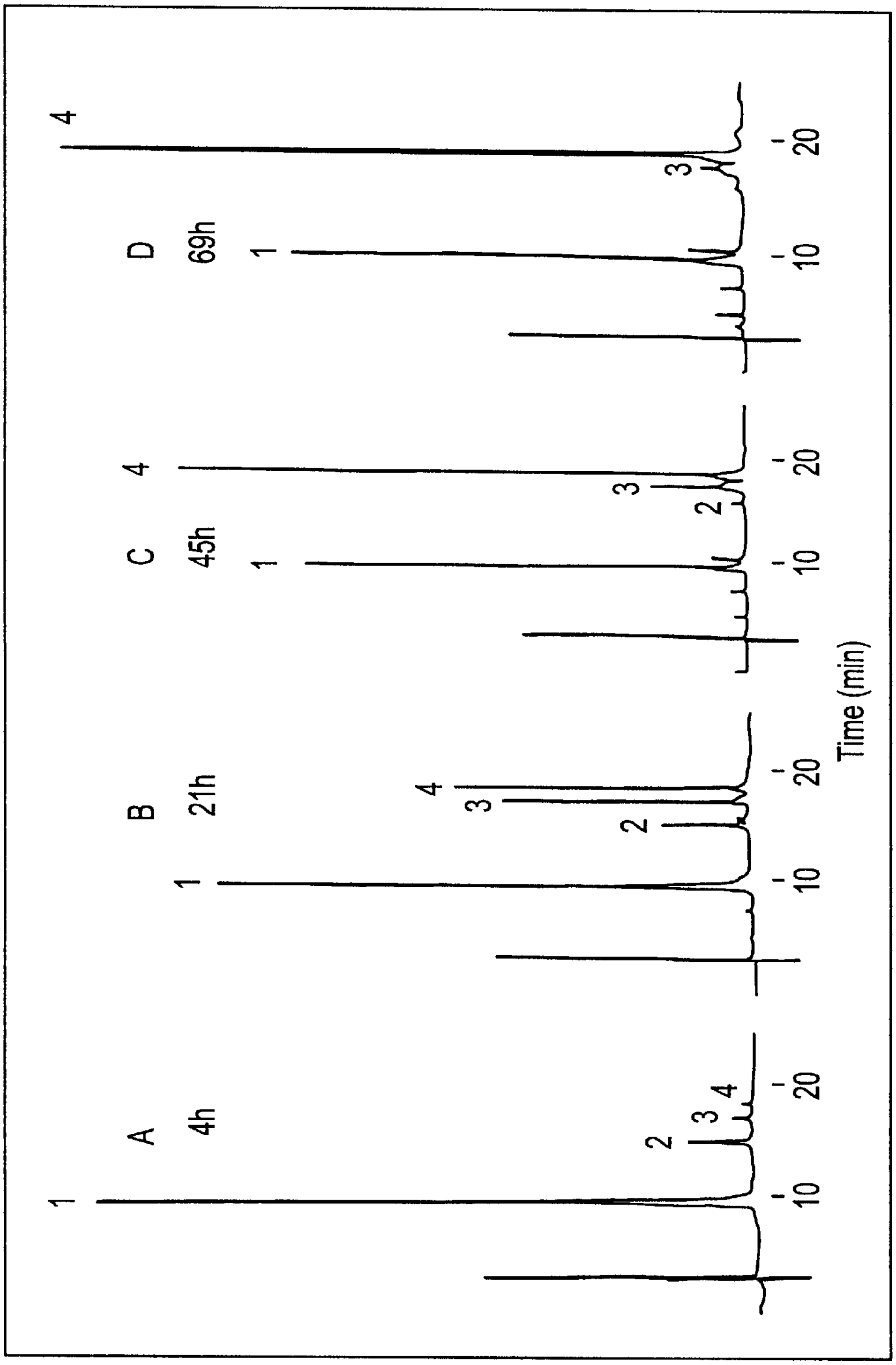

FIG. 10 is RP-HPLC analysis of oxime reactions between unprotected peptide and glyoxylyl-MAP [$(CHOCO)_4$-MAP]. Unprotected peptide was marked as 1. MAP cores linked with two, three, or four copies of peptide were labeled as 2, 3, or 4, respectively. HPLC conditions are described in the experimental section.

Figure 11:
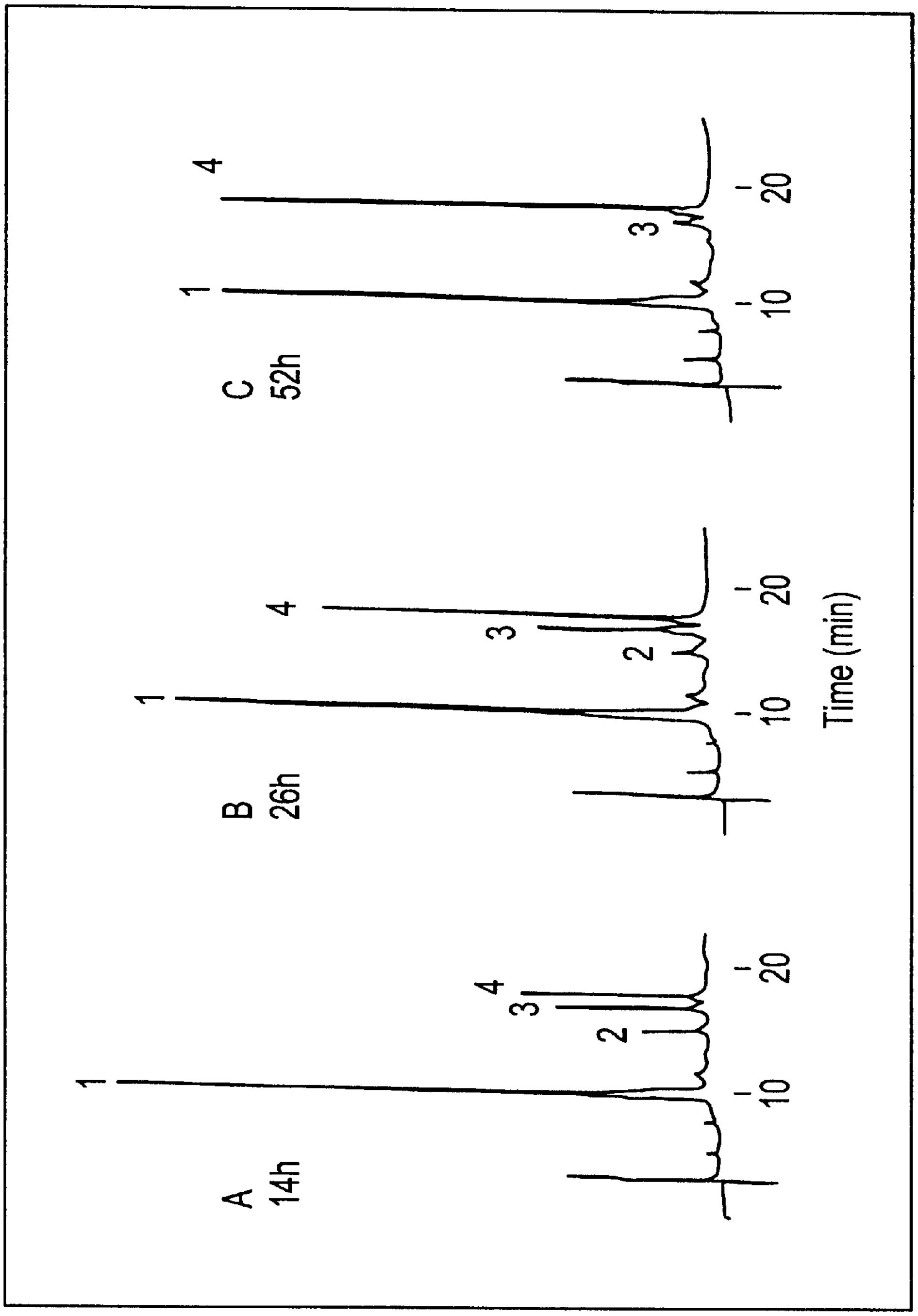

FIG. 11 is RP-HPLC analysis of hydrazone reactions between unprotected peptide and glyoxylyl-MAP [$(CHOCO)_4$-MAP]. Unprotected peptide derivative was marked as 1. MAP cores liked with two, three, or four copies of peptide were labeled as 2, 3 or 4, respectively. HPLC conditions are described in the experimental section.

Figure 12:
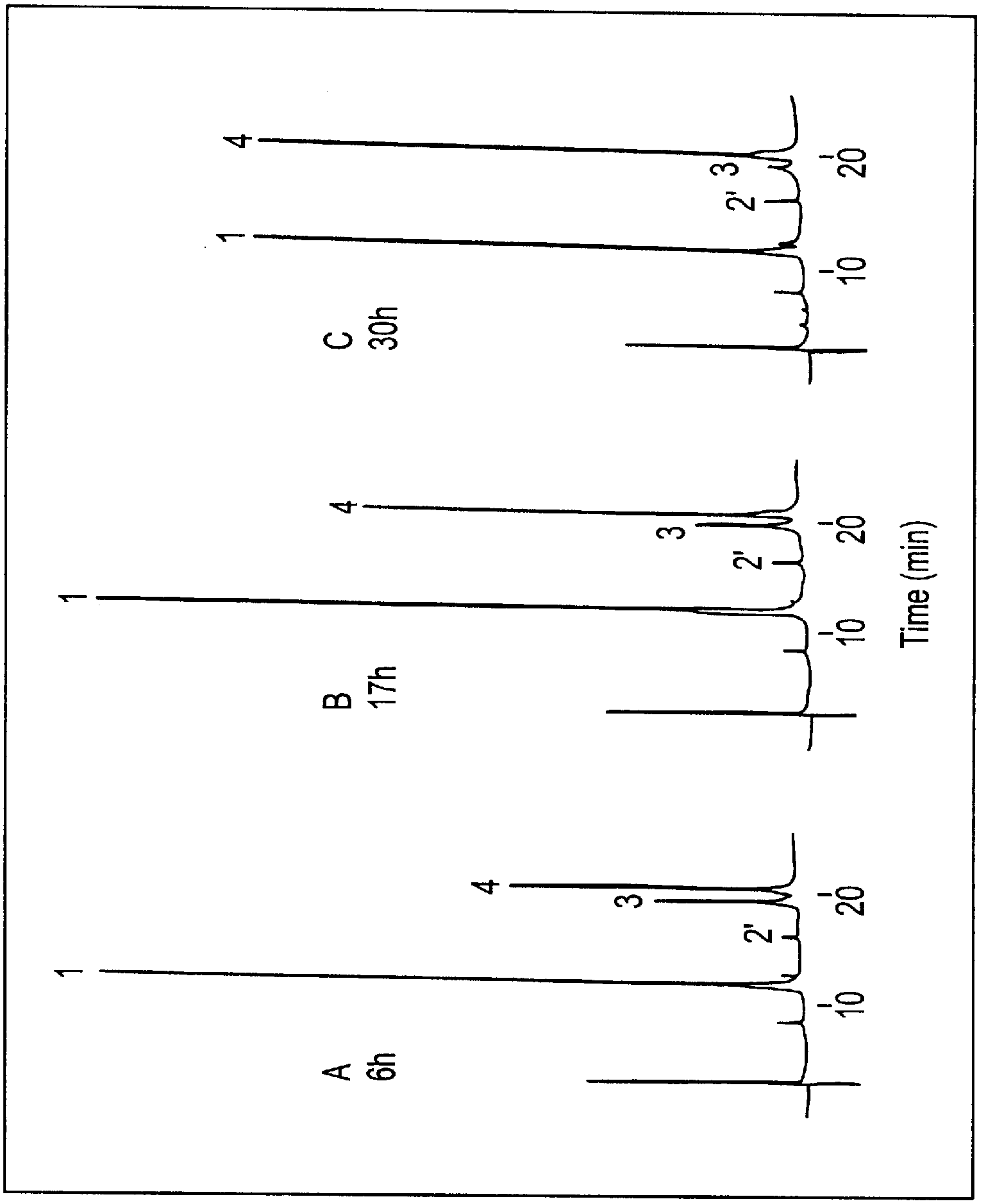

FIG. 12 is RP-HPLC analysis of thiazolidine reactions between unprotected peptide and glyoxylyl-MAP [$(CHOCO)_4$-MAP]. Unprotected peptide derivative was marked as 1. MAP cores linked with three or four copies of peptide were labeled as 2, or 4, respectively. The peak marked with 2' is the dimeric product of peptide derivative formed via disulfide bond. HPLC conditions are described in the experimental section.

Figure 13A:
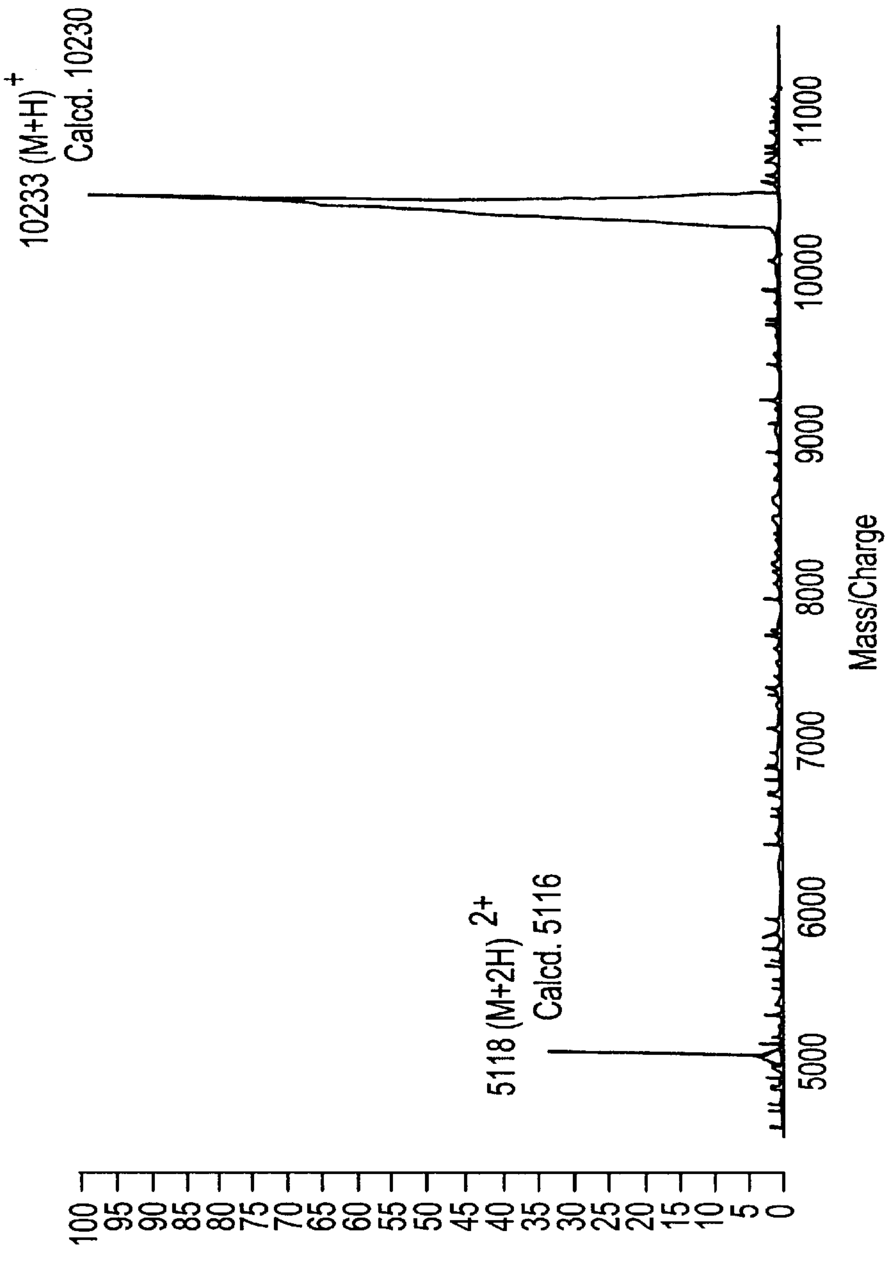
Figure 13B:
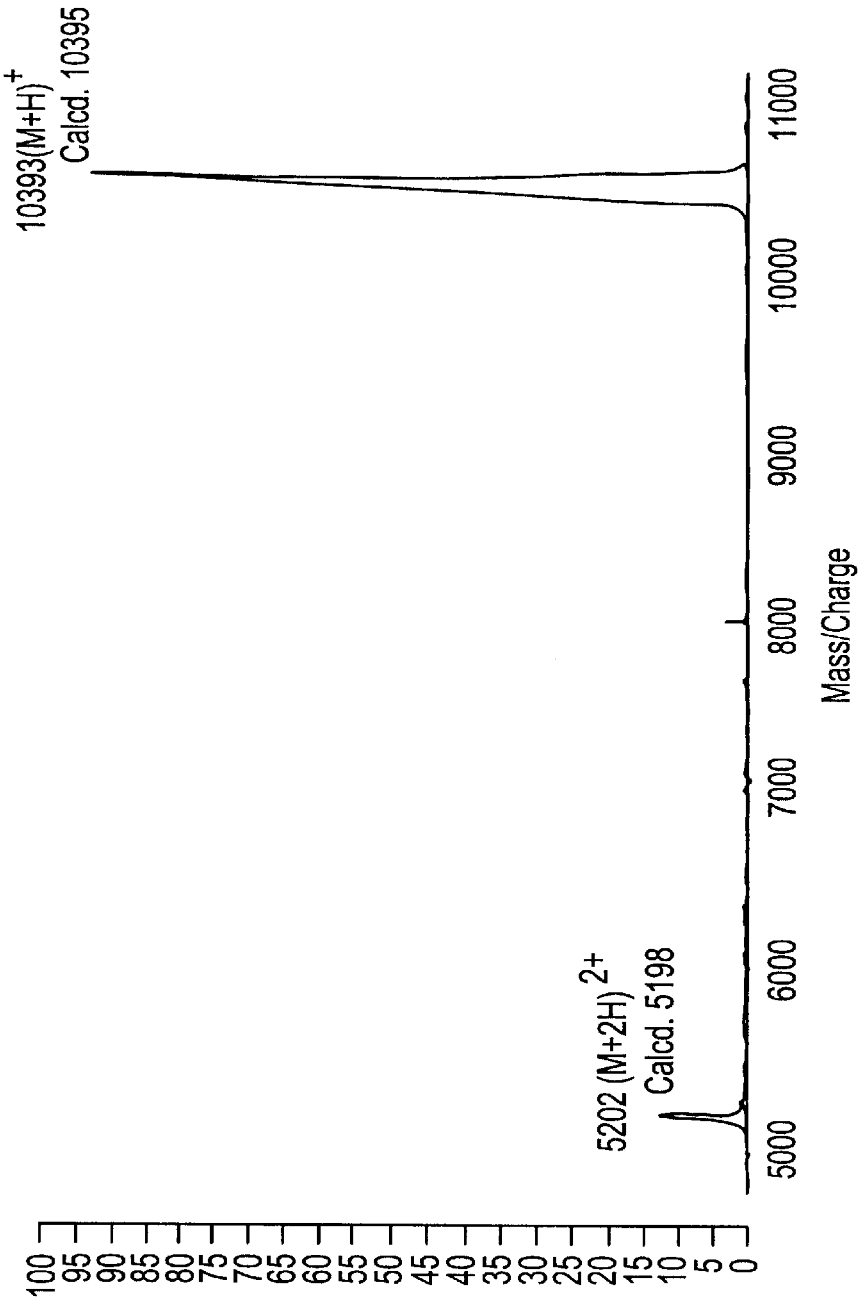
Figure 13C:
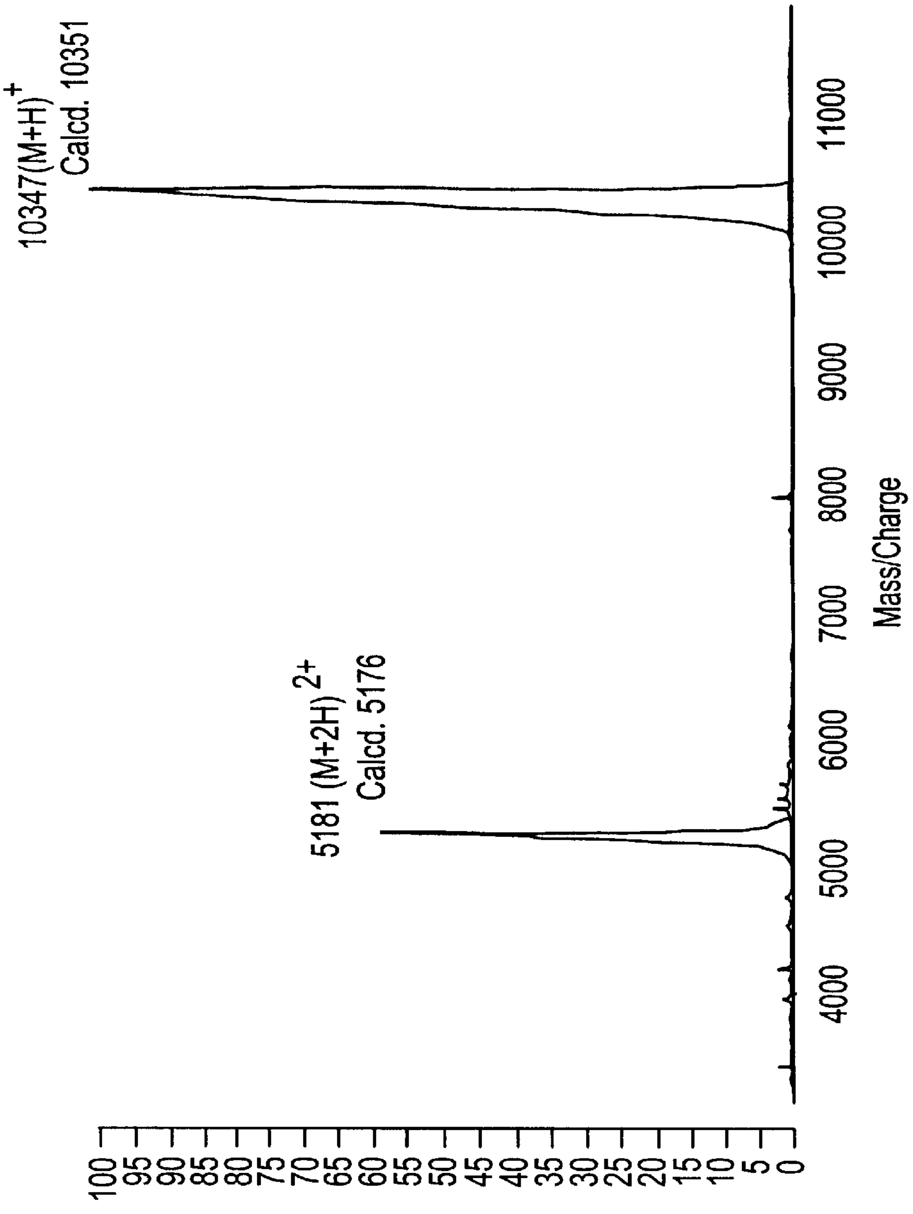

FIG. 13 a set of three tables comparing rates of MAP formation through oxine, hydrazone and thiazolidine.

Figure 14:
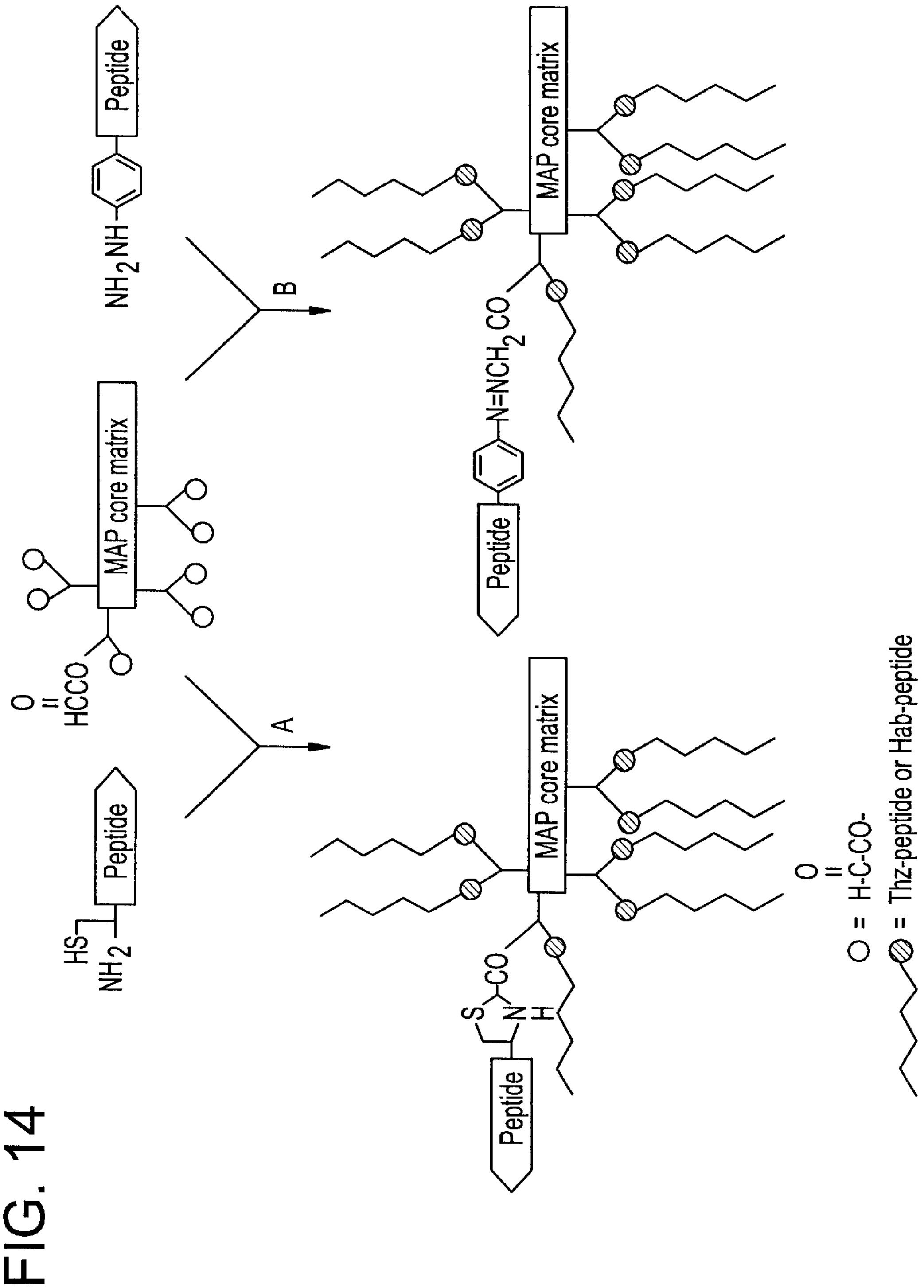

FIG. 14 is a general scheme depicting the chemistry of weak base-aldehyde for the ligation of unprotected peptide segments to a MAP core matrix containjng an p-oxoacyl group (A) thiazolidine ring formation between a peptide bearing N-terminal cysteine and (B) hydrazone formation between a peptide with N-terminal 4-hydrazino benzoyl group.

Figure 15:
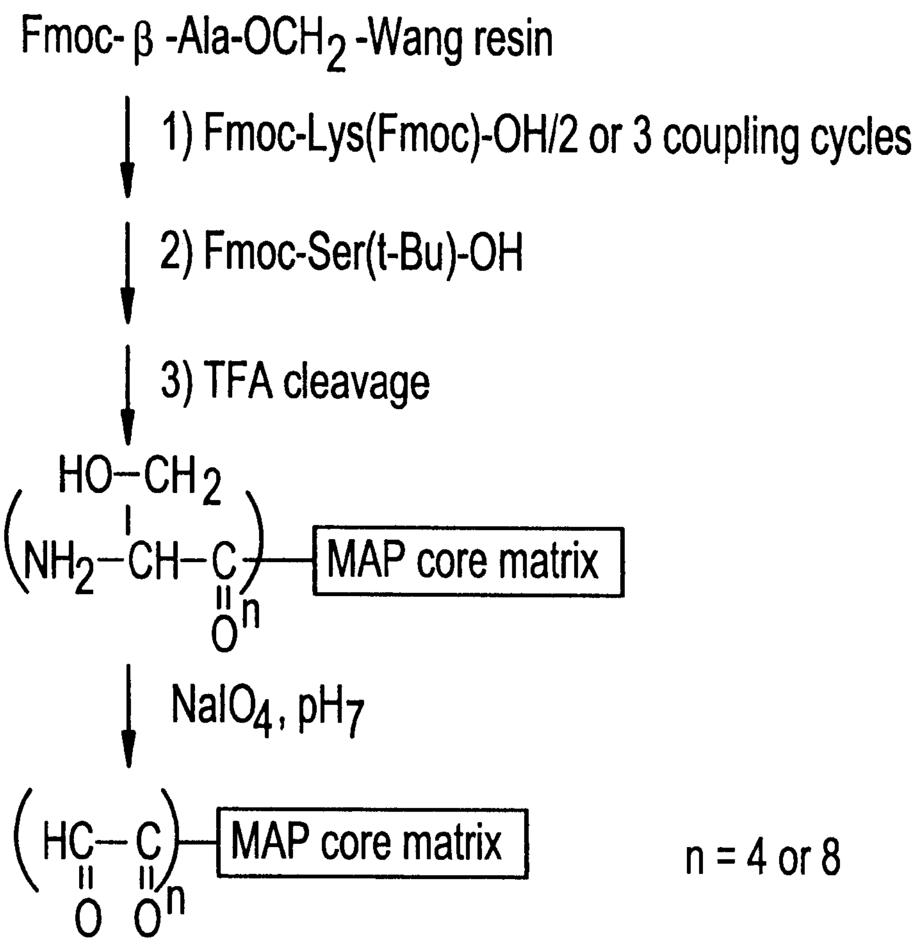

FIG. 15 is a synthetic scheme for the preparation of the α-oxoacyl-MAP core matrix.

Figure 16:
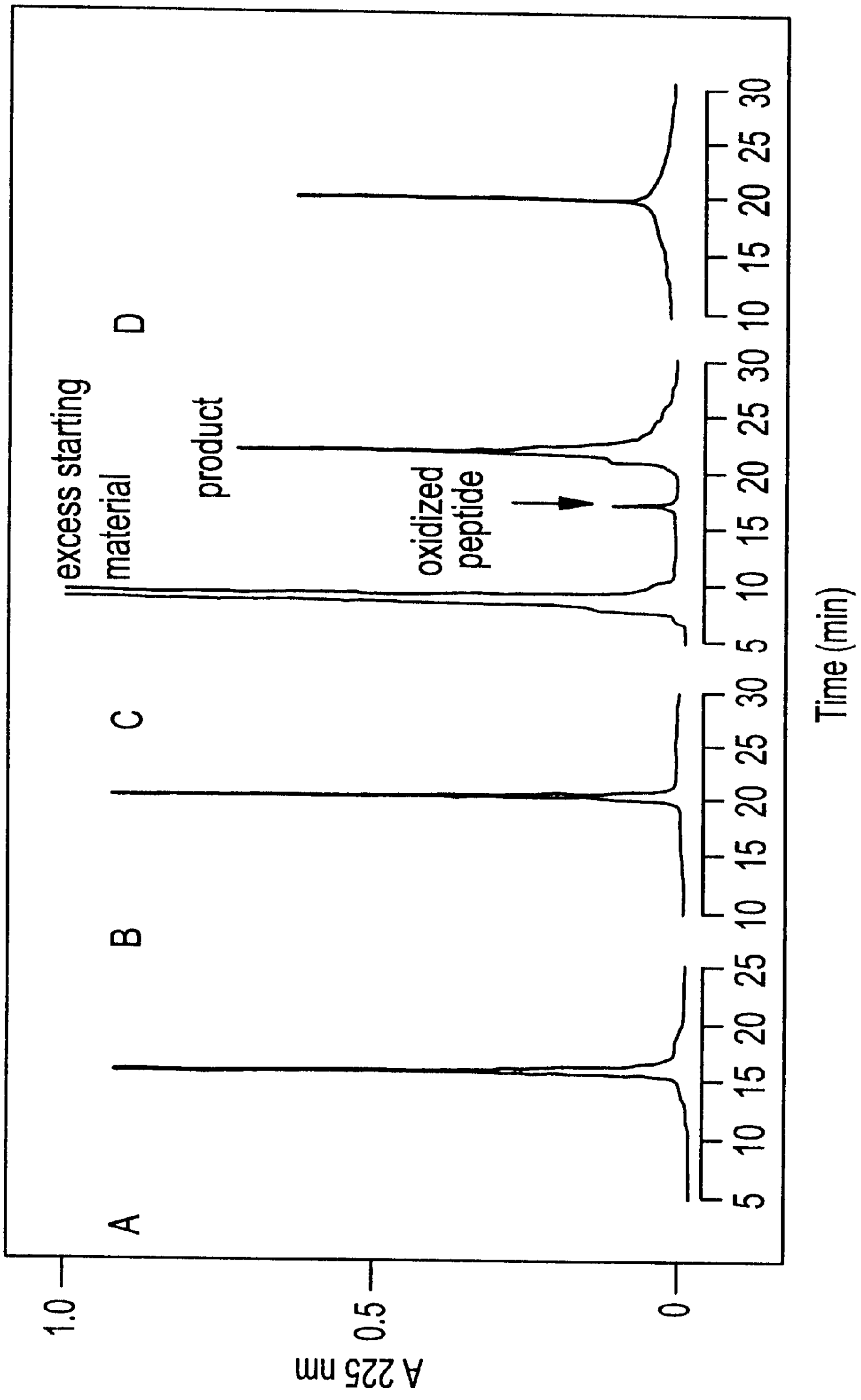

FIG. 16 is RP-HPLC profile of (A) purified $(CHOCO)_8$--$Lys_4$-$Lys_2$-Lys-βAla-OH using a C18column; (B) the purified starting material CA16 using a C18-column; (C) the crude conjugation reaction between $(CHOCO)_8$-$Lys_4$-$Lys_2$-Lys-βALA-OH and the peptide Ca-16 using a C8-column; and (D) incubated $(NA-15)_4$-Thz-MAP at 37° C., pH 7 after 110 hr using a C8-column to show the stability.

Figure 17:
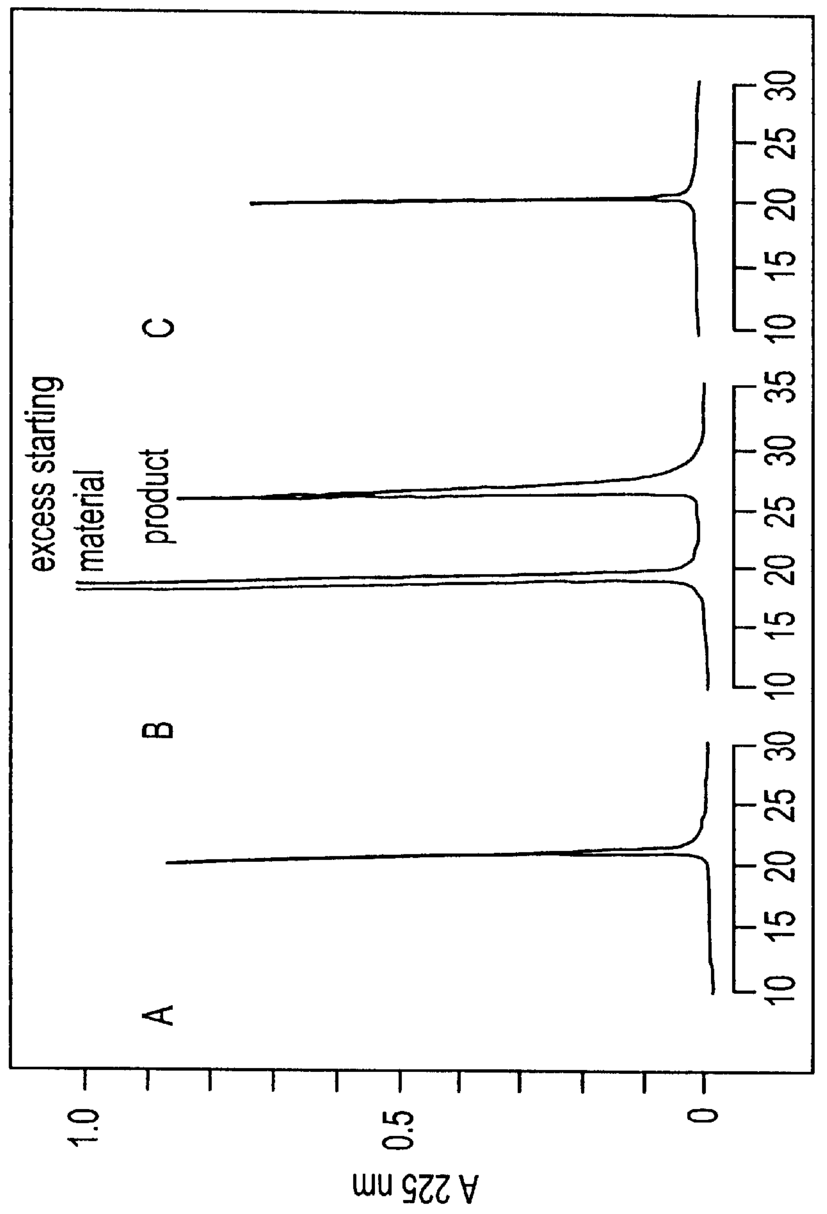

FIG. 17 is RP-HPLC profile of (A) the purified peptide Hob-SR10 using a C18 column; (B) the crude ligation reaction between $(CHOCO)_8$-$Lys_4$-$Lys_2$-Lys-βAla-OH and Hob-SR10 using a C8-column; and (C) incubated $(SR\text{-}10)_4$-Hab-MAP at 37 pC, pH 7.4 after 46.5 hr using a C4-column to show the stability.

Figure 18:
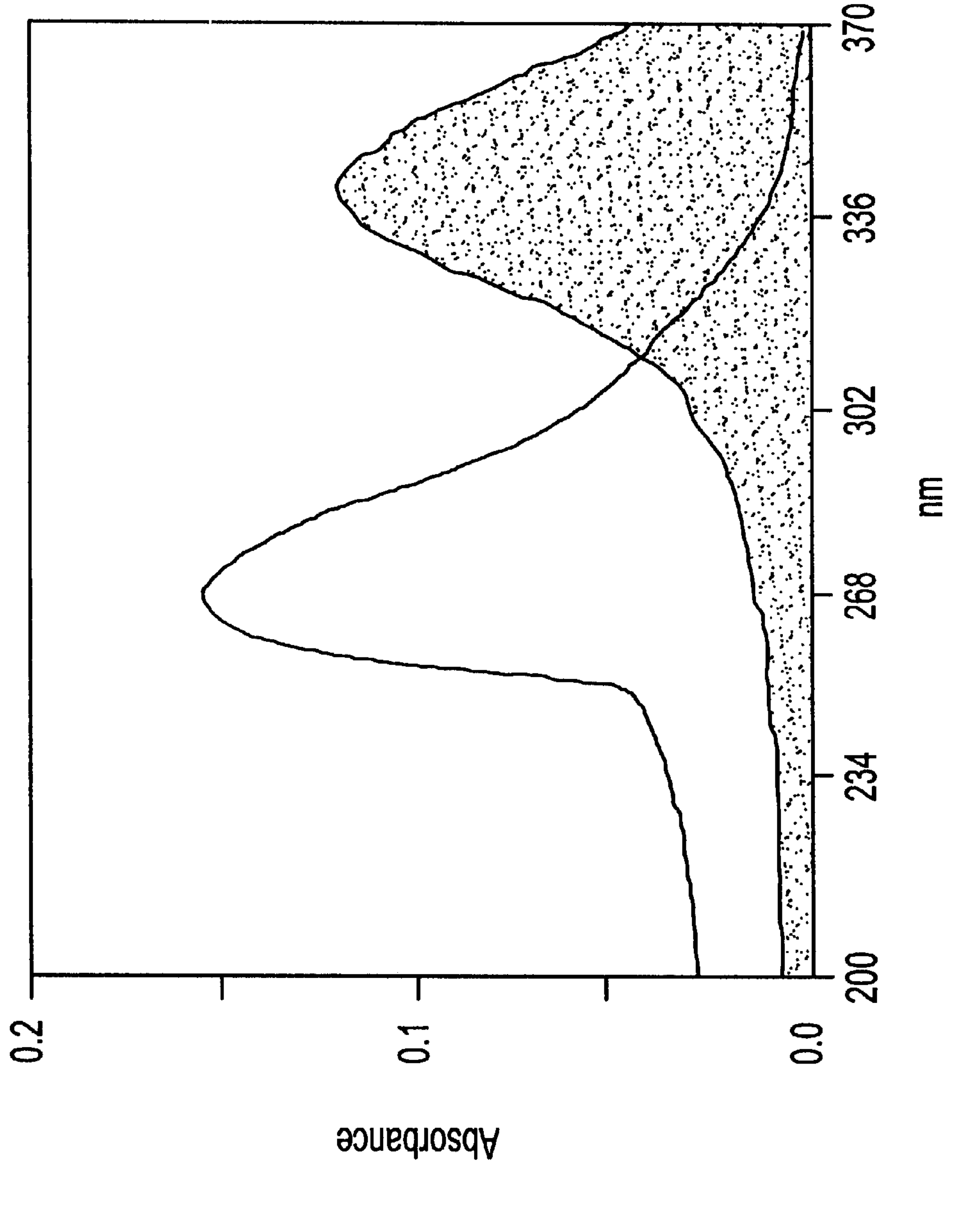

FIG. 18 is an ultraviolet spectra of Hob-SR10 (unshaded) and $(SR\text{-}10)_4$-Hab-MAP (shaded).

FIG. 19 is a schematic of the reaction scheme using thiolactones in the site-specific modification of proteins and a table including examples of substituted thiolactones.

Figure 21:
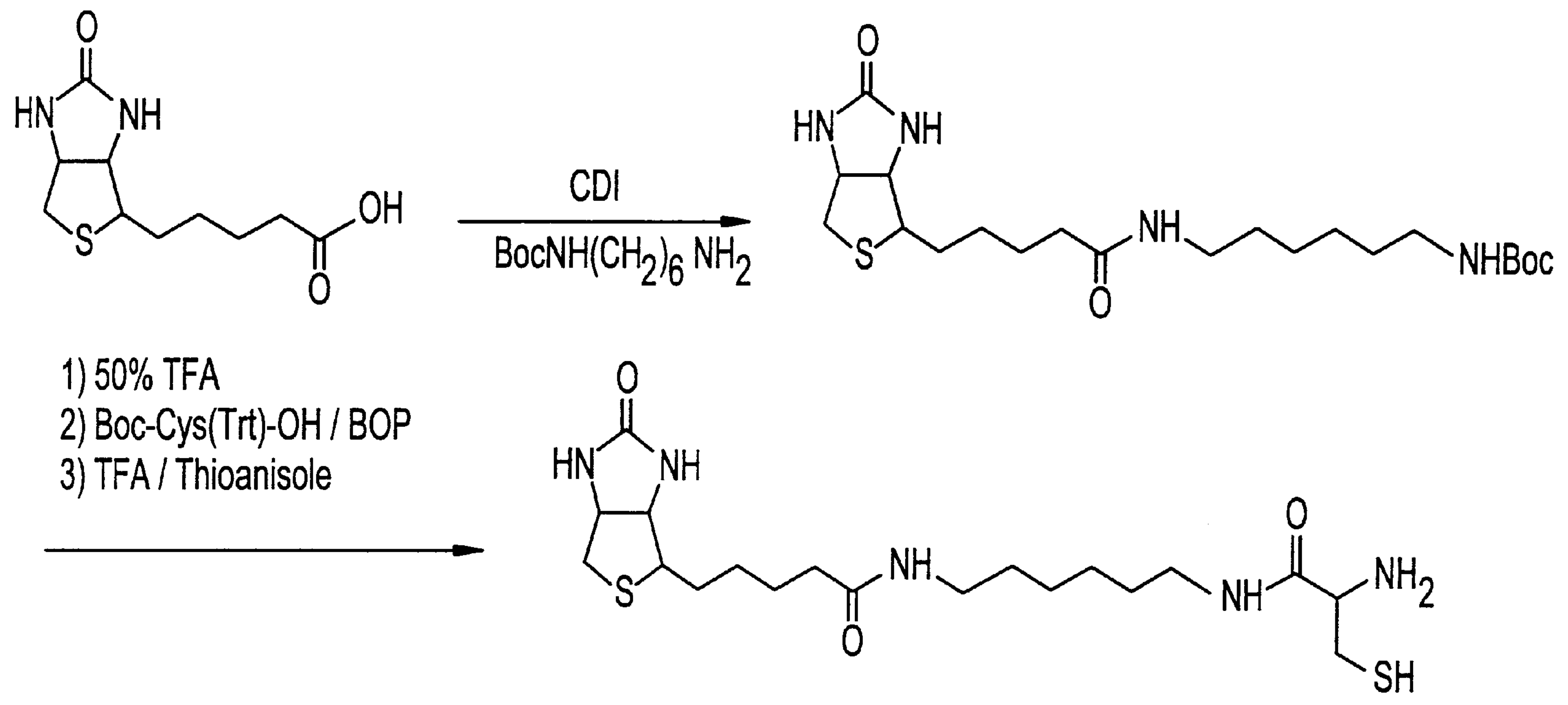

FIG. 20 is a general scheme for site-specific modification of peptides and proteins through an orthogonal coupling of 1,2-aminothiol with an aldehyde to form thiazolidine FIG. 21. Preparation of Biotin-C6-Cys (BCC) for site-specific biotinylation.

FIG. 22. RP-HPLC analysis of (A) periodate-oxidation of model tetrapeptide TMKA; (B) conjugation with BCC with the expected diastereomeric products (1 and 2), HPLC condition: see Example 14, Materials and Methods: (C) mass spectrometric analysis of the expected product.

Figure 23:
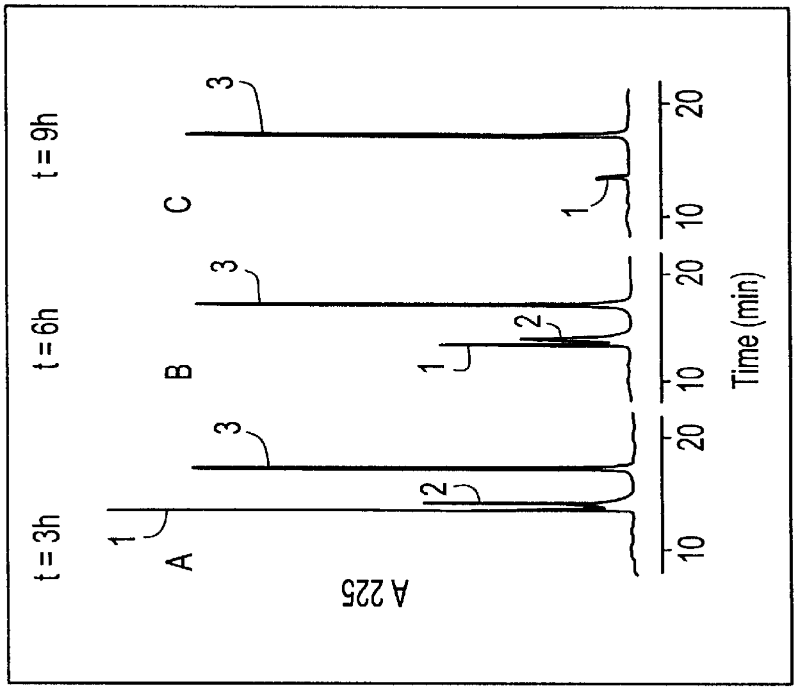

FIG. 23 RP-HPLC monitored progress of biotinylation of SR-10 (SSQFQIHGPR SEQ ID NO:14) after 3 hours (A), 6 hours (B) and 9 hours (C). 1=BCC, 2=N-glyoxylyl-SQFQIHGPR SEQ ID NO:14 and (3)=Biotin-C6-Thz-SQFQIHGPR SEQ ID NO:14. HPLC condition: see Materials and Methods, Example 14.

Figure 24:
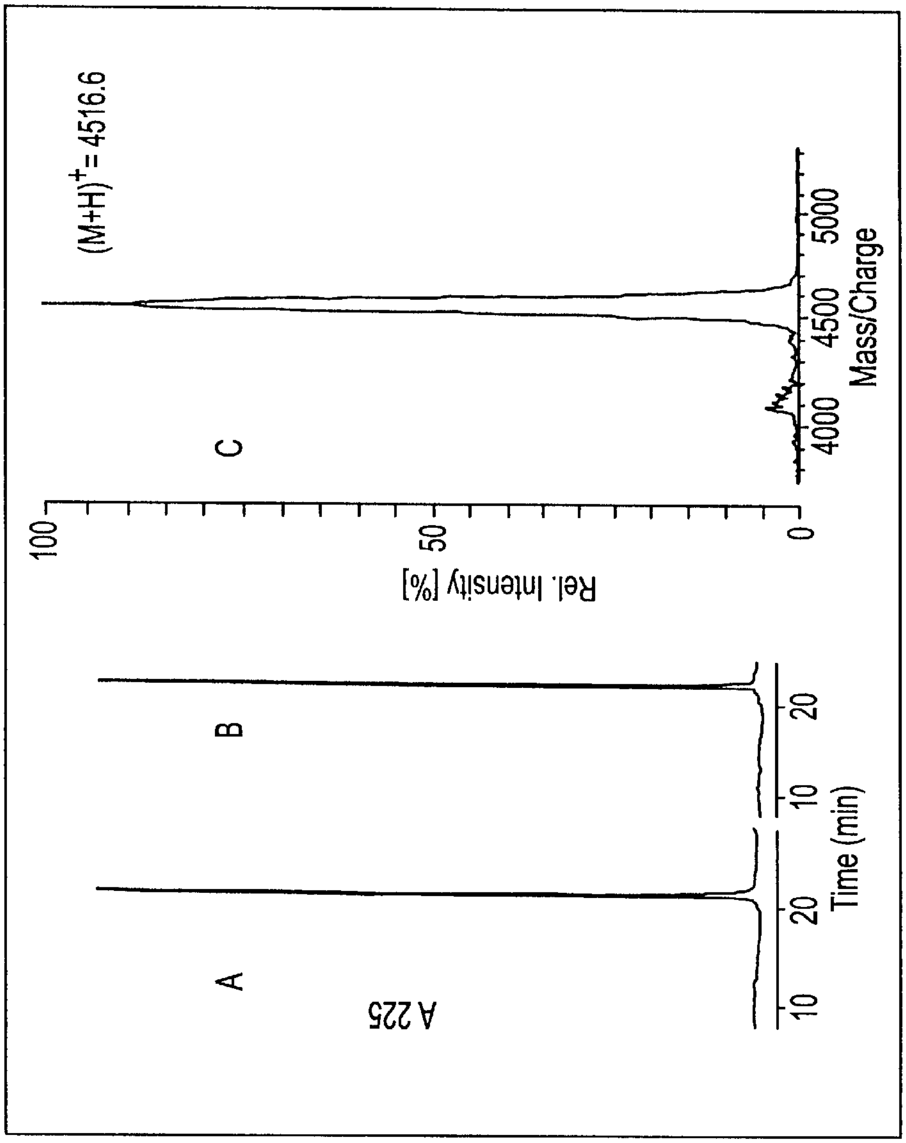

FIG. 24 RP-HPLC analysis of α-N-glyoxylyl-PTH (human) (A) and biotinylated PTH (human) (B). HPLC condition: see Materials and Methods. Massspectrometric analysis of biotinylated PTH (C).

Figure 25:
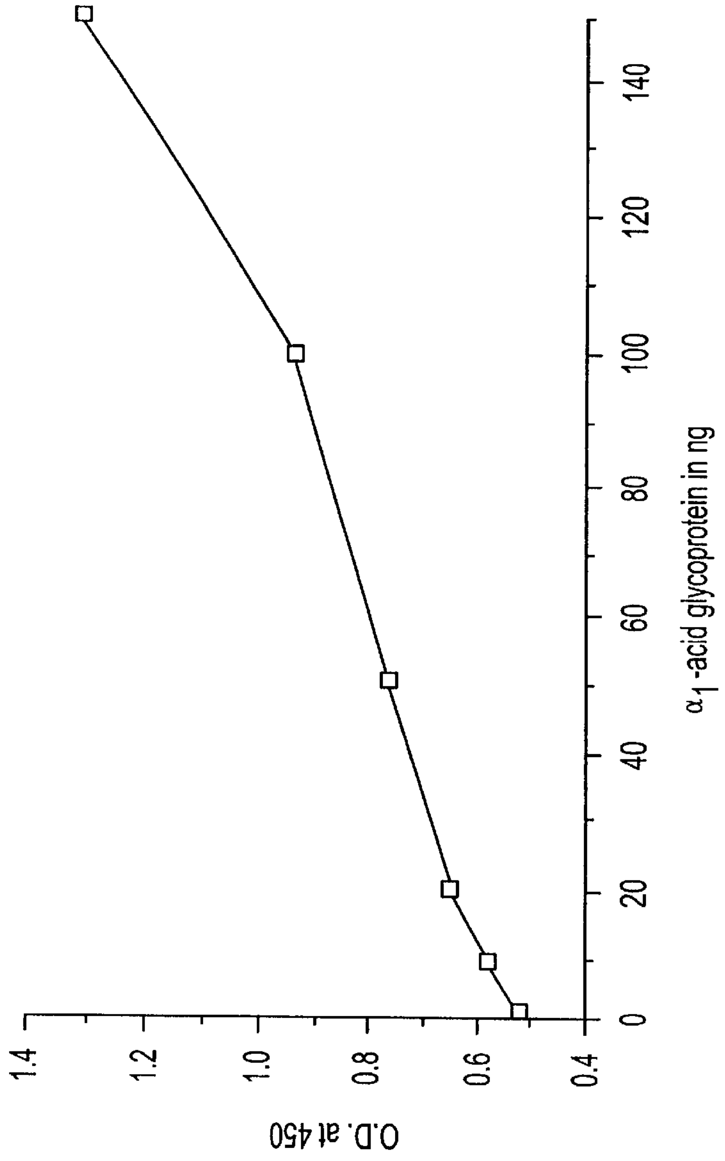

FIG. 25. Detection of biotinylated $\alpha_1$-acid glycoprotein. 1 to 150 ng of $\alpha_1$-acid glycoprotein was biotinylated after oxidation for 30 minutes at 4° C. with 10 mM $NaIO_4$ and incubation with 50 fold excess of BCC overnight. Triplicate samples were then subjected to ELISA analysis and stained with avidin-peroxidase conjugate.

Figure 26:
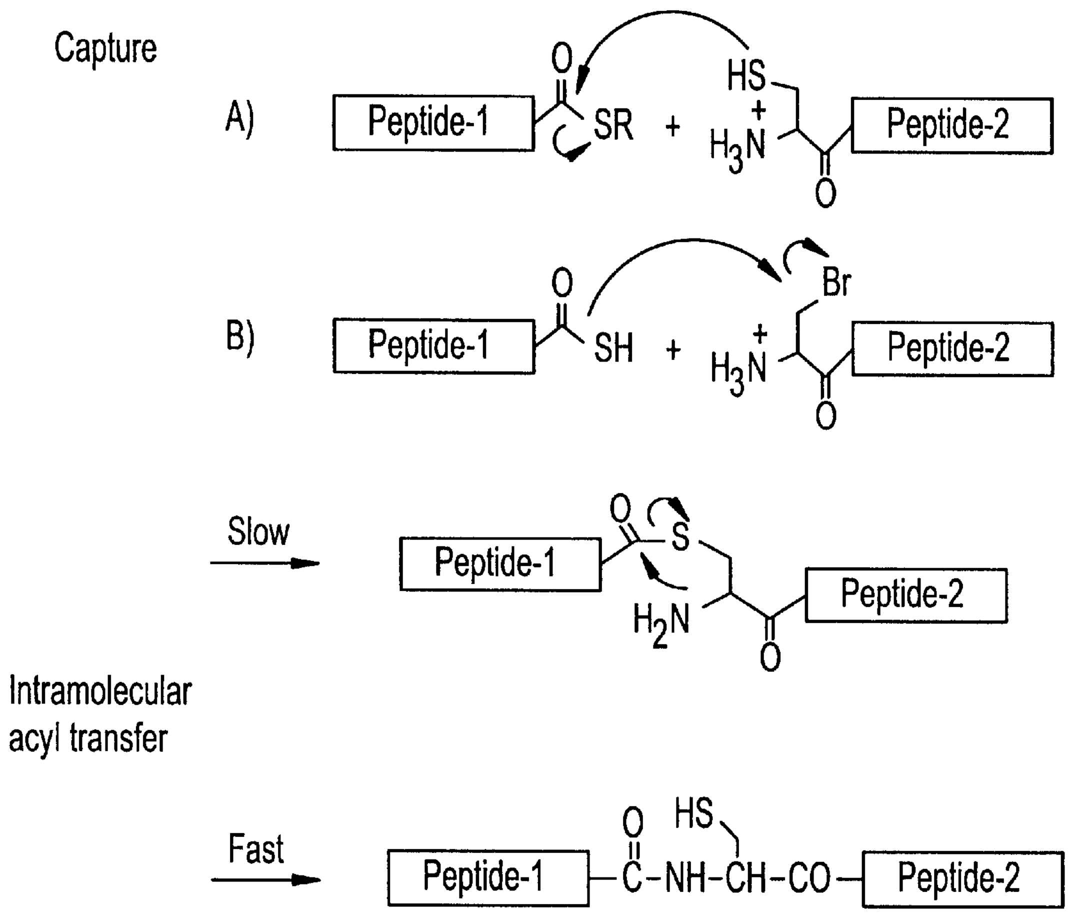

FIG. 26. Two elements of our approach to peptide synthesis using unprotected peptide segments:

A. Orthogonal coupling as capture by (1) thiol-thioester exchange and (2) thioesterification and;

B. A spontaneous intramolecular acyl transfer.

Figure 27:
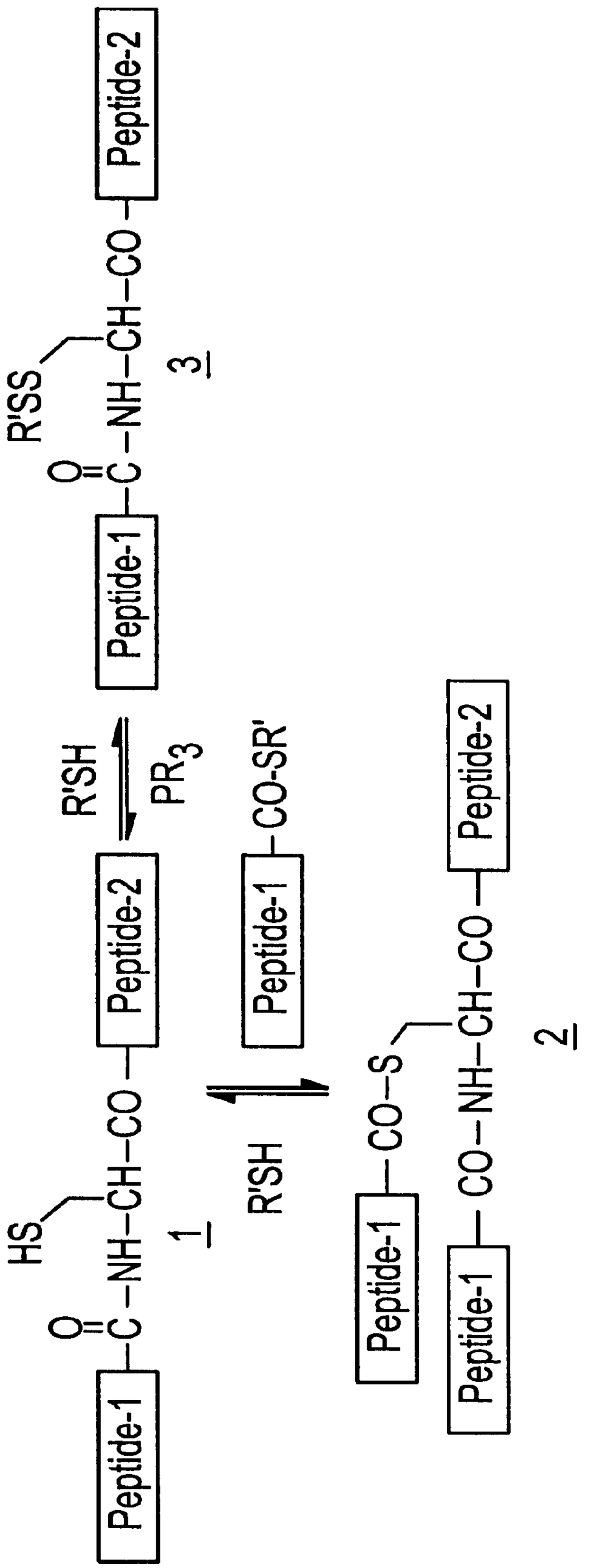

FIG. 27. Major products and their interconversion in the model reaction of CA-4F and BocGlySR. Three represent products with mixed disulfide where $R^1$=CA-4F, 1 and thiopropionic acid.

Figure 28A:
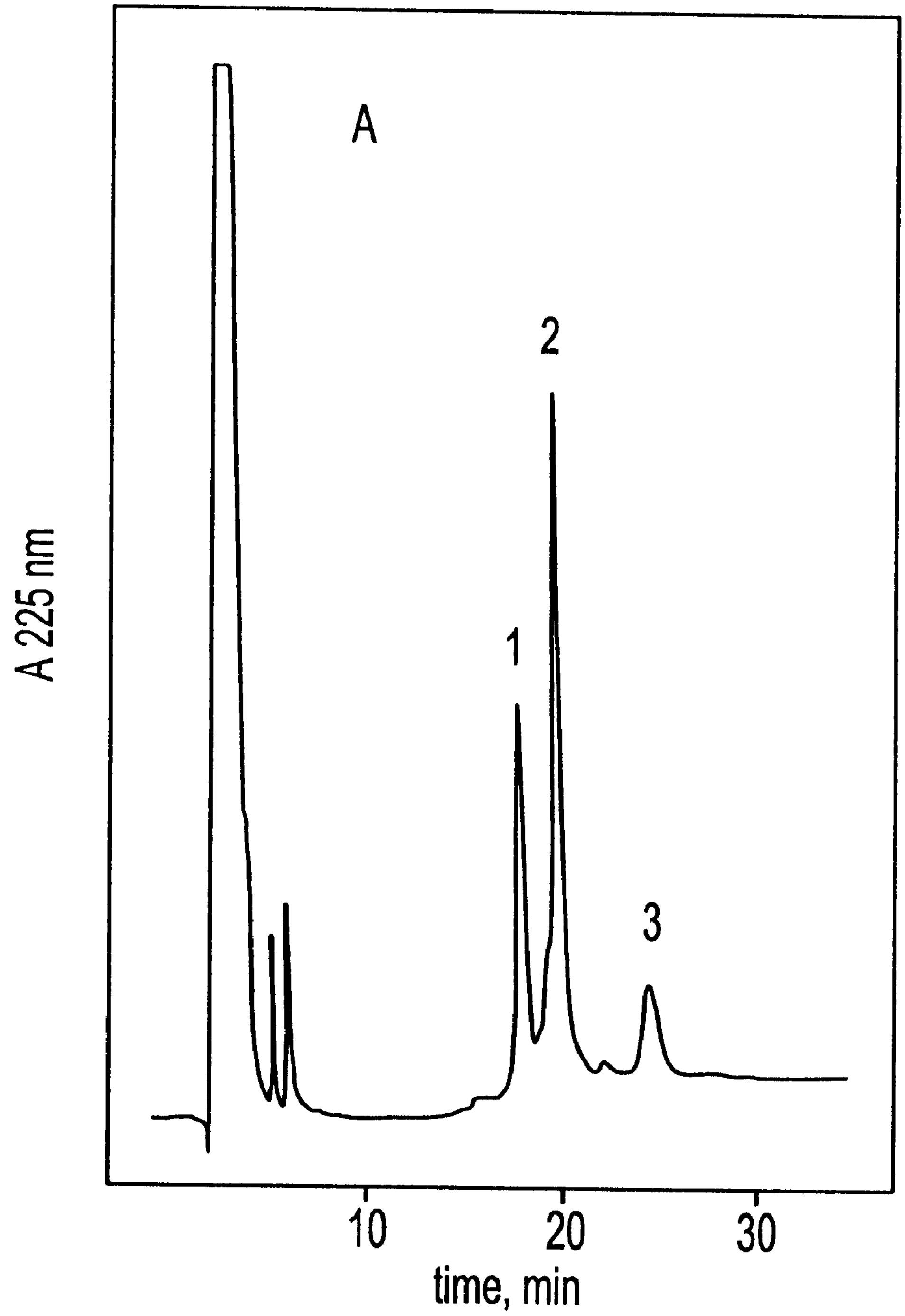
Figure 28B:
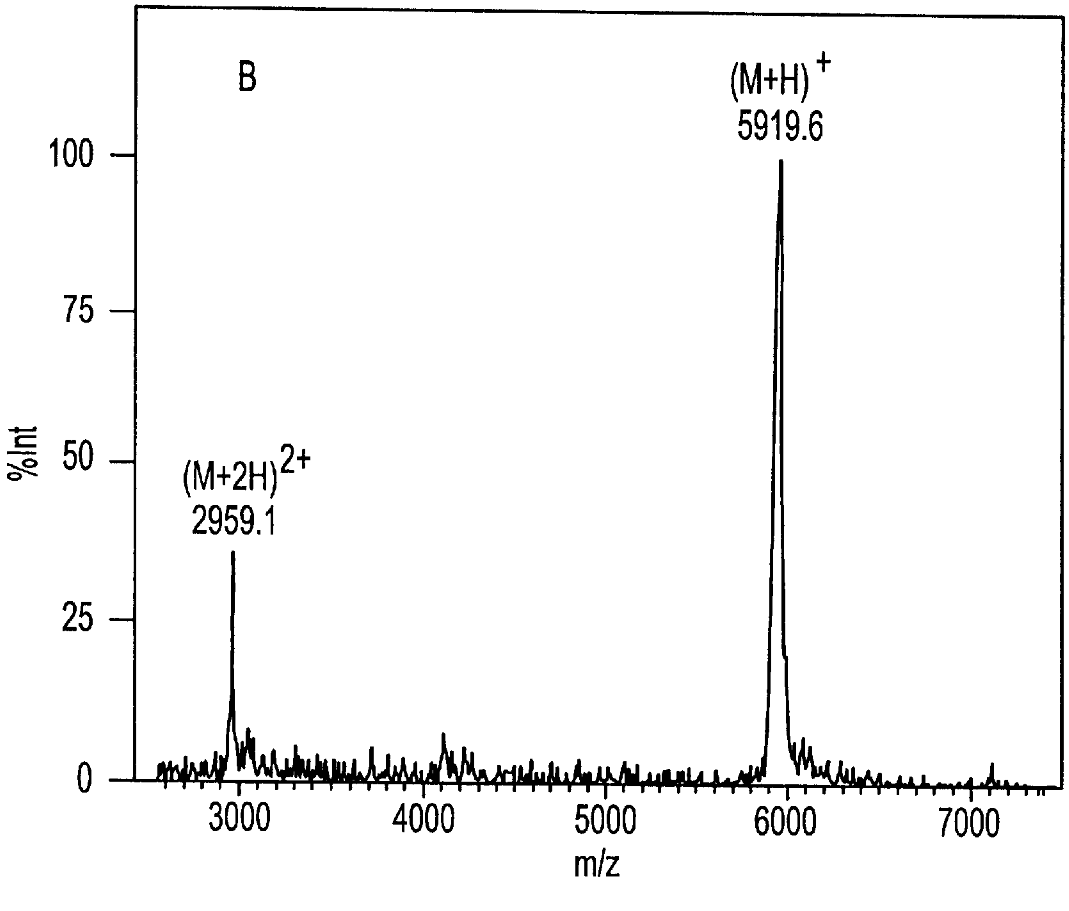

FIG. 28. A. RP-HPLC of coupling PN-37 (Peak 1) and CA-17 (eluted near solvent point) by thiol-thioester exchange to give PA-54 (Peak 2) after 12 h. Peak 3 is an artifact.

B. MALDMS of PA-54.

Figure 29:
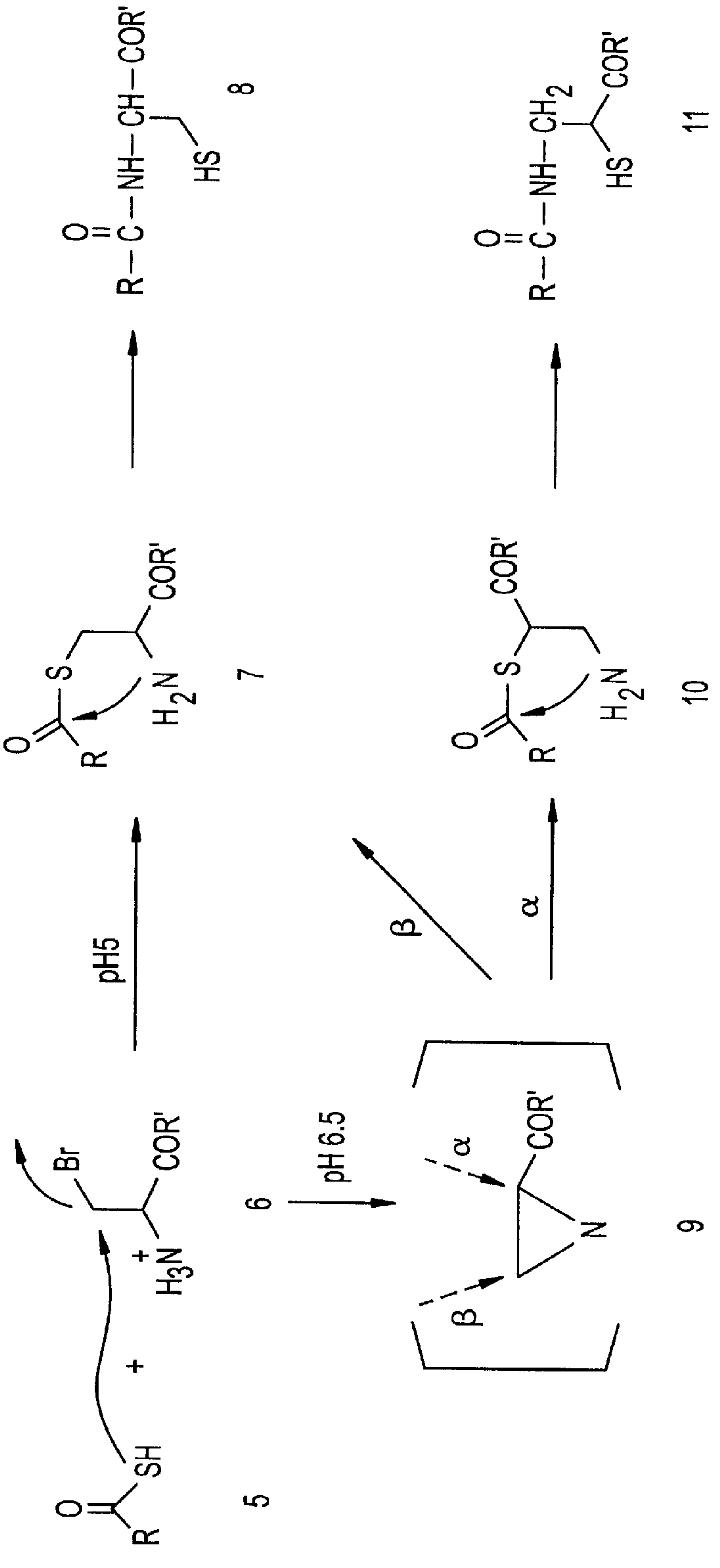

FIG. 29 Mechanism and products of thioesterification by thiocarboxylic acid and bromoalanine L and the aziridine intermediate 9.

Figure 30:
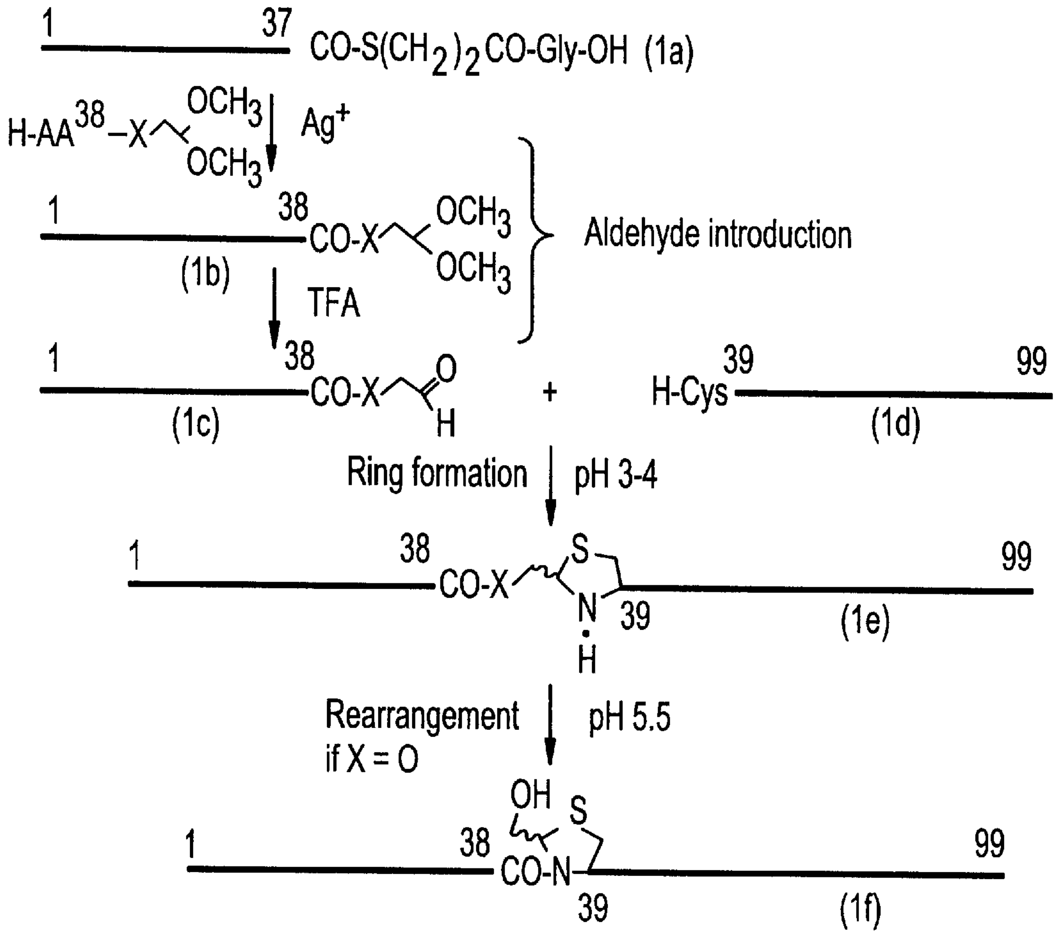

FIG. 30. Overall strategy for the synthesis of HIV-1 PR analogs. The aldehyde introduction step consists of coupling of the thioester, 1a, activated by silver ion with an α-amino acyloxy(or amido-)acetaldehyde masked as methyl acetal in large excess (~100-fold) and deblocking the acetal to yield the desired (1–38) acyl segment 1c. Ring formation between lc and id upon aldehyde capture of the 1,2-aminothiol of the N-Cys of 1d gave the thiazolidine product, 1e, which underwent a spontaneous O,N-acyl transfer to yield the final product with a thioproline (SPro) at position 39, if. AA=amino acid residue; X═O or NH. If X═O, [$SPro^{39}$, $Abu^{67.95}$]-PR and [$Ala^{38}$, $SPro^{39}$, $Abu^{67.95}$]-PR were obtained with AA38=Leu or Ala respectively. If X=NH, the synthetic scheme ended at stage 1e and [Leu-$NHCH_2$-$Thz^{38\text{-}39}$, $Abu^{67.95}$]-PR was obtained with $AA^{38}$=Leu. Amino acid sequence of HIV-1 protease: H-$P^1$ Q I T L W Q R P L V T I R I G G Q L K E A L L D T G A D D T V L E E M N L $P^{39}$ G K W K P K M I G G I G G F I K V R Q Y D Q I P V E I C G H K A I G V L V G P T P V N I I G R N L L T Q I G C T L N $F^{99}$-OH SEQ ID NO:40. Amino acid residues are represented by the standard single letter code. The ligation site was at $Pro^{39}$. The underlined sequence represents the flap region; the highly conserved active site sequence is in italics. The two $Cys^{67.95}$ residues were replaced with L-a-aminobutyric acid (Abu) in our synthetic analogs.

Figure 31:
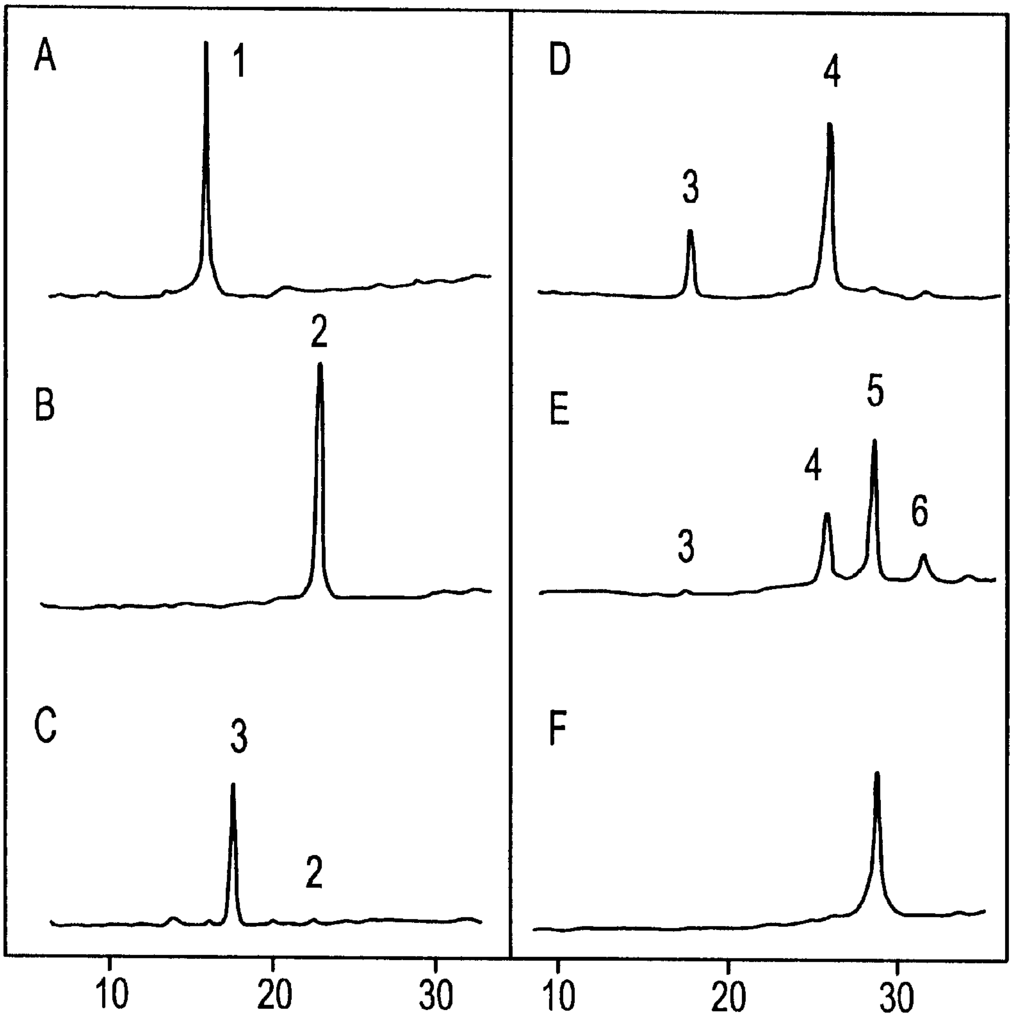

FIG. 31 $C_{18}$ RP HPLC monitoring of the progress of the synthesis of [$SPro^{39}$, $Abu^{67.95}$]-PR. (A) Purified thioester segment, HIV-1 PR(1-37)-$S(CH_2)_2CO$-Gly-OH (peak 1); (B) Purified HIV-1 PR(1-38)-$OCH_2CH(OCH_3)_2$ (peak 2) after coupling of HIV-1 PR(1-37)-$S(CH_2)_2CO$-Gly-OH activated by silver nitrate with H-Leu$^{38}$-$OCH_2CH(OCH_3)_2$ (large excess) in DMSO; (C) Demasking of the acetal by TFA (5% $H_2O$) to give HIV-1 PR(1-38)-$OCH_2CHO$ (peak 3) in 10 min at 0° C.; (D) Ligation of HIV-1 PR(1-38)-$OCH_2CHO$ (Peak 3) with [Cys$^{39}$, Abu$^{67.95}$]-HIV-1 PR(39-99) (Peak 4), t=O; (E) After 5 hr: desired ligation product (Peak 5) and peak 6 is the disulfide dimer of Peak 4; (F) Purified product. HPLC was run with a linear gradient of 40 to 80% buffer B at 1% per min in buffer A.

Figure 32:
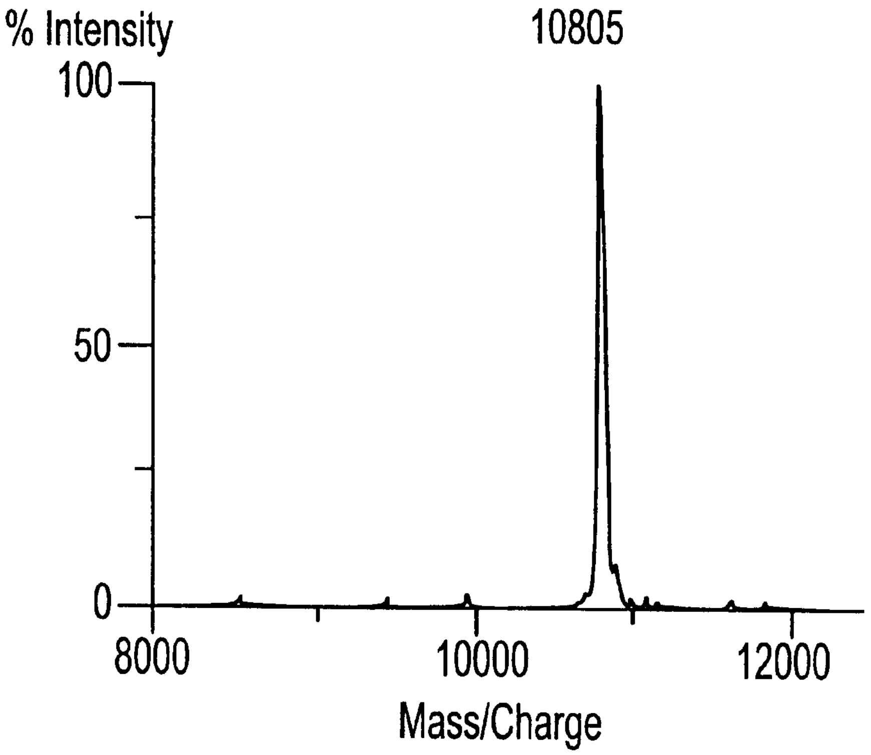

FIG. 32. MS analysis of [SPro$^{39}$, Abu$^{67.95}$]-HIV-1 PR by MALDMS.

Figure 33:
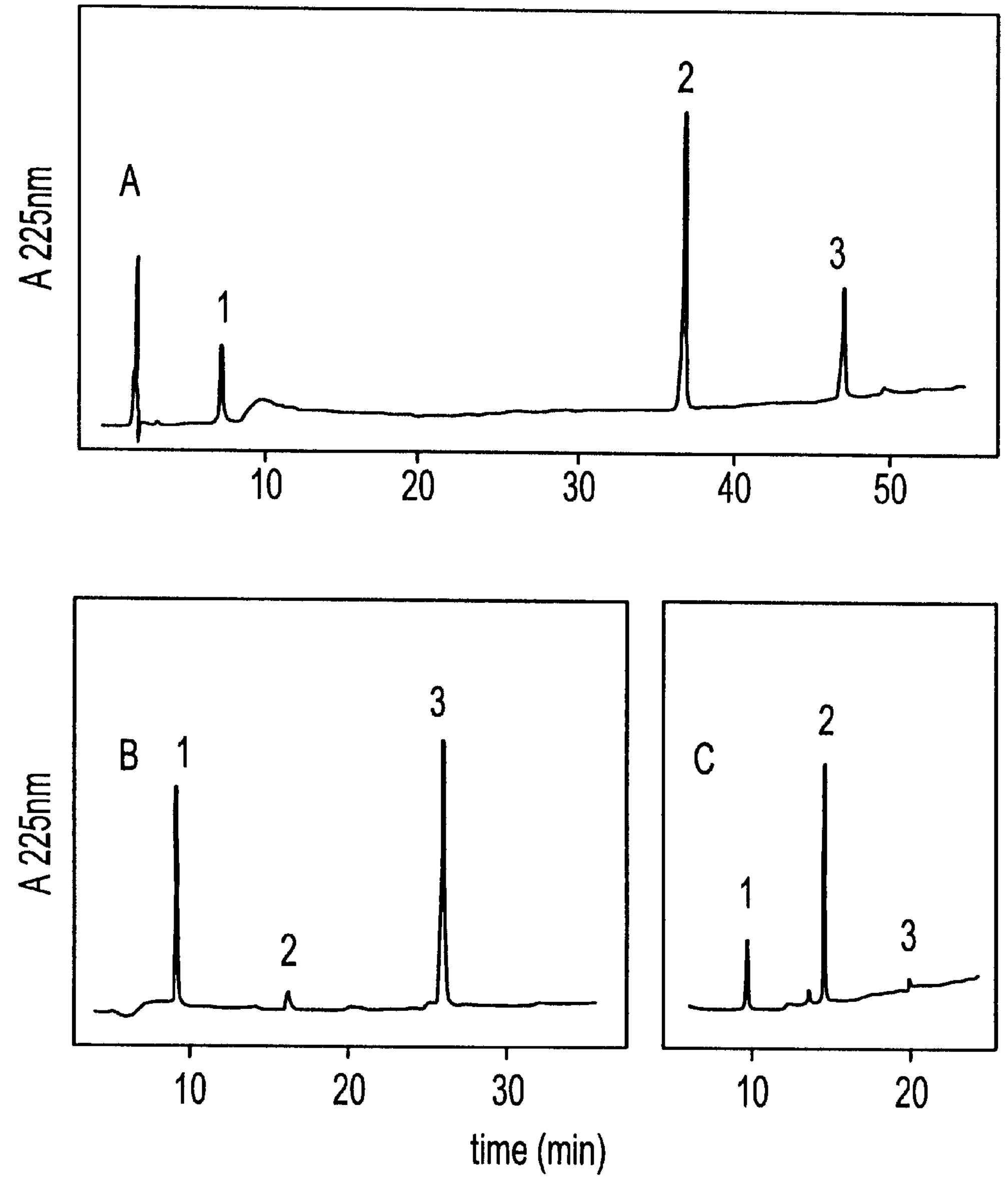

FIG. 33. $C_{18}$ RP HPLC analysis of the enzymatic hydrolysis of three different synthetic substrates by the protease analogs. (A) Hydrolysis of 100 ml of 0.2 mM 2-aminobenzoyl-Thr-Ile-Nle-Phe(p-$NO_2$)-Gln-Arg-$NH_2$ (2-aminoethyl-SEQ ID NO:9-$nH_2$) in 0.1M MES (pH 5.5) buffer catalyzed by [SPro$^{39}$, Abu$^{67.95}$]-HIV-1 PR (0.5mg) at 22° C. for 15 minutes Peak 1: H-Phe(p-$NO_2$)-Gln-Arg-$NH_2$; peak 2: 2-aminobenzoyl-Thr-Ile-Nle-OH; peak 3: remaining substrate. HPLC gradient: 0 to 55% of buffer B in buffer A over 55 minutes (B) Hydrolysis of 100 ml of 0.1 mM H-Val-Ser-Gln-Asn-Tyr-Pro-Ile-Val-OH SEQ ID NO:11 catalyzed by ~0.35 mg of [Ala$^{38}$, SPro$^{39}$, Abu$^{67.95}$]-HIV-1 PR in 50 mM acetate buffer (pH 4.7) containing 1 M NaCl at 22° C. for 20 minutes Peak 1: H-Val-Ser-Gln-Asn-Tyr-OH; peak 2: H-Pro-Ile-Val-OH; peak 3: remaining substrate. HPLC gradient: 0 to 40% buffer B in buffer A in 40 minutes (C) Hydrolysis of substrate IV (100 $\mu$l, 30 $\mu$M), H-Lys-Ala-Arg-Val-Nle-p-nitro-Phe-Glu-Ala-Nle-$NH_2$ SEQ ID NO:12-$nH_2$ by [Abu$^{67.95}$, SPro$^{39}$]-HIV-1 PR (0.2 $\mu$g) in 50 mM NaOAc buffer, pH 4.7 with 1 M NaCl and 10% glycerol for 15 minutes Peak 1: H-Lys-Ala-Arg-Val-Nle-OH SEQ ID NO:41; peak 2: H-p-nitro-Phe-Glu-Ala-Nle-$NH_2$; SEQ ID NO:39 peak 3: remaining substrate. HPLC gradient: 5 to 65% buffer B in buffer A in 30 minutes

DESCRIPTION OF THE PREFERRED EMBODIMENT

In its broadest aspect, the present invention provides a method of chemically ligating a first molecule, such as a first peptide segment, to a second molecule, such as a second peptide segment. It also provides a method of chemically ligating a peptide to a branched protein or other macromolecule. It further provides a method for the site-specific modification of proteins by chemically ligating such proteins to other peptides, proteins, or non-peptide macromolecules.

The rationale for the approach of the invention can be summarized as follows: First, large unprotected peptide segments have significant advantages of capably forming ordered structures and conformational assistance. Second, the bond formation between the segments does not necessarily involve the α-amine but is rather between the α-carboxylic acid and the side chain of the α-amino terminus using an orthogonal coupling method as a capture method. Once a covalent bond is formed, the amide bond formation can be effected through a proximity-driven intramolecular acyl transfer, a concept observed in nature as protein splicing and shown in FIG. 1.

The entropy is overcome by the use of unprotected peptide segments and the orthogonal coupling method to bring the amino and acyl segment in close proximity. The proximity-driven intramolecular transfer also solves the problem of entropy as well as acyl activation.

Thus, a key to the present method depends on the development of various orthogonal coupling methods as the capture so that the bond formation is the first step between the α-carboxylic acid and side chain of the amine segment.

The orthogonal coupling method is similar in concept to the orthogonal protecting group and proceeds independently of the amines and other functional moieties. The present invention may utilize any of three orthogonal coupling methods in the capture step. These include reactive pairs to form (1) disulfide; (2) thiazolidine; and (3) thioester. Reactive pairs of orthogonal coupling with relatively strong affinity or reactivity to each other can be found in the second and third rows of the periodic table for the analogs of nitrogen and oxygen. For example, sulfur is found to be an excellent replacement for α-COOH, thio carboxylic and thioesters. It is also within the scope of the invention to use selenium, and even lower analogs.

In the capture step, there is a covalent bond formation between the two components. This capture can be initiated either by the nucleophilic side chain or the nucleophilic acyl component which leads to a subsequent intramolecular acyl transfer to give the peptide bond. This is also shown schematically in FIG. 1.

In the practice of the present invention, the side-chain initiated capture and the intramolecular acyl transfer reaction can be effected in a number of ways which utilize particular substituents which result in orthogonally ligation of the first molecule to the second molecule.

In a first specific embodiment of the present invention, a thioester exchange reaction which utilizes a 1,2-aminothiol moiety on either the first molecule or the second molecule, and a thioester moiety on either the second molecule or the first molecule, respectively, is used. Preferably, a 1,2-aminothiol of cysteine, a 1,2-aminoethanol of serine or a 1,2-aminoethanol of threonine is used as the 1,2-aminothiol moiety.

A second specific embodiment of this invention involves a thioesterification reaction which utilizes a thiocarboxylic acid on either the first molecule or the second molecule, and a 1,2-aminohaloethane moiety on either the second molecule or the first molecule, respectively.

In a third specific embodiment of the present invention, a thioesterification reaction which uses a thiocarboxylic acid on either the first molecule or the second molecule, and an aziridine moiety on either the second molecule or the first molecule, respectively, is used.

A fourth specific embodiment of the instant invention involves the use of a disulfide exchange reaction which utilizes an acyl mixed disulfide moiety on either the first molecule or the second molecule, and a 1,2-aminothiol moiety on either the second molecule or the first molecule, respectively.

In a fifth specific embodiment of the present invention, a disulfide exchange reaction which utilizes a thiocarboxylic moiety on either the first molecule or the second molecule, and a 1,2-aminoethane disulfide moiety on either the second molecule or the first molecule, respectively, is used.

A sixth specific embodiment of this invention involves the use of an N-acylation reaction which utilizes a 1,2-aminoethane imidazole moiety on either the first molecule or the second molecule, and an acyl mixed disulfide moiety on either the second molecule or the first molecule, respectively.

In a seventh specific embodiment of the present invention, an O-acylation reaction which utilizes a 1,2-aminoethane carboxylic moiety on either the first molecule or the second molecule, and an acyl mixed disulfide moiety on either the second molecule or the first molecule, respectively, is used.

An eighth specific embodiment utilizes a weak base moiety on either the first molecule or the second molecule which is reacted with an aldehyde moiety on either the second molecule or the first molecule, respectively. Preferably, this reaction of the weak base moiety with the aldehyde moiety is performed under acidic conditions. The weak base moiety is preferably selected from the group consisting of a 1,2-aminothiol of cysteine, a 1,2-aminoethanol of serine, a 1,2-aminoethanol of threonine, an aminooxyacetyl functional group, a mono-hydrazinesuccinyl functional group, and a 4-hydrazinobenzoyl functional group.

This last embodiment is an advantageous method for ligating one peptide segment to itself or two peptide segments to each other by using a masked aldehyde ester incorporated onto the carboxylic group of a first peptide segment through an enzymatic coupling procedure, which masked aldehyde ester is then released in order that it may react with a β-functionalized amino group of a second peptide segment to form a ring leading to an O to N-acyl rearrangement step which results in the formation of an amide bond between the peptide segments. This strategy involves a series of steps including: (1) aldehyde initiation in which a masked glycolaldehyde ester is linked to the carboxylic group of an unprotected peptide by enzymatic reaction; (2) ring formation in which the regenerated aldehyde reacts with the N-αamine of the second unprotected peptide; (3) rearrangement where the O-acyl linkage is transferred to the N-acyl linkage to form a peptide bond at higher pH; (4) reconversion to the natural amino acids if necessary. Only α-amino acids which have a 1,2-disubstitution pattern and are able to form a five member ring, and 1,3-disubstituted α-amino acids which are able to form a six member ring are able to attain the proper physical spacing which will allow an intramolecular reaction to occur.

This method brings two unprotected peptides together with unusual regiospecificity through their respective carboxyl and amino functional groups. To achieve this, simple alkyl aldehydes are introduced at the carboxyl terminus of one peptide segment that will then react selectively with the N-αamino group of the second peptide component. The two peptide segments which are to be ligated could comprise opposite ends of the same polypeptide segment, if circularization of the peptide is desired. Ligation of two separate peptide segments will result in a straight chain peptide segment.

Figure 1:
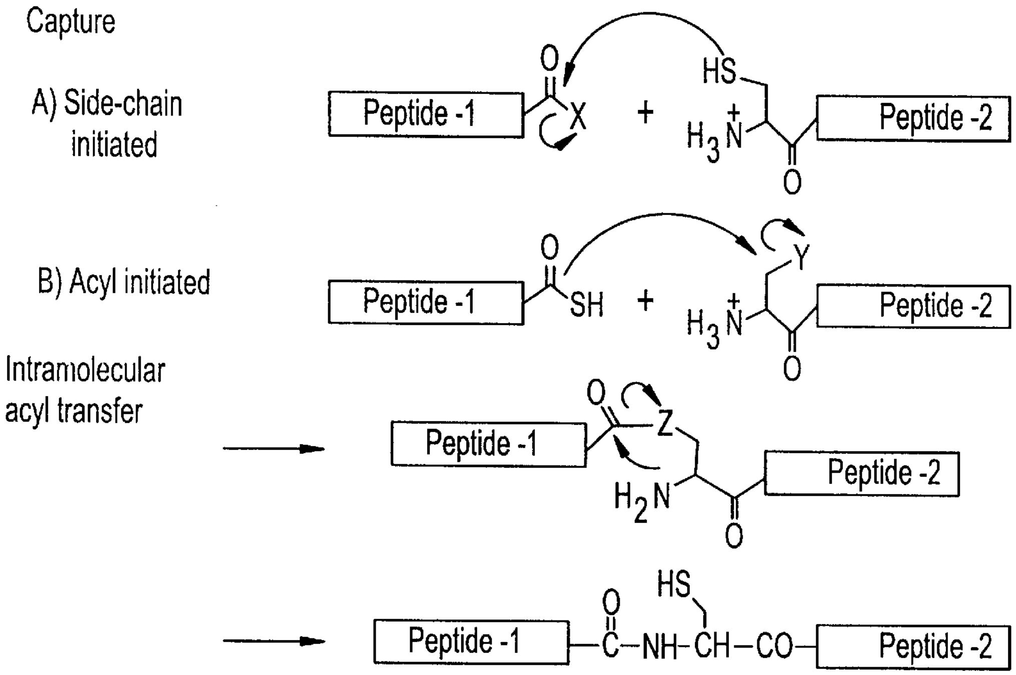
FIG. 1 is a chemical formula representation of the general concept of the method of the present invention.
Figure 2:
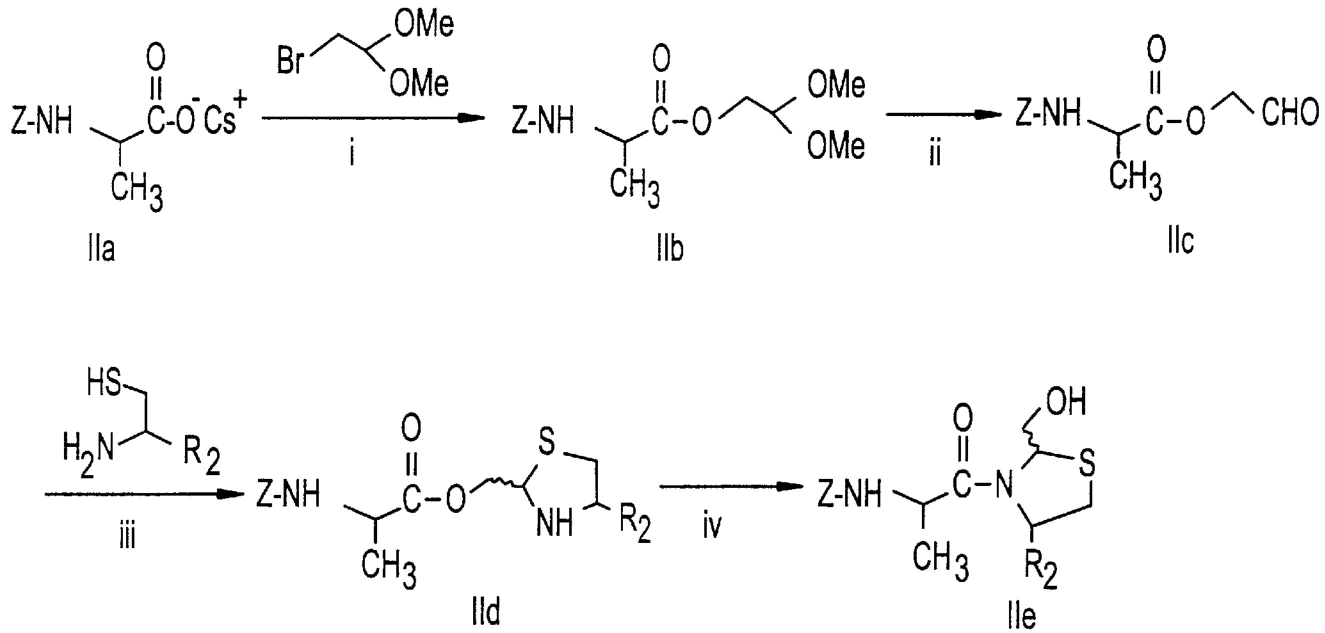
FIG. 2 is a chemical formula representation of an example of the use of the method of the present invention using small compounds.

Aldehydes condense with amines to form imines which are unstable and reversible in aqueous solution unless a ring or conjugated system is formed. The reversibility of the reaction of aldehydes with amines and the stability of ring formation with β-functionalized amines is crucial in the design of this chemical ligation strategy. Side chain amines which do not contain a β-functionalized thiol or hydroxyl group are incapable of ring formation. Specifically, an alkyl aldehyde is introduced via an ester linkage to a carboxyl group of one peptide segment to be captured by the second peptide segment bearing a β-functionalized amino-terminal amino group (such as those occurring in Cys, Thr and Ser residues) to form a relatively stable five or six-member ring (FIG. 1). Only α-amino acids which have the 1,2-disubsitution pattern or the 1,3-disubstitution pattern will allow ring formation. Side chain functional groups are not capable of forming the ring. Furthermore, this reaction is usually performed at pH 5 or 6 to further avoid Schiff base formation with side chains of Lys or Arg. The net result is that the carboxyl and amino components are brought together by a ring formation leading to a well positioned and facile intramolecular O to N-acyl rearrangement to form the desired amide bond. Thus, peptide bond formation occurs without activation by a coupling reagent which is an invariable feature of the conventional approach.

The two reacting termini could be from the same peptide if the intention is for circularization. The ester bond which links the peptide segment and the aldehyde is positioned in such a way that an amide bond can then be formed through an intramolecular O to N-acyl transfer reaction (FIG. 1). The domain ligation strategy employs the α-acyloxyacetaldehyde system (a glycolaldehyde ester, or an α-formylmethyl ester of the carboxylic component). In this system the acyl carbonyl land the aldehyde carbonyl are separated by two atoms to facilitate a 5-member ring or by three atoms to facilitate a 6-member ring transition state.

The domain ligation strategy for forming a peptide bond between the opposite ends of one unprotected peptide segment or two separate unprotected peptide segments has high selectivity and efficiency and reaction rate, as well as the ability to be conducted under aqueous conditions, all of which are essential elements of a useful chemical ligation method. The domain ligation strategy meets all of these requirements. The unique reactivity of an aldehyde with a β-mercaptoamino compound under acidic conditions makes it unnecessary to protect other functional groups. This reactivity also accomplishes the ligation of two components with a high effective molarity through the efficient O to N-acyl transfer reaction. Furthermore, this rearrangement permits the formation of an amide bond without the participation of an activated carboxylic group.

The N to O-acyl transfer reaction is a common side reaction in peptide synthesis and usually occurs in anhydrous acid treatments to give an ester linkage similar to that formed in domain ligation strategy. This side reaction is reverted back, i.e. the reverse O to N-acyl transfer reaction to give the normal peptide bond, with great efficiency using a base treatment at pH 8–9. The modified Thr (oxazolidine) and Cys (thiazolidine) can be converted to their respective amino acid by treatment with aqueous base.

Some therapeutic applications of this method include production of proteins having unusual architectures. Selected proteins for design are circularized and branched proteins. Target circularized proteins include interleukin-1 receptor antagonist which is currently in clinical trials as a drug to reduce severity of sepsis and arthritis; monitor peptide which is a cholecystokinin-releasing factor and may be useful for treatment of digestive disorders; and defensin which is a broad-spectrum antibiotic with promising activity against AIDS-related pathogens. Target branch proteins will include a malaria vaccine containing the protective antigen derived from merozoite. surface protein (MSP-1). This antigen is the most promising vaccine candidate to date.

Domain ligation strategy comprises a method to link or circularize totally unprotected peptide and protein segments via a peptide bond without activation. This method is well suited for the synthesis of circularized and branched proteins which are inaccessible directly by recombinant DNA methods and are difficult to obtain by the conventional methods of peptide synthesis. The domain ligation strategy employs a combined approach of organic and peptide chemistry in engineering proteins for therapeutic applications.

Circular proteins differ from cyclic proteins because they are connected end-to-end by a peptide bond, while cyclization is a non-specific circularization. These cyclized proteins represent difficult synthetic targets because several of them contain three disulfide bonds. However, methods developed for their synthesis would be applicable to most other peptides and proteins. In addition, they have potential therapeutic values and circularization may improve their half-life in vivo and increase stability against proteolytic degradation, particularly the exopeptidases. Unlike cyclic peptides, synthetic circularized proteins are rare because they are not leasily accessible to methods presently available. One example, BPTI, uses non-specific carbodiimide for its circularization. Thus, methods developed in this application will make these circular proteins readily available for biochemical, biophysical, and therapeutic evaluations. Furthermore, the domain ligation strategy can be extended and amplified to other applications, such as ligating proteins or peptides with DNA for biological studies.

Another application of the domain ligation strategy is linking multiple copies of lunprotected peptides or proteins to a scaffold or template by an amide to produce a branched protein. This application has broad utility and this method would provide a specific and stable conjugation for peptide/protein antigen to a carrier, drug to a protein, reporter group to an antibody or enzyme, and many others.

This invention also relates to a method using the same concept of ligation for site-specific modification of peptides or proteins by lipidation and pegylation. More particularly, the invention relates to the modification of the protein gp120 derived from the human inmmunodeficiency virus-1 at the amino terminus to contain one or more lipid side chains (lipidation) to increase its efficacy for vaccine and the modification of cytokine interleukin-2 by polyethylene glycol (PEG, pegylation) to increase its stability. The vaccines and other biomolecules that are modified in accordance with the invention are also contemplated herein.

In this connection, and with reference to the Table following below, representative peptides prepared by the present invention are set forth by way of non-limiting examples.

Peptide Synthesized by Capture-Activation

| | No. | Segment Size | | Internal | |
|---|---|---|---|---|---|
| Peptide | a.a. | acyl | amine | SH | Method |
| CK-15 | 15 | 9 | 6 | + | A |
| a-TGFα | 49 | 32 | 17 | + | A |
| a-HIVPR | 99 | 39 | 60 | − | A |
| a-HIVPR | 99 | 39 | 60 | − | A |
| a-HIVPR | 98 | 38 | 60 | − | A |
| SA-9 | 9 | 5 | 4 | − | B |
| GA-10 | 10 | 6 | 4 | − | B |
| AA-34 | 34 | 17 | 17 | − | B |
| PA-54 | 54 | 37 | 17 | + | B |
| SV-11 | 11 | 4 | 7 | − | C |
| FA-32 | 32 | 15 | 17 | − | D |
| a-HIVPR | 99 | 42 | 57 | + | D |
| IL-1β | 153 | 70 | 83 | + | D |

A Aldehyde capture
B Thioester exchange
C Thioesterification
D Disulfide exchange
a = analog In addition to the above, certain specific moieties reacted in the embodiment involving the aldehyde ester strategy are as set forth below by way of nonlimiting example, in the claims appended hereto, and such disclosure is incorporated herein by reference as if explicitly stated at this juncture.

The present invention will be better understood from a review of the following illustrative examples, wherein specific embodiments hereof are set forth.

Throughout these examples, the following abbreviations are used:

ACM acetamidomethyl
Ala alanine
Ala ODMOE 2-dimethoxyethyl ester of alanine
Arg arginine
Boc t-butyloxycarbonyl
Bzl benzyl
Cys Cysteine
DCC dicyclohexylcarbodiimide
DCM dichloromethane
DIEA diisopropylethyl amine
DMF dimethylformamide
DMSO dimethylsulfoxide
Dnp dinitrophenyl
EDTA ethylenediarninetetraacetic acid
FM formylmethyl ester
Fmoc fluorenylmethyloxycarbonyl
Gly glycine
Hab aldehyde-4-hydrazinobenzoyl adduct
HBTU 2-(1H-benxotriazol-1-yl)-1,1,3,3-tetramethyluronium
HOBt 1-hydroxybenzotriazole
HPLC high pressure liquid chromatography
His Histidine
Hob 4-hydrazinobenzoyl
Ile Isoleucine
LDMS matrix assisted laser-desorption mass spectrometry
Leu leucine
Lys lysine
NMR nuclear magnetic resonance
NaOH sodium hydroxide
Phe phenylalanine
Pro proline
Ser serine
TFA trifluoroacetic acid
Thr threonine
Thz 4-hydroxymethyl, thiazolidinyl carboxylic acid
Tos toluenesulphonyl
Trp tryptophan
Tyr tyrosine
X any amino acid
Z benzyloxycarbonyl
Z-Ala carbobenzoxyalanine
Z-Ala-Pro carbobenzoxyalanyl proline

EXAMPLE 1

The initial step of this example involves the reaction of Z-Ala with a masked acetal containing the aldehyde function (formylmethyl ester, FM) as the carboxyl component which was obtained by reacting the Cs salt of Z-Ala with bromoacetaldehyde dimethyl acetal in DMF. Acetal is particularly suitable because of its ease of removal and it gives an unreactive side product (MeOH) which eliminates the need for a purification process. Treatment with 30% TFA in acetonitrile or the most TFA-compatible organic solvent used in peptide synthesis for acid deprotection, such as $CHCl_3$, $CH_2Cl_2$, $CCl_4$, toluene, etc., in a trace amount of $H_2O$ at 0° C. for 15 to 20 minutes smoothly converted the acetal to its aldehyde Z-Ala-OFM. After TFA and the solvents were removed, the aldehyde was allowed to react without purification with β-mercaptoethylamine, cysteine, cysteine methyl ester, or threonine methyl ester to form thiazolidine or oxazolidine, which rearranged to the amide form at higher pH.

The reaction of carbonyl compounds with cysteine involves an initial reaction of sulfhydryl with the carbonyl to give an addition product which condenses with the N-α of the amino group of the cysteine to form a cyclic thiazolidine derivative over a wide range of pH. To avoid the hydrolysis of the ester and the unwanted reaction of aldehyde with the side chain amino groups, the reaction of cysteine or other β-mercaptoamines was conducted with aldehydes at pH 4 to 5. Under these conditions the thiazolidine product was formed almost immediately. At lower pH, this reaction was slower. At pH 2 the reaction required 1–2 hours for completion. The thiazolidines were stable and were easily purified by normal or reversed phase HPLC under usual conditions.

EXAMPLE 2

The basic character of the secondary amine in the thiazolidine ring makes it possible for the acyl group to migrate from the ester oxygen to the nitrogen. The O to N-acyl transfer reaction is a dominating side reaction in the acidic deprotection step of peptide synthesis during which the acyl moiety of the peptide migrates from the amine to the free hydroxy group on the side chain of a serine or threonine residue. The transfer reaction is reversible upon base treatment involving a 5 member ring oxazolidine-like transition state. Table 2 below shows that O to N-acyl rearrangement was effective even at the acidic pH range. The weak basicity of the thiazolidine amine (pKa 6.2) may have contributed to this. Rearrangement occurred in all the pH conditions from pH 6 to pH 9. The rate of the reaction was largely dependent on the pH value. As shown in Table 2, for IId1 to IIe1, at pH 9, the $t^{1/2}$ for the rearrangement is about 3.4 hours and the reaction proceeds cleanly without any detectable side products, while at pH 6 the $t^{1/2}$ is about one day with some side products probably due to the regenerated aldehyde by slow reversible hydrolysis.

TABLE 2

Rate ($t_{1/2}$ hour) of the O- to N-Acyl Transfer Reaction

| pH | 5 | 6 | 7 | 7.4 | 8 | 9 |
|---|---|---|---|---|---|---|
| IId1 to IIe1 | | 37.5 | 22.2 | 20.2 | 9.9 | 3.4 |
| IId2 to IIe2 | | 55 | 8.4 | 9.5 | 11 | 9.3 |

EXAMPLE 3

Both the condensation products and the rearranged products give a mixture of two diastereoisomers due to the creation of a new asymmetric carbon at position 2 of the thiazolidine ring. These diastereoisomers are HPLC separable. The difference between the ester (before rearrangement) and amide (after rearrangement) forms is distinguishable in the following ways: analytically (HPLC), spectrometrically (NMR) and chemically. In the NMR studies, the prominent changes are the disappearance of the proton signals for the secondary ammonium protons in the thiazolidine ring and an up-field shift of two protons on the methylene carbon linked to the oxycarbonyl which, after rearrangement, became an hydroxyl group. The ester form is susceptible to alkali hydrolysis under saponification conditions, whereas the amide form is stable. Treatment of the ester product IId1 with 0.1 to 1 N NaOH gave Z-Ala-OH as the hydrolyzed product along with the rearrangement product in 10 minutes, while the amide form IIe1 was stable under the same conditions.

The rearrangement product now resembles a Z-Ala-Pro structure with a thiol ether linkage as the isoelectronic replacement of the methylene carbon at position 4 and an hydroxymethyl substitution on position 5 of the proline ring. Such modifications will unlikely change the backbone conformation of a proline-containing peptide chain. Thus, this pseudo X-Pro bond can generally be viewed as a substituent for any of the X-Pro bonds present in protein sequences and further enlarges the scope of application of the domain ligation strategy. The N-acyl thiazolidine structure is similar in structure to an acetamidomethyl protected form (Acm-like) of the cysteine residue, and can be reverted to the thiol to form a disulfide by the usual oxidative cleavage method.

EXAMPLE 4

The activation step whereby the formylmethyl ester is introduced to the unprotected peptide segment is an essential element of this method of peptide ligation. With synthetic peptides, this should not pose a problem, since new resins have been developed to give such a linker functional group containing a formylmethyl ester at the carboxyl moiety. For proteins derived from recombinant DNA or natural sources, an activation step is needed. The key is the introduction of the masked aldehyde function onto the carboxylic group of the first component by using the specificity of an enzyme.

Figure 4:
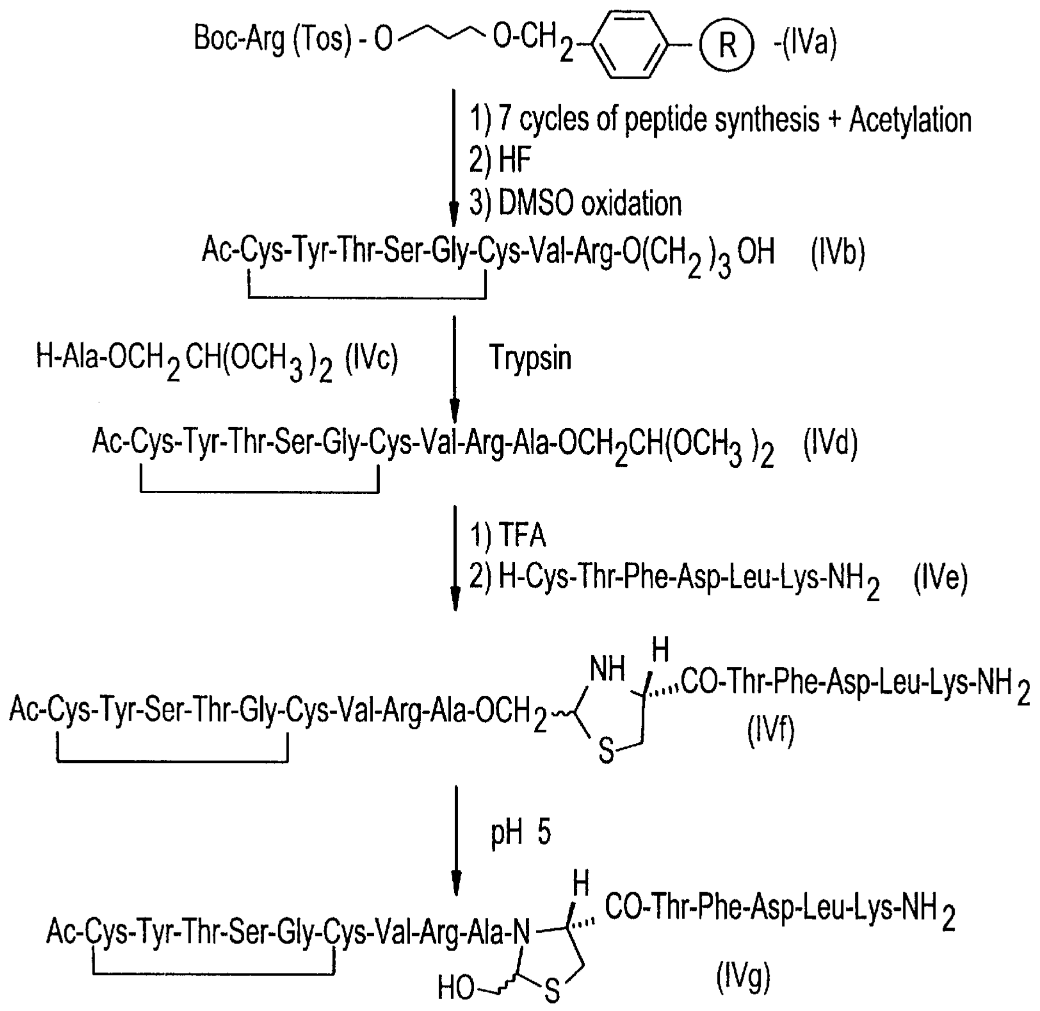
FIG. 4 is a chemical formula representation of an example of the domain ligation method of the present invention, specifically showing the synthesis of a pentadecapeptide—(SEQ ID NO: 1)—.
Figure 5A:
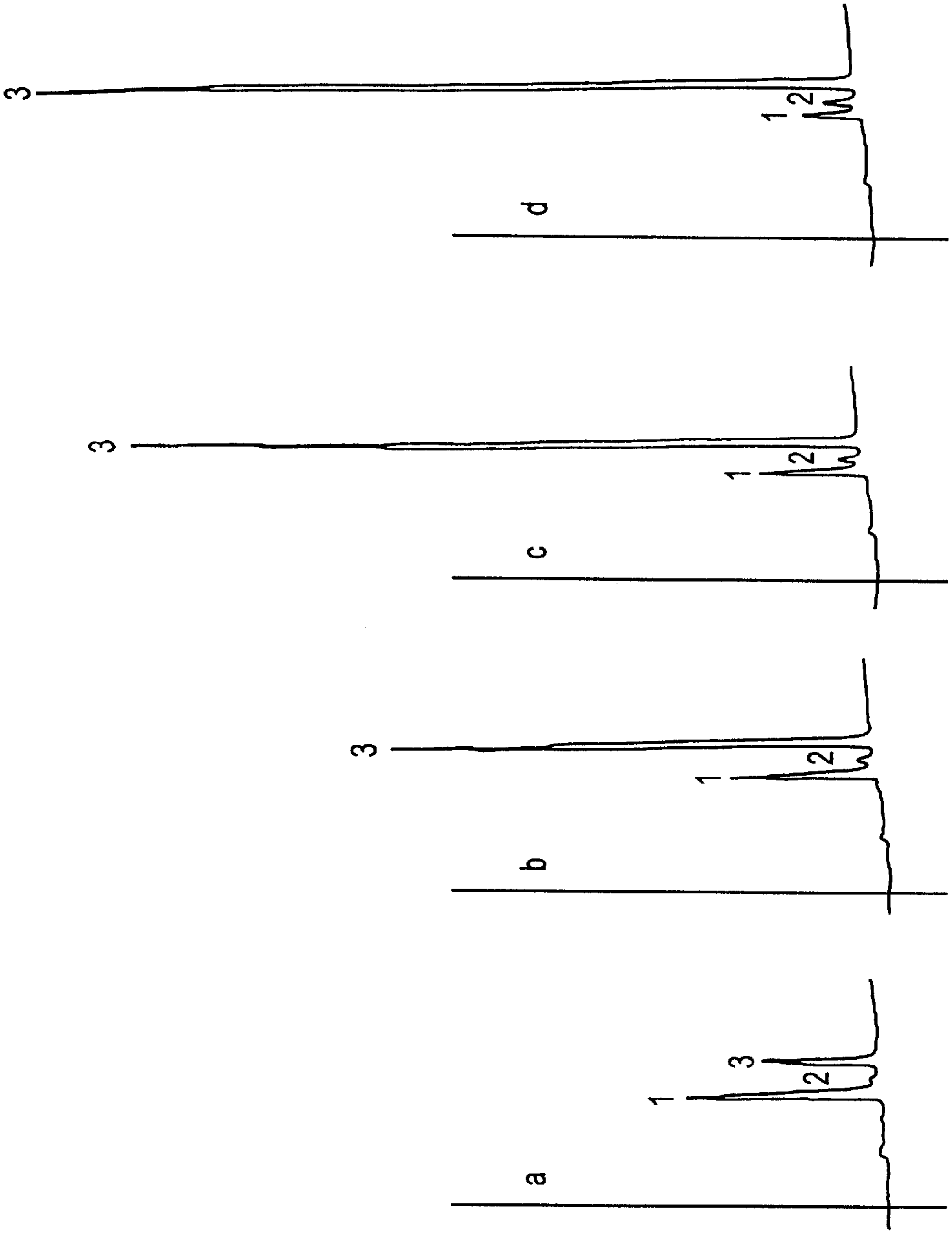
FIGS. 5A and 5B are HPLC profiles of the rearrangement reaction step of the method of the present invention from compound IId1 to IIe1 as shown on FIG. 2. under the following conditions.
Figure 5B:
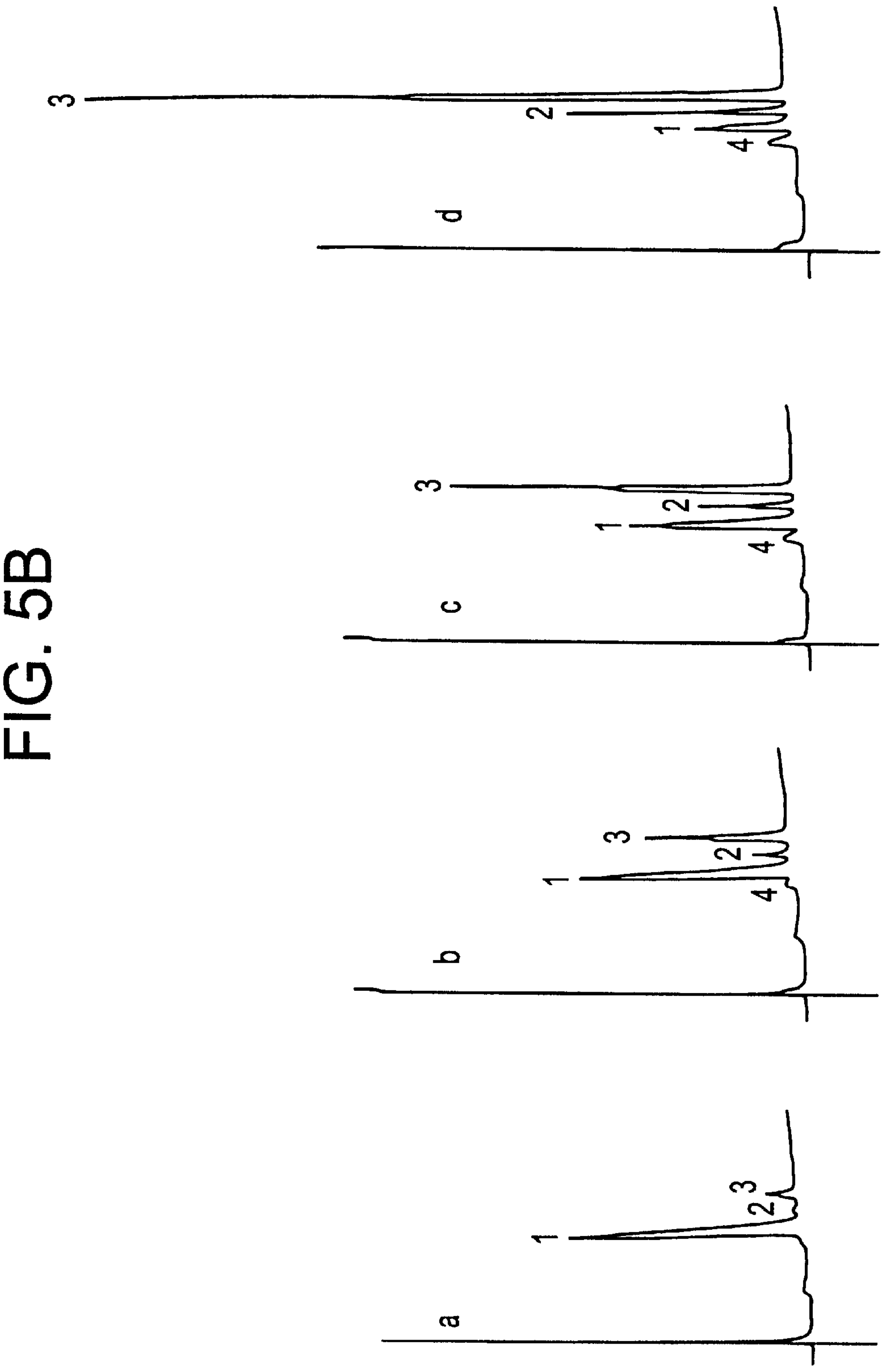

Kinetically controlled aminolysis by enzymes of a peptide ester in the presence of a water miscible organic solvent could be smoothly and efficiently accomplished if a high concentration of the amino component is used. In this case, a large excess of dimethoxyethyl ester of alanine was used. The carboxylic component peptide ester was synthesized by solid phase peptide synthesis method using a newly developed resin (see FIG. 4: IVa). After the cleavage and removal of all protecting groups, this resin provided a peptide containing a carboxyl ester (FIG. 4:IVb)—(SEQ ID NO:3)—which is a good substrate for enzyme catalyzed coupling. The enzymatic coupling between the peptide and the small substrate, the 2,2-dimethoxyethyl ester of alanine, abbreviated AlaODMoE (IVc) was catalyzed by trypsin in 60% or more DMF and completed within a short time (<½ hour) under the condition of high molar concentrations and large excess of the amino component (FIG. 4:IVc). After the enzymatic coupling, the capture and all subsequent steps were carried out in a similar way as described in the model study. The hexapeptide (FIG. 4:IVe) (SEQ ID NO:5) was premixed with the first peptide acetal (FIG. 4:IVd) (SEQ ID NO:4). The deprotection was achieved using 95% TFA containing 5% $H_2O$ for 3–5 minutes at 0° C. The regenerated aldehyde showed a shorter retention time in reverse phase HPLC. The HPLC did not reveal any detectable hydrolysis of the ester bond. After removal of TFA, the reactants were redissolved in an acetate buffer (pH 4) to allow the capture reaction, which was also monitored by HPLC. The strong affinity between the aldehyde and the β-thiol amino compound makes it possible that the components can be used in a very dilute molar concentration. This is highly desirable since the reaction between macromolecules has to be carried out in a dilute solution due to the large molecular masses of the reactants. Under the present experimental conditions, the concentration of both components is about 5 mM. The expected thiazolidine product formed cleanly without any detectable side reactions. The rearrangement reaction occurred after the solution was adjusted to pH 5 with aqueous acetate buffer.

All the side chain functional groups in both peptides were unprotected, including the α-amine of lysine and the β-carboxylic acid of aspartic acid residues, which inevitably have to be protected in the conventional segment coupling approach. It is also important to note that the three steps of this method (acetal deprotection, aldehyde capture and acyl transfer) could be conducted in the same reaction vessel, required only pH changes in aqueous solution and no intermediate purification steps were needed. The product formed (FIG. 4:IVg) (SEQ ID NO: 1) also did not require renaturation and oxidation to form the disulfide bond. This has simplified the experimental procedure significantly.

EXAMPLE 5

A method to study this reaction with all possible combinations of N-terminal amino acids and their side chain functionalities using a library of 400 dipeptides consisting of 20 genetically coded amino acids was employed. To this end, identical copies of a library of 400 dipeptides anchored on cellulose paper were synthesized and an alanyl ester aldehyde was allowed to react with each library under various conditions. The paper support used in these experiments served both as the solid support on which the 400 peptides were synthesized and as a monitoring device on which the ring formation could be observed.

The library was synthesized on Whatman paper using the Fmoc chemistry. The arrangement of the library was in a matrix system containing 400 spots, each representing a dipeptide. The reactivity of each dipeptide towards the aldehyde could be visualized as either a horizontal row which showed the N-terminal amino acid was reactive (e.g. Cys-X, where X represents 20 amino acids) or a vertical column which indicated that the side chains of the carboxyl terminal amino acids (e.g. X-Cys) were reactive. Furthermore, the subsequent O to N-acyl rearrangement could also be observed efficiently by changing to basic buffers or solvents under which the ester bond will be hydrolyzed and the O to N-acyl transferred product would be stable.

For the library to work efficiently, a reporter molecule on the amino acid alkyl ester aldehyde would be required to provide detection of the bimolecular reaction between the aldehyde and the dipeptides. We selected dye-labeling as a reporter group because of its high sensitivity for visible detection, stability under normal conditions, and ease of attachment to the amino acids or peptides. The color functional molecule, 2,4-(dimethylamino)phenylazobenzoic acid (Methy Red, Dpab for abbreviation) was introduced to an amino acid derivative through an amide bond which is stable toward acid and base treatments. Depending on the pH of the aqueous buffer, Dpab-amino acids possess intensive orange to red color and are visible on the paper at low concentration.

Three different aldehydes were used and were esterified to Z-Ala with the following alcohols (1) β-formylmethyl (FM) alcohol, (2) β-formylethyl (FE) alcohol, and (3) β,β,β-dimethylformylethyl (DFE) alcohol. The FM ester aldehyde will give a five-member transition state and should be 30 to 100 fold faster than either FE or DFE esters which requires a 6-member transition state in the O to N-acyl transfer reaction. ME ester rearranged approximately 100 fold faster than the hindered DFE ester and 25 fold faster than FE ester. ME ester is the ester of choice.

Six different amino acids (Cys, Thr, Ser, Trp, His and Asn) are known to form ring products with simple alkyl aldehydes, in particular with formaldehyde which has been used industrially for tanning and medically for inactivation of toxins and biological agents. Because the ME ester aldehydes could be viewed as simple alkyl aldehydes, ring formation is expected to a certain extent with these six amino acids.

Dipeptides with N-terminal Cys, Thr, and Ser (Cys-X, Thr-X, and Ser-X; where X is any amino acid) are of major interest because their ring products can be reverted to Cys, Thr, or Ser. Thiazolidine and oxazolidine can be viewed as temporary protecting groups for these amino acids. Further, the relatively common occurrence of these amino acids in proteins makes them convenient points for ligation in our strategy. The two heterocyclic amino acids Trp and His bearing weakly acidic amines are known to react with alkyl aldehydes to form bicyclic compounds. The initial kinetic ring product with the heterocyclic amine would further rearrange to the stable product involving the C-2 carbon and N-α of the amino group. These bicyclic ring products are not reversible to their natural amino acids. Similarly, the side chain amide of Asn is also known to participate in ring formation, usually under forcing conditions.

EXAMPLE 6

Ring formation in both aqueous buffered solutions at pH 5 to 8 and 90% water-miscible organic solvents at pH 7 has been studied. However, the order of reactivity was significantly different in both systems. N-terminal Cys reacted rapidly and completely with all three aldehydes at all pH ranges tested. With the unhindered FM and FE esters, the reaction was completed within 0.5 hours but required 2 hours for completion with the hindered DFE ester. In contrast, the reactivity of Thr was 500 fold slower. Ser was basically non-reactive. In general, the reactivity of the N-terminal amino acids with Dpab-Ala-O-FM could be divided into three groups. First, Cys-X reacted exceptionally fast with Dpab-Ala-OFM in either aqueous or water-miscible organic and water mixtures. The reactions were completed in 0.5 hours at pH 5–8 even at a very dilute concentration of $1\times10^{-6}$ M. Second, Thr-X, Trp-X and His-X represented a category that reacted 500 to 100,000 fold slower than Cys-X. Their reactivity was highly dependent on concentrations of Dpab-Ala-O-FM, pH, and the neighboring amino acid. Trp-X formed a heterocyclic compound in 30–50% in 160 hours at the acidic pH. Furthermore, Trp-X reacted faster than Thr-X when the concentration of Dpab-Ala-O-FM was lower than $5\times10^{-5}$ M probably due to the irreversibility of the Trp-X product.

In contrast, the oxazolidine ring and the Schiff base of Thr-X were not stable at the acidic range and only 5–30% of oxazolidines could be observed in 160 hours. At neutral and basic pH, Thr-X reacted faster than Trp-X and 20–60% of oxazolidines could be observed. N-terminal His formed a heterocyclic compound but its formation was slow at pH 5–8 and less than 10% of product was observable in 160 F hours. Third, the ring formation with Ser-X and Asn-X was essentially insignificant in aqueous solution. Asn-X reacted very slowly to form the heterocyclic compound. However, in aqueous solution less than 5% of the reaction product could be observed in 160 hours.

α-Carboxamide participates in ring formation with alkyl aldehyde. Primary amides such as Asn, Leu-$NH_2$, and Ala$NH_2$ would react with Z-Ala-O-FM to form a heterocyclic compound. Interestingly, Gln-X which would have formed a six-member ring did not react with Dpab-Ala-O-FM probably due to the slow formation of the six-member ring. Similarly, the reaction with Ser was much slower than Thr and never went to significant completion in the aqueous condition because the opened form of Schiff base and hydrolysis were favored.

The neighboring amino acids exert either rate enhancement or retardation in ring formation. When the neighboring group amino acid is hydrophobic such as X-Ile, X-Phe, X-Trp, X-Leu, X-Val, and X-Tyr, ring formation was accelerated when compared with X-Ala and X-Gly. This was particularly evident with those dipeptides containing N-terminal amino acids such as His and Ser which exhibited slow ring formation. In contrast, when the neighboring amino acids are hydrophilic and particularly acidic, such as Asp, Glu and Asn, ring formation is retarded. A possible explanation for the observed result might be the participation of the side chains in assisting the hydrolysis of the ring form to the open form or the Schiff base to the starting material. The rate enhancement of the neighboring amino acids might be due to the hydrophobic interaction of the Dpab which contains two phenyl rings with the hydrophobic sequences.

Except for Cys-X, ring formation in 100% aqueous solutions and in a very dilute concentration of Dpab-Ala-O-FM was slow for Thr-X and Trp-X, and insignificant for His-X, Ser-X and Asn-X. The equilibrium favors the open forms of either the hydroxymethyl derivatives or the Schiff base which forms are hydrolyzed by water to the starting materials. However, the equilibrium would be predicted to favor the closed forms in the absence of water. To accelerate ring formation, we experimented with the use of 90% water-miscible organic solvents such as hindered alcohol (isopropanol) and aprotic polar solvents (DMF and DMSO). The use of these water-miscible organic solvents in high concentrations are necessary for reverse proteolysis and compatible with the scheme of using unprotected peptide segments. Furthermore, water-miscible organic solvent and water have been applied to effect the incorporation of the amino ester aldehyde in the first step of the domain ligation strategy.

When the reaction was performed in 90% water-miscible organic solvent buffered to pH 7 in 10% $H_2O$, alcoholic solvents such as isopropanol did not improve the reaction rates. In contrast, the polar aprotic solvents DMF and DMSO greatly accelerated the reaction rates, particularly for Thr-X (except when X is Asp, Glu, or Asn) to give the oxazolidine ring formation in 20 hour (FIG. 1). The rate acceleration for Ser-X was difficult to quantify since only about 25% of oxazolidine was observable in 30 hours. Nevertheless, it represents an increase of about 10 fold when compared to the 100% aqueous solution. The rate enhancement was also found in the ring formation of Trp-X, His-X and Asn-X, but apparently the formation of thiazolidine and oxazolidine was more favored.

After comparing the steric effect of the carboxyl terminus bearing the OME ester aldehyde it was found that the rates of O to N-acyl transfer reaction greater favors small amino acids with Gly>>Ala>Val. Gly is the preferred C-terminus residue.

When preparing proteins containing multiple disulfide bonds, the stability of the ester during the folding, renaturation and disulfide formation, which are usually performed under basic pH and requires long duration of 2 to 3 days, is a major concern. Under such conditions, the hydrolysis of the ester is likely to occur and would lower the yield of the subsequent reaction. For this reason, a new method of peptide ligation has been developed that allows the renaturation, and selective disulfide bond formation for peptides and proteins. The key reagent in this new method was dimethylsulfoxide (DMSO). Facile disulfide bond formation by DMSO in aqueous buffered solutions proceeded across a wide range of pH, from acidic to basic. This result will allow the folding and disulfide oxidation to be performed over an acidic range of 5–6 or near neutral pH of 6–7 where hydrolysis will not be significant. The DMSO oxidation overcame the limitation of the conventional oxidation method using air or mixed disulfide that was applicable only over a narrow basic pH range. The sulfur-sulfur bond reaction by DMSO was selective and no side reactions were observed with nucleophilic amino acids such as Met, Trp, or Tyr. Detailed kinetic studies on a series of monocyclic agonist peptides of βFGF showed that disulfide formation by 20% DMSO was completed in 0.5 to 4 hours, while similar experiments by air oxidation at basic pH required longer duration and produced incomplete reactions. Facile oxidations by DMSO were observed with the basic and hydrophobic, tricyclic 29-residue human defensin and 78-residue heparin-binding EGF. In contrast, air oxidation at basic pH of these molecules led to extensive precipitation and low yields. DMSO is a versatile and useful oxidizing agent for peptides over a wide range of pH and may be particularly suitable for renaturation and oxidation of proteins at acidic pH of the domain ligation strategy.

EXAMPLE 7

Figure 3:
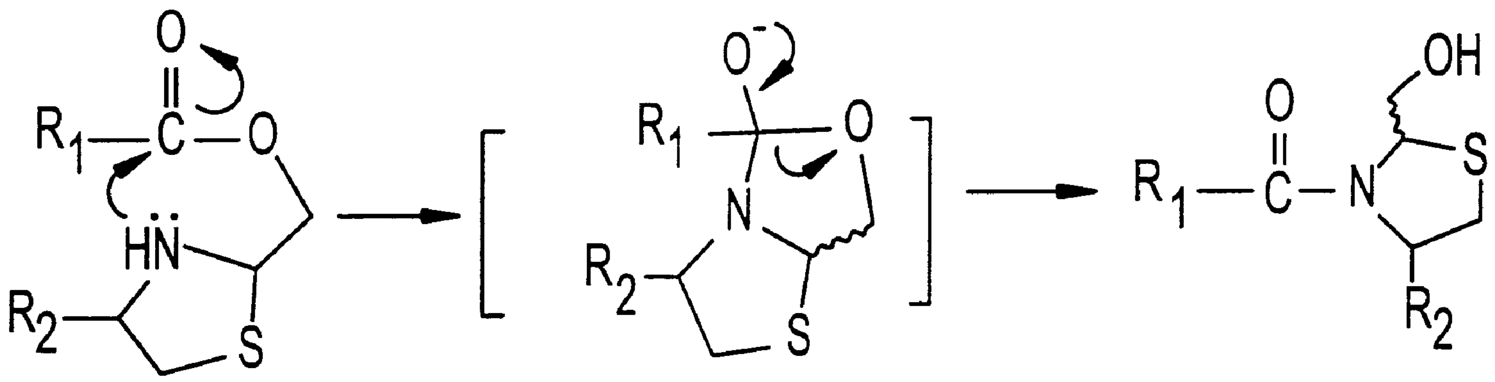
FIG. 3 is a chemical formula representation of the mechanism of the acyl transfer reaction step of the method of the present invention.

TGFα (transforming growth factor-α) is a 50-residue, three-disulfide protein. It contains two domains which are stable structures and we have shown that they can be folded to give the correct disulfide structure. We synthesized two subdomains TGFα1–32 (SEQ ID NO:6) and TGFα33–50 (SEQ ID NO:7) on a new resin (e.g. hydroxyethyloxymethyl resin) by the solid-phase method, refolded, and purified to give an carboxyl-ester and were ligated chemically as shown in FIG. 3. The resulting Thr-33TGFα (SEQ ID NO:2) has the correct molecular weight and the biological activity comparable to TGFα. This synthesis validates the concept of domain ligation strategy and points to its potential of preparing proteins with unusual structures that may not be accessible from recombinant products.

Examples 8 to 10 illustrate the facile and specific nature of the domain ligation to form peptide dendrimers. Peptide dendrimers with their characteristic branched structures represent a class of artificial proteins assembled on a scaffolding or template and which would attain the macromolecular bulk as proteins, but have the advantages that they self-assemble and obviate the need of extensive folding required for biochemical activity. The flexibility of designing scaffoldings and the attendant dendritic peptides has led to successful engineering of artificial proteins which function as enzymes, ion channels, antibiotics, diagnostic reagents, and vaccines.

Current methods of stepwise solid-phase synthesis of peptide dendrimers are inadequate to yield such macromolecular products with high purity. Although the use of protected peptide monomers offers improvements, it suffers the limitations of poor solubility and slow coupling reactions. A more direct and efficient approach is the use of nonpeptidyl linkages for the ligation reaction between the unprotected peptide segments and scaffoldings. Examples of this approach include conjugation through thioalkyation, thioester, and oxime. Other applicable but yet untried methods include hydrazone, reverse proteolysis, and domain ligation.

Domain ligation is particularly appealing because it utilizes the facile and chemoselective reaction between a weak base such as 1,2-amino thiol and an alkyl aldehyde to give thiazolidine ring under acidic condition. With small peptides, this reaction is usually completed within 10 minutes and highly specific for the N-terminal of cysteine. Unprotected side chains of lysine, arginine and other amino acids are excluded from this reaction to allow totally unprotected peptides to be ligated to an aldehyde-containing scaffolding.

Example 8 illustrates the utility of the domain ligation in the synthesis of peptide dendrimers for synthetic vaccine purposes, using an octavalent lysinyl scaffolding, popularly known as MAP (multiple antigen peptide) which consists of several levels of sequentially branched lysine.

Example 9 compares three different methods of performing the ligation using thiazolidine, hydrazone, and oxime, in the preparation of another synthetic vaccine for feline leukemia virus using the MAP approach. In each case a homogeneous compound was obtained.

Example 10 illustrates two different methods for the preparation of synthetic vaccine derived from HIV-1.

EXAMPLE 8

This example addresses the synthesis of a synthetic vaccine comprising an octameric peptide dendrimer consisting of the V3-loop of gp120 of HIV-1, MN strain.

The core matrix, consisting of a masked aldehyde, ($Ser_8Lys_4$-$Lys_2$-Lys-β-Ala), was prepared by the solid phase peptide synthesis using the Boc-chemistry, cleaved from the resin support, and purified by reverse-phase HPLC to homogeneity. The alkyl aldehyde in the scaffolding was generated by oxidizing the 1,2-amino ethanol moiety of the N-terminal Ser on the scaffolding, [$Ser_8Lys_4Lys_2$-Lys-β-Ala ($Ser_8$-MAP)], with sodium periodate at pH 7 to yield a glyoxylyl derivative of $(HCO)_8$-MAP in nearly quantitative yield.

The monomer containing the weak base to be reacted with the aldehyde contained the 1,2-amino thiol group of cysteine at the N-terminal of a purified and unprotected 24-amino acid residue peptide, CI-24 (CNYNKRKRIHIGPGRAFYTTKNII SEQ ID NO:10), obtained by the solid phase method. Rusche, J. R., Javaherian, K., McDanal, Pedro, J., Lynn, D. L., Grimaila, R., Langlois, A., Gallo, R. C., Arthur, L. O., Fischinger, P. J., Bolognesi, D. P., Putney, S. D. and Matthews, T. J. (1988) *Proc. Natl. Acad. Aci. U.S.A.* 85, 3198–3202; Goudsmit, J., Debouck, C., Meloen, R. H., Smith, L., Bakker, M., Asher, D. M., Wolff, A. F., Gibbs Jr, C. J. and Gajdusek, D. C. (1988) *Proc. Natl. Acad. Sci. U.S.A.* 85, 4478–4482; Javaherian, K., Langlois, A. J., McDanal, C., Ross, K. L., Eckler, L. I., Jellis, C. L., Profy, A. T., Rusche, J. R., Bolognesi, D. P., Putney, S. D. and Matthews, T. J. (1989) *Proc. Natl. Acad. Sci. U.S.A.* 86, 6768–72; Devash, Y., Calvelli, T. A., Wood, D. G., Reagan, K. J. and Rubinstein, A. (1990) *Proc. Natl. Acad. Sci. U.S.A.* 87, 3445–49; Takahashi, H., Cohen, J., Hosmalin, A., Cease, K. B., Houghten, R., Cornette, J. L., DeLisi, C., Moss, B., Germain, R. N. and Berzofsky, J. A. (1988) *Proc. Natl. Acad. Sci. U.S.A.* 85, 3105–3109. Laser-desorption-mass spectrometric analysis of CI-24 (calcd) 2864.4, (found) 2868 and amino acid analyses of these compounds agreed with the calculated values.

The thiazolidine ligation reaction was adequately performed at pH 4.2 in $H_2O$. However, the use of an organic cosolvent and elevated temperature (37° C.) provided consistently better results than in $H_2O$ alone because they enhanced the rate of formation and prevented various intermediate dendrimers aggregating or precipitating during the course of the reaction. The best combination was found to be N-methylpyrrolidinone (NMP):$H_2O$, (1:1, v/v). Other organic cosolvents such as DMSO or DMF were not suitable. DMSO was shown to be a mild oxidant that led to disulfide formation of cysteinyl containing peptides and DMF led to formylation (M+28) of the unprotected peptide as shown by MS analysis of products containing M+28 peaks. Using the optimized NMP:$H_2O$ mixture, the less-hindered tetra- and pentameric MAPs were completed in <2 hours, while the hexa- and heptameric MAP required 7 and 30 hours respectively. The more hindered, fully substituted octameric MAP was found to give 82% in 67 hours. (For a schematic of this reaction see FIG. 7).

The procedure used for thiazolidine ring formation was as follows. All solutions used for this reaction were deaerated and purged with argon, and EDTA (0.02 M) was added to prevent disulfide oxidation. Peptide CI-24 SEQ ID NO:10 (7.18 mg) dissolved in 0.02 M NaOAc (0.13 mL) containing 0.02 M EDTA to give a 20 mM solution at pH 4 were added to a 11.6 mM solution of MAP core (0.166 mg) in $H_2O$ (0.01 ml) and diluted with an equal volume of NMP:HOAc (9:1, v/v) to give a final volume of NMP:$H_2O$ at 1:1. The reaction was performed at 37° C. for 80 hours.

EXAMPLE 9

A comparison of different ligation methods using thiazolidine, hydrazone, and oxime and a 20-residue antigenic peptide was performed (See FIG. 8 for a schematic of reactions).

A 20-amino acid-residue antigenic peptide derived from the surface protein of feline leukemia virus, VA-20 (VMEYKARRKRAAIHVMLALA SEQ ID NO:8), containing a weak base such as aminooxy acetyl, mono-hydrazide succinyl, or cysteine attached at the amino terminus was synthesized by stepwise solid phase peptide synthesis employing Fmoc-chemistry on p-benzyloxybenzyl alcohol resin (Wang-resin). After completing the peptide sequence assembly, the functional residues for ligation, aminooxyacetyl, mono-hydrazide succinyl, and cysteinyl were introduced respectively onto the peptide N- termini. Cleavage of the peptides was carried out with TFA11 and crude peptide products were purified by RP-HPLC. The purified peptides were characterized by amino acid analysis and Matrix Assisted Laser Desorption Ionization-MS (MALDI-MS).

Ligation of peptides with MAP core matrix (See FIG. 9 for a schematic of synthesis of matrix.): Typically, the ligation reaction was performed in aqueous condition and this was used as the starting point for later optimization. This "standard condition" used 2.5 molar equivalents of unprotected peptide with concentrations of 1.25 mM and 0.125 mM of MAP core in the aqueous medium buffered by 0.1 M Na/HOAc. The pH ranges of the reaction solution for each type of ligation were selected according to prior knowledge of the reaction mechanism. The pH 4.7, 5.2, and 4.5, therefore, were used for oxime, hydrazone, and thiazolidine ligation, respectively. The reaction process was followed by HPLC analysis (FIGS. 10–12). In FIGS. 10–12, all the peptide monomers were marked as peak 1. In oxime and hydrazone ligation reactions, ligation intermediates with one copy of peptide attached on the MAP core were not observed and only MAP core matrix with two (peak 2), three (peak 3), and four (peak 4) copies of peptide were observed during the course of the reaction. In thiazolidine ligation (FIG. 12) only products containing three (peak 3) and four copies of peptide (peak 4) were observed after mixing the two components. The minor peak marked with 2' is a dimer of the peptide linked with a disulfide bond. In the thiazolidine formation, 0.01 M of EDTA was added to the reaction mixture with argon purging through the reaction solution to suppress disulfide formation. Under such a reaction condition, less than 2% of total starting cysteinyl- peptide was oxidized to disulfide dimer (FIG. 12, peak 2'). This result shows a significant advantage of ligation under such an acidic condition over other conjugations employing thiol functionality under neutral or basic conditions, which have disulfide formation as one of the major side reactions.

Under an acidic condition, all three reactions produced clean ligation products in good yield, which fulfilled the objective of overcoming side reactions that occur in basic medium. The final ligation products as well as the ligation intermediates were characterized by MALDI-MS (FIG. 13). Amino acid analysis results of the final ligation products also gave the expected composition. The results of thiazolidine (pH 4.5), oxime (pH 4.7), and hydrazone (pH 5.2) formation in aqueous as well as water-miscible organic solvent-water mixture solution are summarized in Tables 3–5 below.

TABLE 3

Rate of VA-20-MAP Formation Through Oxime Ligation

| Reaction | pH | | | | 50% Organic Solvents (ph 5.7) | | | 37° C. | | |
|---|---|---|---|---|---|---|---|---|---|---|
| | | | | | | | | $H_2O$ | 50% DMSO | |
| Condition | 4.7[3] | 4.2 | 5.2 | 5.7 | $CH_3CN$ | DMF | DMSO | pH 4.7 | pH 4.7 | pH 5.7 |
| Time (h)[1] | 40 | 44 | 38 | 32 | 35 | 18 | 8 | 23 | 16 | 4.5 |
| Rel. Rate[2] | 1.0 | 0.9 | 1.4 | 1.6 | 1.5 | 2.9 | 6.5 | 2.3 | 3.3 | 12 |

[1]time for reaching 90% of completion of ligation reached based on HPLC analysis
[2]Rel. Rate: relative reaction rate based on standard condition
[3]defined as standard condition.

TABLE 4

Rate of VA-20-MAP Ligation Through Hydrazone Ligation

| Reaction | pH | | | 50% Organic Solvents (pH 5.7) | | | 37° C. | | |
|---|---|---|---|---|---|---|---|---|---|
| | | | | | | | $H_2O$ | 50% DMSO | |
| Condition | 5.2[3] | 4.7 | 5.7 | $CH_3CN$ | DMF | DMSO | pH 5.2 | pH 5.2 | pH 5.7 |
| Time (h)[1] | 40 | 44 | 34 | 76 | 16 | 2 | 26 | 8 | 1.5 |
| Rel. Rate[2] | 1.0 | 0.9 | 1.2 | 0.5 | 2.5 | 20 | 1.5 | 5 | 27 |

[1]time for reaching 90% of completion of ligation reached based on HPLC analysis
[2]Rel. Rate: relative reaction rate based on standard condition
[3]defined as standard condition.

TABLE 5

Rate of VA-20-MAP Ligation Through Hydrazone Ligation

| Reaction Condition | pH | | | 50% Organic Solvents (pH 4.5) | | | 37° C. | |
|---|---|---|---|---|---|---|---|---|
| | | | | | | | $H_2O$ | 50% DMF |
| | 4.5[3] | 4.0 | 5.0 | $CH_3CN$ | TFE | DMF | pH 4.5 | pH 4.5 |
| Time (h)[1] | 24 | 30 | 16 | 18 | 30 | 5 | 8 | 2 |
| Rel. Rate[2] | 1.0 | 0.8 | 1.5 | 1.3 | 0.8 | 4.8 | 3 | 12 |

[1]time for reaching 90% of completion of ligation reached based on HPLC analysis
[2]Rel. Rate: relative reaction rate based on standard condition
[3]defined at standard condition.

In general, the ligation reaction rates were increased by manipulating pH, temperature, and organic cosolvents. The optimal reaction pH range for oxime and hydrazone ligations is around 5.0 and 4.5 for thiazolidine ligation. At 37° C. the reaction led a 2–3 fold of rate increase. Addition of organic cosolvents further accelerates the reaction rates. DMSO is the most useful cosolvent for oxime and hydrazone formation, while DMF is best for thiazolidine formation. When reactions were performed at 37° C. in media containing the appropriate organic solvents, a greater than 10 fold rate increases were observed for all three reactions. Ligation reactions were completed within 6 hours, compared to 1–3 days under unoptimized conditions. The thiazolidine ligation showed the fastest reaction rate among the three types of reactions tested and its ligation product was stable in a wide pH range of 3–9. The side reaction of thiol group oxidation can be suppressed by carrying out ligation at a pH as low as 4.5 and by adding EDTA to the reaction medium.

The facile reaction rate and stable product make thiazolidine ligation the most attractive ligation reaction for the synthesis of large peptide dendrimers.

Peptide syntheses were performed on a CSBIO-536 automated synthesizer using CSBIO software. Purification of peptides was performed on a Waters instrument equipped with Vydac C18 reverse phase columns (size 25×2.2 cm i.d. and 25×1 cm i.d.). Analytical HPLC was performed on Shimadzu instruments including SCL-1OA system controller, two LC-1OAS pumps, SIL-1OA auto injector, SPC-1OA UV-VIS detector, and CR501 integrator. The analyses were carried out on a Vydac C18 reverse phase column (25×0.46 cm i.d.) at 1.0 ml/minutes monitoring at 225 nm. Eluents used were: A 0.046% TFA in water and B 0.039% TFA in 60% acetonitrile. The gradients used in the analyses are listed as follows: 1. oxime ligation: 0–1 minutes, 38% B, 1–21 minutes, linear gradient from 38–60%; 2. hydrazone ligation: 0–1 minutes, 38% B, 1–21 minutes, linear gradient from 38–64%;3. thiazolidine ligation: 0–1 minutes, 35% B, 1–21 minutes, linear gradient from 35–60% For amino acid analysis a fluorescence monitor was used for detection. The QPA/2-mercaptoethanol method was applied for amino acid analysis.[17] The molecular weight of the peptides was determined on a Kratos MALDI-MS III instrument.

Peptide VA20 with the sequence of VMEYKARRKRAAIHVMLALA SEQ ID NO:8 was synthesized on the machine using the Fmoc/tBu strategy. p-Benzyloxybenzyl alcohol resin (Wang-resin) was used for synthesis. Coupling was accomplished by DCC/HOBT method with 2.5 equivalents of amino acids, and the Fmoc group was deprotected by 20% piperidine in DMF. The protected weak bases for ligation were introduced onto peptide through coupling 3 equivalents of Boc-$NHOCH_2COOH$, BOC-$NHNHCOCH_2CH_2COOH$, or Fmoc-Cys(Trt)-OH with BOP reagent. Final cleavage of peptides from the resin was performed with 90% TFA/6% thioanisole/3% ethanedithiol/ 1% anisole (50 ml/(g resin) for 3 hours. The resin was removed by filtration and the filtrates were concentrated in vacuo.

After peptide products were precipitated with dry ether, they were filtered and further washed with dry ether. The precipitates were taken up in 100 ml of 10% acetic acid. Insoluble residues were removed by centrifugation. After lyophilization, these crude products were purified by RP-HPLC. The purified peptides were characterized by MALDI-MS and amino acid analysis. MALDI-MS: $NH_2OCH_2CO$-VA20: 2402±2.4 (Calcd. 2402); $NH_2NH(CH_2)_2CO$-VA20: 2444±2.4 (Calcd. 2443); Cys-VA20: 2431±2.4 (Calcd. 2432)

Amino acid analysis gave expected data for all peptides. Boc-Lys(Boc)-Ala-$OCH_3$ (1). 1.40 g (10 mM) of H-Ala-$OCH_3HCl$ were suspended in a solution of 3.46 g (10 mM) of Boc-Lys(Boc)-OH in 12 ml of DMF and 6 ml of DCM. The mixture was cooled at 0° C. and 4.42 g (10 mM) of BOP and 2.84 g of DIEA (22 mM) were added. The reaction mixture was stirred at 0° C. for 30 minutes and then at room temperature for 20 hours DCM and DMF were then removed in vacuo, the residue was taken up in 100 ml of ethyl acetate and the ethyl acetate phase was washed with saturated NaCl (2×15 ml), 2% $NaHSO_4$ (2×15 ml), 5% $NaHCO_3$ (3×15 ml) and water (3×15 ml). The organic phase was dried over anhydrous $Na_2SO_4$ and then concentrated to dryness. After recrystallization from ethyl acetate/hexanes, totally 4.37 g of dipeptide (1) were obtained (yield: 91.6%). MALDI-MS: 480.7±0.4 (Calcd. for $M+H^+$480.6) elemental analysis: $C_{24}H_{37}N_3O_7$ (479.57) Found: C 60.31, H 7.92, N 8.48; Calcd: C 60.11, H 7.78, N 8.76 Boc-Lys(Boc)-Lys [Boc-Lys(Boc)]-Ala-$OCH_3$ (2). 0.96 g (2 MM) of 1 were dissolved in 20 ml of 50% TFA/DCM. After stirring at room temperature for 20 minutes TFA and DCM were removed in vacuo. The residue was washed with dry ether (4×10 ml) and then dissolved in 20 ml of DMF. After the addition of 1.55 g (12 mM) of DIEA, 1.44 g (4.2 mM) of Boc-Lys(Boc)-OH, the mixture was cooled at 0° C., and 1.86 g (4.2 mM) of BOP were added to this solution in 0.5 minutes The mixture was stirred at 0° C. for 30 minutes, then at room temperature for 24 hours. The peptide was worked up as described in the preparation of dipeptide 1 preparation and final 1.65 g of title product were obtained (yield: 92.6%). MALDI-MS: 910.4±0.9 (Calcd. for $M+Na^+$911.1) elemental analysis: $C_{42}H_{77}N_7O_{13}$ (888.11) Found: C 57.01, H 8.88, N 10.68; Calcd: C 56.80, H 8.74, N 11.04 {[$(CH_3O)_2CHCO]_2$-Lys}$_2$-Lys-Ala-$OCH_3$ (3).

To the solution of 671 mg (5 mM) of $(CH_3O)_2CHCOCH_3$ in 5 ml of methanol 10.5 ml of 0.5 N NaOH were added. The reaction was completed at in 2 hours by TLC monitoring. Methanol was removed in vacuo and the remaining aqueous solution was diluted to 25 ml with water. The solution was extracted with ethyl acetate (3×8 ml). The aqueous solution was concentrated to 10 ml and then lyophilized to dryness.

0.89 g (1 mM) of 2 were dissolved in 20 ml of 50% TFA/DCM and the solution was stirred at room temperature for 20 minutes After the removal of TFA and DCM, the residue was washed with dry ether (3×10 ml) and then dissolved in 10 ml of DMF. To this solution the powder obtained in A (5 mM), 1.86 g (4.2 mM) of BOP and 0.65 g (5 mM) of DIEA were added. After stirring the reaction mixture for 20 hours at room temperature, DMF was removed in vacuo. To the residue 10 ml of ethyl acetate were added and the solution was allowed to stand at 4° C. overnight. The precipitate was collected by filtration. The mother liquor was concentrated to dryness and then dissolved in 3 ml of water. After the addition of 4 drop of acetic acid, the precipitate (HOBt) was filtered off. The filtrate was concentrated to dryness. After washing the residue with dry ether, white powder was obtained and which was combined with the precipitate obtained from ethyl acetate above. The combined product was purified on a silica gel (40 g, 130–270 mesh, 60 Å, Aldrich) column using $CHCl_3$:EtOAC:MeOH=60:25:15 as eluent. 680 mg of product were obtained.

Yield: 75.9%. MALDI-MS: 919.2±0.9 (Calcd. for $M+Na^+$ 918.99) elemental analysis: $C_{38}H_{69}N_7O_{17}$ (896.00) Found: C 50.82, H 8.10, N 10.77; Calcd: C 50.94, H 7.76, N 10.94

CHOCO-Lys(CHOCO)-Lys(CHOCO-Lys(CHOCO))-Ala-OH (4) was synthesized as follows. To the solution of 134.4 mg (0.15 mM) of peptide 3 in 10 ml water and 2 ml methanol, 1.8 ml of 0.1 N NaOH were added. After stirring at room temperature for 2 hours, the hydrolysis reaction was completed according to TLC analysis. Methanol was removed in vacuo and the pH of solution was brought to 7.5 by adding 0.25 ml of 0.1 N HCl. After lyophilization, the white powder was dissolved in 1.5 ml of water. 500 ml (50 μmol) of this solution were taken out and to this solution 5 ml of conc. HCl were added. After stirring at room temperature for 3 minutes, the solution was concentrated to dryness in vacuo on a water bath of 35° C. The residue was purified by RP-HPLC. After lyophilization 22.5 mg of pure aldehyde-MAP core were obtained. Yield 64.5%. MALDI-MS: 699.0 (Calcd. 698.7)

The synthesis of MAPs through oxime, hydrazone, and thiazolidine ligation was performed as follows. All peptides were dissolved in water to give a 5 mM stock solution. The aldehyde-MAP core was dissolved in water as 5 mM stock solution.

For different ligation experiments in aqueous media, 50 μl of peptide stock solution were mixed with 50 μl of water, 100 μl of 0.2 M Na/HOAc buffer, 5 μl of aldehyde-MAP core solution. The final concentration was 1.25 mM for peptide and 0.125 mM for aldehyde-MAP core.

For ligation in 50% organic cosolvent, 50 μl of peptide stock solution were mixed with 50 μl 0.4 M Na/HOAc buffer, 100 μl of individual organic solvent, 5 μl of aldehyde-MAP core solution. The final concentration was 1.25 mM for peptide and 0.125 mM for aldehyde MAP core.

For ligation using 5 equivalents of peptide, 100 μl of peptide stock solution were mixed with 100 μl 0.2 M Na/HOAc buffer, 5 μl of aldehyde-MAP core solution.

The final concentration was 2.5 mM for peptide and 0.125 mM for aldehyde-MAP core.

All the reactions were followed by RP-HPLC analysis: 5 μl of reaction solution were taken at various time intervals and analyzed through RP-HPLC. The calculated rates of production formation are summarized in Tables 2–4.

The ligation products were collected after separation by HPLC. Amino acid analysis of the products gave satisfactory results. MALDI-MS of final ligation products: VA20-Hdz-MAP: 10233±10 (Calcd. 10230); VA20-Hdz-MAP: 10393±10 (Calcd. 10395); VA20-Thz-MAP: 10347±10 (Calcd. 10351). The amino acid analyses of the ligation products also gave the expected compositions.

EXAMPLE 10

The general approach is to exploit the selective reaction between a weak base and an aldehyde to form a stable conjugated phenyl hydrazone or ring compounds (FIG. 14). In this reaction, a weak base is distinguished from strong bases such as side chain and -amines or the guanidino group of Arg in totally unprotected peptide fragments to serve as the only nucleophile reactive towards the aldehyde function under acidic conditions. The aldehyde group as an electrophile is distinguished from other functional groups in the peptide and is the only reactive moiety with the weak base in acidic pH. In this example, a weak base such as the 1,2-amino thiol of cysteine or 4-hydrazino benzoyl was placed at the N-terminal of a peptide fragment which was synthesized by stepwise solid phase method. The peptide with the N-terminal weak base was deprotected from the resin with all side chain protecting groups removed. The purified unprotected peptide was then reacted in solution with the unprotected MAP core matrix containing multiple copies of aldehyde functions (a-oxoacyl), generated from the periodate oxidation of N-terminal serine of the $(Ser)_n$-Lysyl-β-Ala scaffolding.

The core matrix containing either two or three levels of branched lysines and four or eight amino groups was synthesized by stepwise solid phase method using Fmoc-chemistry on a Wang resin (FIG. 15). Both $(Ser)_4$-$(Lys)_2$-Lys-βAla ($Ser_4$-MAP) and $(Ser)_8$-$(Lys)_4$-$(Lys)_2$-Lys-βAla ($Ser_8$-MAP) were obtained by TFA cleavage from the peptide resin. Because only three and four coupling steps, respectively, were involved in these syntheses, both products were obtained in high purity (>95%) and were used without further purification. The same compounds could also be achieved by Boc-chemistry. To functionalize the MAP core matrix with reactive aldehyde groups, the lysinyl-resin was capped with Fmoc-Ser(t-Bu) to give an 2-amino alcohol moiety which was transformed by periodate oxidation to generate an α-oxoacyl group. Oxidation of Ser-MAP to CHO-MAP containing four or eight copies of α-oxoacyl groups was achieved using two-molar excess of sodium meta-periodate in aqueous buffer at pH 7 for 5 minutes The reaction was quenched with 4 fold excess of ethylene glycol. No side products were observed by C18 RP-HPLC. Because formaldehyde was generated during the quenching as well as from the reaction, the (CHO)-MAP forms were purified by C18 RP-HPLC. Both forms of Ser-MAP and CHO-MAP were characterized by laser desorption mass spectrometric (LD-MS) analysis to give the expected MW. The aldehydic MAP cores were used immediately for the conjugation reaction.

Two unprotected peptide fragments were selected for the conjugation reactions. The first peptide fragment, CA-16 ($CNYNKRKRIHIPGPRA-NH_2$ SEQ ID NO:13), contains 16 residues and is rich in basic amino acids. This peptide is the neutralizing epitope and part of the third variable region (V3 loop) of gp120 of human immunodeficient virus, MN strain. Rusche, J. R., Javaherian, K., McDanal, Pedro, J., Lynn, D. L., Grimaila, R., Langlois, A., Gallo, R. C., Arthur, L. O., Fischinger, P. J., Bolognesi, D. P., Putney, S. D. and Matthews, T. J. (1988) *Proc. Natl. Acad. Aci. U.S.A.* 85, 3198–3202; Goudsmit, J., Debouck, C., Meloen, R. H., Smith, L., Bakker, M., Asher, D. M., Wolff, A. F., Gibbs Jr, C. J. and Gajdusek, D. C. (1988) *Proc. Natl. Acad. Sci. U.S.A.* 85, 44784482; Javaherian, K., Langlois, A. J., McDanal, C., Ross, K. L., Eckler, L. I., Jellis, C. L., Profy, A. T., Ruscie, J. R., Bolognesi, D. P., Putney, S. D. and Matthews, T. J. (1989) *Proc. Natl. Acad. Sci. U.S.A.* 86, 6768–72; Devash, Y., Calvelli, T. A., Wood, D. G., Reagan, K. J. and Rubinstein, A. (1990) *Proc. Natl. Acad. Sci. U.S.A.* 87, 3445–49; Takahashi, H., Cohen, J., Hosmalin, A., Cease, K. B., Houghten, R., Cornette, J. L., DeLisi, C., Moss, B., Germain, R. N. and Berzofsky, J. A. (1988) *Proc. Natl. Acad. Sci. U.S.A.* 85, 3105–3109. A cysteine was placed at the N-terminal and was ideally suited for the ligation to the aldehyde groups of the core matrix in the formation of a 5-member thiazolidine ring. The second peptide fragment, SR-10 (SSQFQIHGPR SEQ ID NO:14) contains 10 residues and is an autoimmune epitope from the ZP3 glycoprotein. Rusche, J. R., Javaherian, K., McDanal, Pedro, J., Lynn, D. L., Grimaila, R., Langlois, A., Gallo, R. C., Arthur, L. O., Fischinger, P. J., Bolognesi, D. P., Putney, S. D. and Matthews, T. J. (1988) *Proc. Natl. Acad. Aci. U.S.A.* 85, 3198–3202; Goudsmit, J., Debouck, C., Meloen, R. H., Smith, L., Bakker, M., Asher, D. M., Wolff, A. F., Gibbs Jr, C. J. and Gajdusek, D. C. (1988) *Proc. Natl. Acad. Sci. U.S.A.* 85, 4478–4482; Javaherian, K., Langlois, A. J., McDanal, C., Ross, K. L., Eckler, L. I., Jellis, C. L., Profy, A. T., Rusche, J. R., Bolognesi, D. P., Putney, S. D. and Matthews, T. J. (1989) *Proc. Natl. Acad. Sci. U.S.A.* 86, 6768–72; Devash, Y., Calvelli, T. A., Wood, D. G., Reagan, K. J. and Rubinstein, A. (1990) *Proc. Natl. Acad. Sci. U.S.A.* 87, 344549; Takahashi, H., Cohen, J., Hosmalin, A., Cease, K. B., Houghten, R., Cornette, J. L., DeLisi, C., Moss, B., Germain, R. N. and Berzofsky, J. A. (1988) *Proc. Natl. Acad. Sci. U.S.A.* 85, 3105–3109. It was prepared with a phenyl hydrazine group at the amino terminus so it could form hydrazone linkages with the CHO-MAP core. Both fragments, CA-16 and hydrazinobenzoyl(Hob)-SR-10 were prepared without difficulty by solid-phase method using Boc-chemistry and purified bv C18 RP-HPLC to homogeneous products (FIGS. 16 and 17). The phenyl hydrazine group was introduced to SR-10 through an amide linkage to the amino group of the peptide with 4-Boc-hydrazinobenzoic acid using DCC/HOBt at the final step of the synthesis. The Hob group was found to be stable to the usual cleavage Conditions of using TFA (Fmoc) chemistry and HF (Bio chemistry).

All solvents used for conjugation reactions were deaerated and purged with argon. DMF, DCM (both biotechnology grade), acetonitrile and MeOH (HPLC-grade) were obtained from Fisher Scientific; DCC, p-cresol and piperidine (Aldrich Chem.); and TFA (Halocarbon). Boc- and Fmoc-amino acids were purchased from Bachem (Torrance, Calif.). All other chemicals were the purest grade available. All peptides and conjugate products were analyzed and purified on Shimadzu and Waters HPLCs . Mass spectrometric analysis was determined by matrix assisted laser-desorption mass-spectrometry (Kratos).

CA-16 carboxamide ($CNTNKRKRIHIPGPRA-NH_2$ SEQ ID NO:15) was synthesized by the solid-phase using the Boc/Bzl strategy. The synthesis was started from the 4-methybenzhydrylamine-resin (0.54 mmol/g). Side chain protecting group were: Arg(Tos), Cys(4-MeBzl), His(Dnp), Lys(CIZ), Ser(Bzl), Thr(Bzl) and Tyr(BrZ). All amino acids were protected with Boc on the Np-terminus. All couplings were performed in DCC except for Boc-Arg and Boc-Asn, which were carried out in HBTU and DIEA. After synthesis, the protected peptide resin was treated with 10% thiophenol in DMF (v/v) for totally 24 hours to remove the $N^{im}$-Dnp protecting group on His. The dried peptide-resin was deprotected and cleaved by High HF (p-cresol) for 1.5 hours at 0° C. After cleavage, the crude peptide was purified by preparative C18-RP HPLC. The purified peptide was analyzed by matrix assisted laser-desorption mass-spectrometry (LDMS); [CA-16] (cal/found) (1884/1884).

Solid phase peptide synthesis of SR-10 (SSQFQIHGPR SEQ ID NO:14) was performed on a Pam resin (0.41 mmol/g). The procedure was the same as described above. At the completion of the synthesis, the resin was coupled with 4 molar excess of 4-Boc-NHNH-$C_6H_4$-$CO_2H$ via DCC/HOBt in DMF/DCM (1:1, v/v). LDMS analysis gave calcd/found (1290.5/1291).

$Ser_4$-$Lys_2$-Lys-BAla and $Ser_8$-$Lys_4$-$Lys_2$-Lys-βAla were synthesized by a stepwise solid phase method using the Fmoc/t-Bu strategy on a Wang-resin (0.5 mmol/g). Attachment of Fmoc-βAla (6 equiv) to the resin was performed in DCC (3 equiv) and 10% DMAP (0.1 mM) in DMF/DCM (1:1, v/v). Synthesis of and 3 levels of the lysines were achieved using 3 molar excess of Fmoc-Lys(Fmoc) and DCC in DMF/DCM (1:1, v/v). After Fmoc deprotection, Fmoc-Ser(t-Bu) was coupled to the lysine containing MAP core-matrix via DCC in DMF/DCM. Both $Ser_4$-$Lys_2$-Lys-BAla and $Ser_8$-$Lys_4$-$Lys_2$-Lys-βAla were cleaved from the resin by TFA and lyophilized for immediate use without purification. Conversion of the Ser-MAP to glyoxyl-MAP was achieved by oxidation with meta-periodate (46.8 μmol, 10 mg) and $Ser_n$-MAP (n=4, 6.1 μmol, 5 mg,; n=8, 2.97 μmol, 5 mg) in 0.01 M sodium phosphate-buffer, pH 7 (n=4, 300 μl; n=8, 210 μl). After the reaction was mixed for 5 minutes at room temperature, it was quenched by adding ethylene glycol (93.5 μmol, 5.3 μl) to remove the excess of sodium meta-periodate. The mixture was purified by C18-RP HPLC with a 30-min linear gradient of 0–60% buffer B. Buffer A contained 100% water, 0.045% TFA and Buffer B contained 60% $CH_3CN$, 0.039% TFA. Both MAP core matrixes were used immediately for the conjugation reaction after HPLC purification. LDMS analysis gave the expected molecular weights, ($Ser_4$-MAP, calcd/found (821/822), $(HCO\text{-}CO)_4$-MAP, calcd/found (697.7/698), $Ser_8$-MAP, calcd/found (1682.5/1683)5 $(HCO\text{-}CO)_8$-MAP, calcd/found (1434.511436).

The unprotected peptide fragment CA-16 and (CHO)4-MAP were assembled to form a tetrameric branched peptide in aqueous buffer at pH 5 using a 4 molar equivalents of peptide for each oxoacyl site. To investigate the optimal condition for the formation of the 5-member thiazolidine ring between t)-oxoacyl group at the MAP core and N-terminal cysteine, the effects of organic co-solvent, temperature, and antioxidants such as EDTA (ethylenediaminetetraacetic acid) to prevent disulfide formation were examined, and the results are given in Table 6 below:

TABLE 6

Effect of Antioxidant, Organic Solvent and Temperature on the Thiazolidine Ring on the Ligation of an Unprotected Peptide CA-16 $(CHHO)_4$-MAP

| Reaction Conditions[1] | Conc. Peptide (mM) | Time (h) for 50% completion 22° C. | 37° C. | 50° C. |
|---|---|---|---|---|
| $H_2O$ | 4.8 | 15 | — | — |
| $H_2O$ + EDTA | 4.8 | 10.7 | 5.8 | 2 |
| $H_2O$ + EDTA | 8.0 | 6.3 | 5 | 2.5 |
| $H_2O$/DMF (4:6, v/v) | 4.8 | 4.5 | 2 | 1.6 |

[1]All the reactions were performed at pH 4 using 4 mol equiv. of peptide (CA-16) for each α-oxoacyl group on $(CHO)_4$-MAP and the pseudo first order rates were used.

Since relatively large excess of monomers were used, the pseudo first order rate was evaluated based on the formation of 50% of the conjugation product monitored by C8 RP-HPLC. In these experiments, all samples were deaerated and saturated with argon to exclude oxygen in the solution. However, it was found that this condition was insufficient to prevent disulfide oxidation of the peptide CA-16 that consumed the starting material and lowered the yield. The use of an anti-oxidant or chelating agent such as EDTA, which removed metal cations in the aqueous solution that catalyzed disulfide oxidation, was studied. EDTA (0.8 mM) was sufficient to reduce disulfide formation of CA16 to <5% and increased the to of the rate formation from 15 to 10.7 hours. Thus, EDTA was used in all subsequent experiments to minimize disulfide formation.

The rate of thiazolidine ring formation was dependent on three factors. The most significant appeared to be the organic co-solvent which gave a rate increase of about 3 fold when 60% of DMF was present at 22° C. As expected, increased temperature from 22° C. to 37° C. enhanced the rate about 2 fold in $H_2O$ or 60% DMF, and nearly 5 and 3 fold at 50° C., respectively. Finally, the increase in concentration from 4.8 M to 8 M had slight beneficial effects. The combination of organic co-solvent and elevated temperature provided not only rate acceleration but also reduced the danger of aggregation that leads to precipitation.

Peptide CA-16 was also conjugated to the CHO-MAP core containing eight aldehyde groups to give a highly compact and dense octameric peptide dendrimer. This conjugation reaction was performed in aqueous buffer containing EDTA at 37° C. and was completed within 12 hours with only one major peak (FIG. 16) and a side product <5% from the oxidation of CA-16 to CA-16 disulfide dimer was observed. The products obtained from conjugation of CA-16 to $(CHO)_4$-MAP and $(CHO)_8$-MAP to give the tetrameric and octameric branched dendrimers were analyzed and gave the correct MW and amino acid analysis as shown in Table 7 below:

TABLE 7

Analysis of Peptide Fragments and Ligation Products by Matrix-Assisted Laser Desorption Mass Spectrometry

| Compound | MW from $(M + 1)^+$ | Calcd. Values | Δ |
|---|---|---|---|
| $(Ser)_4$-MAP | 822 | 821 | +1.0 |
| $(Ser)_8$-MAP | 1,683 | 1,682.5 | +0.5 |
| Hob-SR10 | 1,291 | 1,290.5 | +0.5 |
| CA16 | 1,884 | 1,884 | 0.0 |
| $(SR10)_4$-Hab-MAP | 5,789.1 | 5,788 | +1.1 |
| $(SR10)_3$-Hab-MAP | 11,615 | 11,614.5 | +0.5 |
| $(NA15)_4$-Thz-MAP | 8,162 | 8,160.7 | +1.3 |
| $(NA15)_8$-Thz-MAP | 16,363 | 16,362.5 | +0.5 |

Furthermore, despite their high MWs, they gave a single peak in RP-HPLC. These results show that the reaction is highly specific and that no evidence of side reaction between the α-oxoacyl group with the side chain nucleophiles can be found.

Conjugated phenyl hydrazine has a pKa of about 4.5 and forms a stableconjugated hydrazone with an alkyl aldehyde. Thus, in this approach, the unprotected peptide Hob-SR-10 was assembled on the $(CHO)_4$-MAP core matrix at pH 5 to form the tetrameric peptide dendrimer. The hydrazone formation in aqueous solution between Hob-SR-10 and $(CHO)_4$-MAP was rapid and selective and dependent on the stoichiometric ratio of peptide to each aldehyde group. With an equal molar ratio of peptide and p-oxoacyl group, the reaction was completed in 5 hours but accelerated to 1 hour and 10 minutes, respectively, when the stoichiometric ratio of peptide and aldehyde was increased to 1.5 and 2. The progress of the reaction was conveniently monitored by analytical RP-HPLC. Because phenyl hydrazine and the conjugation product, phenyl hydrazone, differ in their absorption maximum by 70 nm, it was monitored by uv spectrometry (FIG. 18). To achieve eight copies of SR1O on the MAP core matrix, the reaction was performed in DMF:$H_2O$ (1:1, v/v) to prevent precipitation of the intermediates to give the octameric SR-10 MAP. This reaction was monitored by RP-HPLC and only one single product was formed after 12 hours (FIG. 17). The molecular mass for $(SR\text{-}10)_4$-Hab-MAP and $(SR\text{-}10)_8$-Hab-MAP, respectively, was confirmed by LD-MS (Table 7) in addition to amino acid analysis.

Peptide CA-16 (18 μmol, 34 mg) was dissolved in 0.02 M NaOAc buffer containing 0.008M EDTA, pH 5 (2.8 mi) and the (HCOCO)4-MAP solution (1.13 μmol) collected from the HPLC was added. The solution was adjusted to pH 5 with pyridine. The deaerated solution was kept under argon and in dark for 4 hours at 50 pC. The conjugation reaction was monitored by analytical C8-RP HPLC using a linear gradient of solvent B, 2%/min, starting from 0% and with a flow of 1 ml/minutes Buffer A contained 5% $CH_3CH$, 0.045% TFA and Buffer B contained 60% $CH_3CN$, 0.039% TFA. The conjugated product was purified by LDMS semi-preparative HPLC (C18-RP coumn) under isocratic conditions at a flow of 2 ml/minutes The yield of $(peptide)_4$-thiazolidine-MAP was 9.2 mg. The purified peptide-MAP conjugate was analyzed by LDMS, ($(NA-15)_4$-Thz-MAP) calcd/found (8160.5/8162).

Reaction between (HCOCO)s-MAP and CA-16 was achieved using the conditions described above, except that the deaerated solution was kept under argon and in dark overnight at 37° C. The progress of the reaction was monitored by analytical C8-RP HPLC using a linear gradient of solvent B, 0.94%/min, starting from 20% and with a flow of 1 ml/minute Buffer A contained 0% $CH_3CH$, 0.045% TFA and Buffer B contained 60% $CH_3CN$, 0.039% TFA. LDMS analysis gave calcd/found (16362.5/16363).

The $(HCO\text{-}CO)_4$-MAP solution (1.65 μmol) collected from the HPLC was mixed with 4-hydrazino-benzoyl-SR10 (13.2 μmol, 17 mg) and the solution was adjusted to pH 5 with 0.02 M sodium acetate buffer, pH 5. The deaerated solution was kept under argon and in dark for 1 hours at room temperature. The reaction was monitored by analytical C8-RP HPLC using a linear gradient of solvent B, 2%/min, starting from 0% and with a flow of 1 ml/minute The conjugated product was purified by C18-RP HPLC using isocratic conditions. The yield of the $(SR\text{-}10)_4$-Hyz-MAP was 6 mg. The peptide-MAP conjugates was analyzed by LDMS, calcd/found (5788/5789.1).

For the conjugation reaction between 4-hydrazinobenzoyl-SR-10 and $(HCOCO)_8$-MAP, $H_2O$/DMF (1:1), pH 5 was used in 0.02 M sodium acetate buffer. Three mol equivalents of peptide was used for each α-oxoacyl group on $(CHO)_8$-MAP. The reaction was carried out at 37° C. for 12 hours. LDMS analysis gave calcd/found (1 1614.5/11615).

The stability of the 5-member thiazolidine rings and phenyl hydrazone bonds at pH 5–8 were investigated under a wide range of pH in aqueous conditions. The peptide dendrimer derived from ligating CA-16 with the α-oxoacyl MAP core matrix, $(NA\text{-}15)_4$-Thz-MAP, was incubated at 37° C. at pH 5, 6, 7 and 8 and samples were withdrawn at 12 hours intervals for 5 days and analyzed by HPLC. The ligation site of thiazolidine ring in $(NA\text{-}15)_4$-Thz-MAP showed no evidence of significant hydrolysis after 5 days at these pH values and remained as a single symmetrical peak in RP-HPLC (FIG. 16). Similarly when $(SR\text{-}10)_4$-Hab-MAP was incubated at 37 pC at pH 6, 7, 7.4 and 8 and monitored by HPLC over 2 days, the phenyl hydrazone linkage in $(SR\text{-}10)_4$-Hab-MAP remained stable (FIG. 17). Alkyl hydrazone linkages are usually susceptible to hydrolysis and required stabilization by reduction with sodium cyanoborohydride. However, due to the aromatic character in the phenyl hydrazone linkage, it is more resistant to hydrolysis than the alkyl hydrazone and does not require the extra step of reduction for stabilization. These results show that peptide dendrimers with these linkages have substantial stability in aqueous media to be useful at the physiological pHs as drug carriers, vaccines and diagnostic reagents.

Examples 11 to 13 illustrate the application of domain ligation strategy in the site-specific modification of proteins.

Conceptually, site-specific modification of proteins is similar in both principle and practice to the ligation of peptides because proteins are used with many unprotected side chains and the site-specificity of the domain ligation operates. In our examples, the proteins are obtained from the recombinant methods but proteins purified from the natural sources can also be used. Ideally, a protein with an amino terminal cysteine will be useful as a weak base and a protein with an amino terminal serine or threonine can serve as an aldehyde, which can be converted to an aldehyde function by sodium metaperiodate oxidation. This oxidation is relatively selective at pH 7 for the 1,2-aminoethanol such as serine and threonine and is >300 fold faster than the oxidation of 1,2-diol found in the carbohydrates. With the recombinant technology, any proteins can be engineered to contain one of these residues. For naturally isolated proteins lacking in one of these residues, the 1,2- or 1,3-amino thiol moiety can be introduced via a substituted thiolactone (FIG. 19). Unsubstituted thiolactone is too unhindered and gives very poor yield because of self-condensation. The thiolactone forms reversible Schiff base with the aldehyde component that gives nonproductive reaction; but, when the thiolactone reacts with the N-terminal of the protein (some minor reaction with the side chain amine of lysine) the thiol moiety is then liberated to give the ring compound similar to the ring formation of the domain ligation strategy and a stable product.

Example 11 illustrates the principle of domain ligation to modify gp120, which is the surface protein of HIV-1 and a principle target of vaccine development. The site-specific modification by a lipid module such as tripalmitoyl glceryl cysteine (P3C)-Lys(Cys) or Cys-Lys(Pal)-D-Lys(Pal) can be achieved by oxidation of the amino terminal threonine of gp120 to an aldehyde.

Example 12 and 13 illustrate the same principle by modifying any protein to contain an 1,2- or 1,3-amino thiol by reacting with an N-substituted thiolactone in the presence of an aldehyde.

EXAMPLE 11

The site-specific lipidation of gp120 using a lipid module and oxidation of the N-terminal threonine of gp120 to form an aldehyde was performed.

Recombinant derived gp120 of HIV-1, IIIB strain (1 mg) in 0.1 M sodium phosphate buffer at Ph 7 (2 Ml) was treated with 2 molar equivalents of sodium metaperiodate to oxidize the N-terminal threonine to an glyoxyl aldehyde. The reaction was stopped after 5 minutes and quickly dialyzed in the same buffer (1 liter) to remove the oxidant and formaldehyde generated. The oxidized gp120 was then reacted with a biphasic solution (2 ml of methylene chloride-dimethylformaide at 1:1 volume ratio) for 24 hours containing 1.5 equivalent of the following a lipid module containing a cysteine attached to the side chain of an lysinyl peptide: tripalmitoyl glyceryl Cys-Lys-Cys or Cys-Lys(Pal)-D-Lys(Pal)-OH. At the completion of the reaction, the organic phase was evaporated by reduced pressure and the resulting aqueous phase was subjected to purification by high performance gel permeation chromatography to obtain the lipidated gp120.

EXAMPLE 12

The site-specific lipidation of gp120 using a lipid module and a secondary amine thiolactone was performed.

Recombinant derived gp120 (1 mg) in 0. 1 M sodium phosphate buffer at pH 7 (2 ml) was treated with 2 equivalents a substituted thiolactone and a lipid module in a biphasic solution (see Example 11) for 24 hours. At the completion of the reaction the organic phase was evaporated by reduced pressure and the lipidated gp120 was purified by high performance gel permeation chromatography.

EXAMPLE 13

The site-specific pegylation of Interleukin-2 by MeO-PEG-CHO and a secondary amine thiolactone was performed.

The reaction condition and work-up was similar to Example 12.

EXAMPLE 14

General and Site-specific Method for Conjugating Ligand to Synthetic Peptides and Proteins The present Example describes a general and mild method for site-specific conjugation at any position within a synthetic peptide, at the N-terminus of p with N-terminal Ser or Thr, or at the oligosaccharide sites of glycoproteins. This method is based on the weak-base carbonyl chemistry developed by the inventors for the chemoselective domain ligation of proteins (11). The weak base which is the sole nucleophile to react with the carbonyl under acidic conditions is a 1,2-aminothiol found at N-terminal cysteine or site-chain linked cysteine. The carbonyl precursors in the form of N-terminal Ser, Thr or vicinal cis-diols of glycoprotein can be rapidly converted to their aldehyde forms by periodate oxidation. The conjugation is accomplished by the selective reaction of the aldehyde with a 1,2-aminothiol, forming a stable thiazolidine ring under acidic condition as a stable product (FIG. 20). Since the positions to generate the aldehyde can be predetermined, the thiazolidine formation is essentially site-specific. The reaction can be carried out using fully unprotected peptide or protein segments under aqueous conditions. This enables one skilled in the art to modify a great variety of bioactive peptides and proteins in a precisely targeted fashion. The potential of this method is demonstrated by its application to the selective biotinylation of synthetic peptides at N-terminal Ser or Thr and glycoprotein at the carbohydrate sites.

Materials and Methods

Materials. All amino acids and resins were purchased from Bachem, Calif. D(+)-Biotin, N,N'-Carbonyldiimidazole and sodium periodate were from Aldrich Chemical Company. α-Acid glycoprotein was obtained from CALBIOCHEM. Avidin-peroxidase was obtained from Sigma Chemical Co. Silica gel plates with fluorescent indicator were obtained from EM Laboratories, Inc. N-Boc-1,6-diamino-hexanehydrochloride was obtained from Fluka. All solvents of ACS certified or analytical grade or better were obtained from Fisher Scientific Company, and were used without further purification. Water was Milli-Q filtered (Millipore, Inc.).

Analytical RP-HPLC was performed on Shimadzu instruments including a SCL-10A system controller, two LC-10AS pumps, a SIL-10A autoinjector, a SCL-10A UV-VIS detector, and a CR501 integrator. For analytical work, a column 250×4.6 mm i.d. (Vydac 218TP54) was used at a flow rate of 1 ml/min, and effluent monitored at 225 nm. Semi-preparative and preparative purifications of peptides were carried out on a Waters 600 multisolvent delivery system equipped with a Wisp 712 sample processor and a Model 441 UV detector. Two columns, 250×22 mm i. d. and 250×10 mm I. d. (Vydac 218TP152022 and 218TP510), were used at a flow rate of 10 ml/minute and 2.5 ml/minute respectively. Eluents used were (A) 0.046% TFA in water and (B) 0.039% TFA in 60% acetonitrile. The gradient used in the analyses was: 0–1 minute 10% B, 1–31 minutes, linear gradient from 10% to 100% B.

Solid-phase peptide synthesis (12). Peptides with the sequences of TMKA (TA-4) and SSQFQIHGPR (SR-10) SEQ ID NO:14 were assembled by the solid-phase method using Boc chemistry, purified to homogeneity by RP-HPLC and characterized by MALDI-MS and amino acid.analysis. MALDI-MS: TA-4, 450.50 (calc. for M+H+, 450.57): SR-10, 1157.25±0.50 (calc. for M+H+, 1157.26). The peptides gave acceptable amino acid ratios after acid hydrolysis.

Synthesis of biotin-NH—$(CH_2)_6$—NH-Boc. Boc-NH—$(CH_2)_6$—$NH_2$pHCl (1.15 g, 4.4 mM) and NMM (0.49 ml, 4.4 mM) were added to 1.18 g (4 mM) biotinylimidazolide, prepared as described by M. L. Jasiewicz (13), in 20 ml dry DMF. The solution was allowed for stirring overnight at 19° C. The DMF was removed in vacuo and the residue was recrystallized from isopropanol to yield 1.5 g of BC. The product had an Rf value of 0.81 by thin-layer chromatography in chloroform:methanol:acetic acid (85:10:5). *Anal. Calc.* for CHNOS: C, 53.41; H, 9.37; N, 11.32; S, 12.96. Found: C, 53.29; H, 9.37; N, 11.33; S, 12.75. *Synthesis of biotin*-NH—$(CH_2)$6—NH-Cys (BCC). 0.89 g (2 mM) BC was dissolved in 10 ml of 50% TFA/DCM. After 30 minutes, TFA and DCM were evaporated in vacuo and the product precipitated with dry ether. The resultant solid was washed with dry ether (4×10 ml) and then taken up in 10 ml of dry DMF. After the addition of NMM (0.44 ml, 4 mM) and Boc-Cys(Trt)-OH (0.92 g, 2 mM), the mixture was cooled to 4° C. HBTU (0.76 g, 2 mM) was added to this solution. The solution was slowly warmed to room temperature and allowed to stir for an additional 18 hours. The solvent was removed in vacuo and the residue taken up in ethyl acetate (100 ml). The ethyl acetate phase was washed with saturated NaCl solution (2×15 ml), 5% $KHSO_4$ (2×15 ml), 5% $Na_2CO_3$ (3×15 ml), and water (2×15 ml). The organic phase was dried over anhydrous $Na_2SO_4$ and concentrated in vacuo to yield an oily residue which was solidified upon adding n-hexane. The white solid was then treated with 10 ml of TFA/thioanisole (8.5:1.5) for 4 h. After removal of the solvent, the product, BCC, was precipitated with dry ether. The white powder was dissolved with acetic acid and precipitated with dry ether again. After repeating this procedure for several times, the product was taken up in 50 ml water and lyophilized. Yield: 0.67 g. MALDI-MS: 446.5±1 (calc. for M+H+, 446.6). Analytical HPLC showed the product was over 95% pure ($t_R$=13.55)

Periodate Oxidation. (1) TMKA (TA-4). TA-4 (9 mg, 0.02 mM) and methionine (14.9 mg, 0.2 mM) were dissolved in 1 ml of 0.1 M citric acid-0.2 M $Na_2HPO_4$ buffer (pH varied from 4–7) and reacted with 1 ml of 20 mM $NaIO_4$ for 4 minutes at 4° C. The oxidation was stopped by injecting the reaction mixture into a semi-preparative HPLC column and eluting with a linear gradient from 0% to 60% B within 60 minutes. The oxidized product came out directly after injection peak. The product was collected and lyophilized. The oxidation product α-N-glyoxylyl-MKA was eluted as a single peak from an analytical HPLC ($t_R$=8.67 min). MALDI-MS: 405.4 (calc. for M+H+, 404.5), 423.4 (calc. for M+$H^+$+$H_2O$, 423.5).

(2) SSQFQIHGPR (SEQ ID NO:14 SR-10 (1.2 mg, 0.001 mM) was dissolved in 1.5 ml of 0.2 M sodium acetate buffer (pH 5.6) and treated with 40 μl of $NaIO_4$ at 4° C. for 2 minutes. The reaction was terminated by injecting the sample directly into HPLC. The product was separated on the semi-preparative HPLC column using a gradient from 10% to 60% B within 60 minutes and gave a single peak from the analytical HPLC ($t_R$=14.25 min). MALDI-MS: 1126±0.5 (calc. for M+H+, 1126.2), 1143±0.5 (calc. for M+$H^+$+$H_2O$, 1143.2).

(3) Parathyroid hormone (human) Parathyroid hormone (1 mg, 0.24 μM) was dissolved in 1 ml of 0.1 M citric acid-0.2 M $Na_2HPO_4$ buffer containing 1.2 μM methionine (pH 7) and treated with an equivalent NaIO4 (52 μtg, 0.24 μM). The oxidation was allowed to proceed at 4° C. for 4 minutes. The reaction mixture was applied to the semi-preparative HPLC column and eluted using a gradient from 10% to 80% within 60 minutes. Analytical HPLC showed a single peak with $t_R$=21.46 minutes. The purified α-N-glyoxylyl-PTH was characterized by MALDI-MS, giving the expected molecular mass (calc. for M+H+, 4087.7; found, 4087.9±1).

Conjugation of BCC through thiazolidine ring formation. (1) BCC-Thz-MKA Equal volumes (200 μl) of Biotin-C6-Cys (2.25 mM in 0.2 M sodium acetate buffer containing 0.01 M EDTA, pH 5.25) and α-N-glyoxylyl-MKA (1.23 mM in the same buffer as used for Biotin-C6-Cys) were mixed in an Eppendorf cap in order to obtain a two-fold molar excess of 1,2-aminothiol over aldehyde. The conjugation was completed within 7 hours as monitored by analytical HPLC. Two diastereomeric biotin conjugates ($t_{R1}$=16.81 minutes and $t_{R2}$=17.09 min) were then separated with the excess Biotin-C6-Cys on the semi-preparative HPLC column. The diastereoisomers have the same molecular mass as determined by MALDI-MS (calc. for M+H+, 833.1, found, 833.1).

(2) BCC-Thz-SQFQIHGPR SEQ ID NO:14 BCC (0.45 mg, 1 μmol) and α-N-glyoxylyl-SQFQIHGPR SEQ ID NO:14 (1.13 mg, 1 μmol) were dissolved in 1 ml of 0.2 M sodium acetate buffer containing 0.01 M EDTA, pH 5.25 respectively. 200 μl from each solution were taken and mixed in an Eppendorf cap to allow the conjugation. Aliquots were taken at 3, 6 and 9 h, diluted with water containing 0.046% TFA and analyzed by HPLC to monitor the progress of the conjugation. The product has a $t_R$ of 17.44 minutes. MALDI-MYFS (calc. for M+H+, 1552.8, found 1552.5±1).

(3) BCC-Thz-PTH a-N-glyoxylyl-PTH (0.2 mg, 0.05 μmol) was dissolved in 200 μl of 0.2 M sodium acetate buffer containing 0.01 M EDTA, pH 5.25. To this was added 100 μl of Biotin-C6-Cys (1 mM in the same buffer used for the aldehyde). The conjugation was monitored by HPLC. After 7 h, α-N-glyoxylyl-PTH disappeared completely and a new peak with $t_R$=22.33 minutes was observed. The product was then isolated by the semi-preparative HPLC using a linear gradient from 10% to 70% B. MALDI-MS (calc. for M+H+, 4515.3, found 4516.6±1).

Oxidation and labeling of glycoprotein. Twenty μl aliquots containing 1–200 ng $a_1$-acid glycoprotein dissolved in 100 mM sodium acetate, 1% SDS, 2 mM—mercaptoethanol, 0.02% sodium azide, pH 5.5) were oxidized at 4° C. for 30 minutes as reported by D. J. O'Shannessy et al (15). The oxidation concentration of $NaIO_4$ was 1 mM. After destroying the excess periodate with sodium sulfite, the oxidized samples were incubated with 20–50 fold excess BCC overnight. The samples were then subjected to ELISA, stained with an avidin-peroxidase and scanned at 450 nm by an EIA plate reader. TMB was used as substrate.

Results and Discussion

Design and synthesis of 1,2-aminothiol containing ligands. A general design of the capture ligand (FIG. 20) for the site-specific conjugation contains three elements: a desired ligand (reporter), a flexible spacer and a 1,2-aminothiol. The $C_6$ diamino-spacer arm is inserted between linkage and ligand to reduce the steric hindrance and improve reactivity. The present Example demonstrates biotin as a ligand to examine feasibility of this new conjugation chemistry. The capture ligand is a cysteine which contains a 1,2-aminothiol moiety for the thiazolidine reaction.

The synthesis of BCC is shown in FIG. 21. Biotinylimidazolide was prepared from biotin and N,N'-carbonyldiimidazole according to the procedure described by Jasiewicz et al. (13) and converted to biotinyl-NH$(CH_2)_6$-Boc by the addition of Boc-NH$(CH_2)_6$-$NH_2$HCl and NMM. After deprotection with TFA, Boc-Cys(Trt)-OH was coupled to the biotin moiety by HBTU/NMM activation method. Biotin-$C_6$-Cys(Trt)-Boc was then treated by TFA/thioanisole to obtain BCC. There are two distinct advantages of this design. First, the capture ligand containing cysteine is highly aqueous soluble. This enables all conjugations to be performed in a mild aqueous buffer system with little perturbation to the conformation of the biologically-active peptides or proteins. Second, the ligand is highly accessible and adaptable by solid phase synthesis for other reporter groups.

Generation of carbonyl groups. The carbonyl groups could be introduced to an unprotected peptide or protein in a variety of ways (14). The most convenient method would be through periodate oxidation of 1,2-aminoalcohol of Ser or Thr placed at the N-terminal, side chain of lysine or C-terminal, or of the carbohydrate sites of glycoproteins. The oxidation of 1,2-aminoalcohol was rapid (<5 minutes) at pH 7 and found to be 1,000 times faster than the oxidation of vicinal cis-diols present in the glycoproteins.

Possible side reactions of the periodate-mediated aldehyde generating method .include oxidation of susceptible side chains of Met, Trp and His; with the conversion of Met to Met sulfoxide [Met(O)] presenting the gravest danger (3). This side reaction was examined by a tetrapeptide, Thr-Met-Lys-Ala SEQ ID NO:16. Oxidation at pH 7 in the presence of 5–10 fold of Met as scavenger gave the desired α-N-glyoxylyl derivative >99% within 5 minutes with no observable Met(O)-tetrapeptide byproducts as determined by analytical HPLC and MALDI-MS. Oxidation at <pH 5 produced Met(O)-tetrapeptide quantitative even in the presence of large excess of Met as scavenger. This is attributed by the increased oxidation potential of periodate which increases as pH becomes more acidic. Thus, selectivity of aldehyde-conversion of N-terminal Ser/Thr and Met(O) formation could be achieved at near neutral pH. The aldehyde formation was confirmed chemically by reaction with 2,4-dinitrophenylhydrazine and by mass spectrometric analysis which showed both the aldehyde and the hydrate form (M+18). The interconversion of these forms also caused peak broadening in RP-HPLC (FIG. 22).

Model study with synthetic peptides. The chemoselectivity of the 1,2-anminothiol with the carbonyl chemistry depends on the facile and stable thiazolidine formation under acidic condition. Amines such as α- and ε-amines as well as guandino groups can react with carbonyl to form a Schiff base. This reaction is not favored under aqueous under acidic conditions in which the amines are protonated and become pseudo-protected.

To substantiate the chemoselectivity of the thiazolidine formation and to rule out the participation of Schiff base formation, two model peptides are used. The first peptide, TA-4 (Thr-Met-Lys-Ala SEQ ID NO:16 ) contains an internal lysine which can react with periodate-oxidized TA-4 intramolecularly to form oligomerized product. Reaction of BCC in a ratio of 3:1 or 1:1 revealed that the conjugation was highly specific. RP-HPLC revealed only the desired product in >95%. By-products due to intramolecular or intermolecular Schiff base formation were not observed.

The second model peptide, SR-10 (SSFQIHGPR) SEQ ID NO: 14 contains arginine and histidine and is intended to be a model compound to test whether the guanidino or imidazole groups would react with the aldehyde and at the same time to define optimum conjugation conditions. Again, the glyoxylyl group was generated by periodate oxidation at pH 5.5 and reacted with BCC under various conditions. HPLC analysis showed the thiazolidine formation at the N-terminus of the SR10 was quantitative with no visible byproducts. A time course of conjugation With BCC to the aldehyde in a ratio of 1:1 showed that the reaction was complete after 9 hours incubation as traced by analytical HPLC (FIG. 23). With BCC to the aldehyde in a ratio of 3:1 or higher the conjugation was complete within 4 hours.

A consequence of the thiazolidine formation is the generation of a new stereogenic center at the C-2 carbon of thioproline ring. For small peptides, such as TMKA, the conjugation resulted in a diastereomer separable by RP-HPLC (FIG. 22). With larger peptides the diastereomers are usually not separable (FIGS. 23 and 24). The formation of isomers is a general rule for addition reaction with carbonyl. In the case of oxime or hydrazone formation, a pair of geometric isomers is obtained. In the present Example, stereoisomer formation does not distract from the simplicity and specificity of this reaction.

One-step or two-step method The site-specific conjugation could be accomplished in one-step or two-step fashion. In the one-step method, the product obtained from oxidation of the N-terminal Ser or Thr to glyoxyl moiety is not purified and is immediately subjected to the condensation with BCC to form the thiazolidine reaction by acidifying the reaction medium to pH 5.5. The oxidation with Ser/Thr yielded one mole of formaldehyde or acetaldehyde which was quenched with the excess BCC to form their corresponding thiazolidine byproducts and which are removed subsequently by RP-HPLC or other appropriate purification methods.

In the two-step method, the oxidized product containing the glyoxyl moiety is first purified under acidic condition to remove the formaldehyde or acetaldehyde byproduct attendant with the periodate-mediated oxidation. The purified product was then subjected to the thiazolidine reaction. It was determined that both methods are highly suitable and can be used without affecting the quality or yield of the reaction when the carbonyl component is used as the limiting reagent. The only difference in the two-step method is the excess of equivalent of BCC being used.

The rate of thiazolidine formation was dependent on the concentration df BCC. With a three-fold excess of BCC, reaction with SR-9 or MA-3 was accomplished in <4 hours. With 1:1 ratio of ligand to the glyoxylyl-SR-9 or MA-3, the reaction required 9 hours for completion.

Biotinylation of parathyroid hormone (human). PTH is a 34-amino acid hormone and is a challenging example for site-specific modification. It contains 15 of the 20 genetic code amino acids including Lys, Met, His and Trp. The latter are susceptible to oxidation and electrophilic addition of aldehyde.

Periodate-mediated oxidation of Ser-PTH in the presence of 20-fold excess of Met resulted in quantitative yield of $\alpha$-N-glyoxylyl-PTH in 5 minutes as shown by RP-HPLC revealing a single peak. Site-specific conjugation via thiazolidine formation with BCC at pH 5.2 was accomplished by one-step or two-step method to give >95% yield of the desired product. The purified biotinylated PTH gave the desired amino acid composition upon hydrolysis and the expected MW (Calc. for M+H+, 4515.3., found, 4516.6) (FIG. 24).

Biotinylation of $\alpha_1$-acid glycoprotein. A general method for the detection and quantitation of glycoproteins using ELISA on the basis of this new conjugation chemistry was established. $\alpha_1$-Acid glycoprotein was chosen for this purpose, since the quantitative determination of $\alpha_1$-acid glycoprotein is of diagnostic interest. The conjugation was carried out in a one-step fashion. Thus, $\alpha_1$-acid glycoprotein was dissolved in 100 mM sodium acetate, 1% SDS, 2 mM $\beta$-mercaptoethanol, 0.02% sodium azide, pH 5.5. The oxidation was performed at room temperature for 30 minutes by sodium periodate in a concentration of 1–10 mM according to the procedure described by D. J. O'Shannessy et al (15). The excess oxidation agent was destroyed by the addition of sodium sulfite. Twenty to fifty fold excess of BCC was used for the conjugation. The conjugation was allowed to proceed at pH 5.5 overnight. The biotinylated samples were then subjected to ELISA analysis and stained with an avidin-peroxidase. As little as 1 ng of $\alpha_1$-acid glycoprotein can be detected using this method (FIG. 25).

This Example has described a general facile and site-specific modification via thiazolidine reaction of synthetic peptides and glycoproteins using biotinylation as a model. Since the 1,2-aminothiol of cysteine or the carbonyl precursor as Ser or Thr can be placed anywhere in the peptide sequence, this method is particularly convenient for synthetic peptides. For proteins with N-terminal Ser and Thr or oligosaccharide, this method is also suitable. Furthermore, Ser and Thr can be introduced to the proteins by recombinant DNA method to make this method applicable to any recombinant DNA expressed proteins.

Although the present Example demonstrates biotin as a reporter group, other ligands can also be used. The general design of the capture ligand of the invention should be suitable for reporter groups of radiolabel, fluorescent and even antibody. Three attractive features of this approach are (1) biotin could be introduced distant from the putative bioactive center, (b) chemistry performed on the peptide or glycoprotein is solely limited to the 1,2-aminothiol and the generated aldehyde to give thiazolidine, thus avoiding unnecessary side reactions and (3) the conjugate obtained is totally stable to a wide range of pH.

The following is a list of publications cited for the instant Example only:

1. Drijfhout, J. W. Bloemhoff, W., Poolman, J. T., and Hoogerhout, P. (1990) Anal. Biochem. 187, 349–354.
2. Wetzel, R., Halualani, R., Stults, J. T., and Quan, C. (1990) Bioconjugate Chem. 1, 114–122.
3. Geoghegan, K. F., and Stroh, J. G. (1992) Bioconjugate Chem. 3, 138–146
4. Schwarz, A., Wandrey, C., Bayer, E. A., and Wilchek, M. (1990) Methods Enzymol. 184, 160–162.
5. Rose, K., Jones, R. M. L., Sundaram, G., and Offord, R. E. (1089) Peptides 1988 (Jung, G., and Bayer, E., Eds.) pp 274–276, Walter de Gruyter & Co., New York.
6. Bayer, E. A., Skutelsky, E., and Wilchek, M. (1982) in Methods in Enzymology (Ginsberg, V., Ed.) Vol. 83, pp. 185–215, Academic Press, New York.
7. O'Shannessy, D. J., Doberso, M. J., and Quarles, R. H. (1984) Immunol. Lett. 8, 273–277.
8. Gershoni, J. M., Bayer, E. A., and Wilchek, M. (1985) Anal. Biochem. 146, 59–63.
9. Upeslacis, J., and Hinman, L. (1988) Annu. Rep. Med. Chem. 23, 151–160.
10. Rodwell, J. D., Alverez, V. L., Lee, C., Lopes, A. D., Goers, J. W. F., King, H. D., Powser, H. J., and McKearn, T. J. (1986) Proc. Natl. Acad. Sci. U.S.A. 83, 2632–2636
11. Liu, C. F., and Tam, J. P. (1994), *J. Am. Chem. Soc.* 116, 4149–4153
12. Merrifield, R. B. (1963) *J. Am. Chem. Soc.* 85, 2149–2154
13. Jasiewicz, M. L. , Schoenberg, D. R., and Mueller, G. C. (1976) Exp. Cell Res. 100, 213–217
14. Tam and Spetzler
15. O'Shannessy, D. J., Voorstad, P. J., and Quarles, R. H. (1987) Anal. Biochem. 163, 204–209

EXAMPLE 15

Peptide Synthesis Using Unprotected Peptides Through Orthogonal Coupling and Intramolecular Acyl Transfer The present Example describes an approach to the synthesis of peptides bearing no protecting groups through an orthogonal coupling method to capture the acyl and amine segments as thioester ester which then undergo an intramolecular acyl transfer to form a cysteinyl peptide bond. Two orthogonal coupling methods to give the covalent ester intermediate were achieved by either a thiol-thiobster exchange mediated by trialkylphosphine and alkylthiol or a thioesterification by $C^{\alpha}$-thiocarboxylic acid reacting with an $N^{\beta}$-bromoalanine. Using this approach, -unprotected segments of 4 and 37 amino acids were coupled to give peptides ranging from 9 to 54 residues in aqueous solution with great efficiency.

Materials and Methods

Solid phase peptide synthesis was performed manually or on an ABI 430A synthesizer. Analytical HPLC was run on a Shimadzu system with a Vydac column (0.46 cm×25 cm, $C_{18}$ reversed phase, 5 μm) using linear gradients of buffer B (60% acetonitrile in $H_2O$/0.04% TFA) in buffer A (5% acetonitrile in $H_2O$/0.045% TFA), with UV detection at 225 nm and at a flow rate of 1.0 Ml/minutes or 1.5 ml/minutes. Mass spectra were obtained with the Matrix-Assisted Laser Desorption Mass Spectrometry. The calculated mass units were given as average isotopic values. Boc- and Fmoc-amino acid derivatives were purchased from Bachem California, Torrance, Calif.

Solid phase peptide synthesis. Peptides, CA-4 (e.g., CAKA SEQ ID NO:17 and CFKASEQ ID NO:18); BV-7 were synthesized by the Fmoc/t-Bu strategy on Wang resin (11) using the BOP coupling protocol and cleavage by 95%TFA/4% $H_20$/1% triisopropylsilane. Thioester, thiocarboxylic peptides and CA-17 were prepared by the Boc/Benzyl strategy using either the BOP coupling protocol (12) or the DCC/HOBt method. CA-17 was synthesized from Boc-Ala-$OCH_2$-Pam resin (13). The synthesis of peptide SG-5 was started by coupling of Boc-Gly-$S(CH_2)_2COOH$ to MBHA resin while GL-6 and PN-37 were started by coupling of Boc-Leu-$S(CH_2)_2COOH$ or Boc-Asn-$S(CH_2)_2$ COOH to H-Gly-$OCH_2$-Pam resin respectively (14). Dnp protecting group on His residues was removed before HF cleavage by 10% thiophenol/2.5% DIEA in DMF (1×2 h, 2×8 h). Ser-Ala-Lys-Leu-SH SEQ ID NO:19 was synthesized on the handle of 4[(-Boc-Leu-S)benzyl]phenoxyacetic acid (15) using Boc/benzyl chemistry. After HF cleavage with 9:1 (HF:anisole), the crude peptide was purified by RP-HPLC. LD-MS: 434.3±0.4 (calc. for M+H, 434.6). Peptide PN-37 was cleaved using the Low-High HF protocol (16) and the others were cleaved with the High HF method (17). CA-17 was synthesized and stored in the disulfide formed by the DMSO oxidation method. MS $[M+H]^+$: CA-17, m/z 1801.0 (calc.), 1801 (found); PN-37, m/z 4281.8 (calc.), 4282 (found).

Boc-BrAla was obtained from Boc-Ser (4.1 g, 20 mM) in DCM (50 ml) and THF (10 ml) $CBr_4$ (9.95 g, 30 mM) and triphenylphosphine (8.92 g, 34 mM) according to Hayashi et al. (18). The organic phase was washed with $H_2O$ saturated NaCl and $H_2O$. After removal of DCM, ethyl acetate was added to the residue and it triphenylphosphine oxide was removed by filtration. The residue was purified by silica gel column chromatography using hexanes/ethyl acetate/acetic acid=60/4011 as eluent. Yield: 1.68 g (31.3%). BrAla-Pro-Gly-Gly-Asn-Cys(Acm)-Val-OH SEQ ID NO:20 was prepared by Fmoc chemistry on Wang resin using DCC/HOBt method. The peptide was cleaved from resin with 95% TFA/anisole for 30 minutes. After removal of TFA the peptide was precipitated with dry ethyl ether and washed with dry ether. The crude peptide was purified with RP-HPLC. LD-MS: 767.6±0.7 (calc. for M+H, 767.7)

General Reaction of Thioesterification through Thiocarboxylic acid and β-Bromo-alanine. Thioleucine (Leu-SH) and BrAla were obtained after deprotection of Boc with TFA. Thioesterification in 50% DMF: To the solution of Leu-SH (25 μl, 0.08 M), BrAla-OH (25 μl, 0.08 M) in DMF (100 μl) buffered solutions (50 μl 0.4 M) were added to give final solution of pH 5.2, 5.7, and 6.2 respectively. The final concentration of Leu-SH and BrAla-OH was 0.01 M and analyzed by RP-HPLC and LD-MS. The desired dipeptide Leu-Cys (retention time 7.1 min) and the isomer 11 (retention time 9.2 min) were obtained. Both products contained the same MW as Leu-Cys. The percentage of 11 increased as the pH of reaction solution increased (pH 5.2, 18%; pH 5.7, 30%, pH 6.2, 41%). The thioesterification was complete in less than 15 h. Ligation in water: To the solution of Leu-SH (50 μl, 0.04 M) and BrAla (50 μl, 0.04 M) buffered solutions (100 μl 0.2 M) of pH 5.6, 6.0, and 6.7 respectively. 8 and 11 in similar ratio were formed slower than in 50% DMF.

Model reaction of thioester peptides with Cys-peptides. BocGlySR and CA-4I (CA-4 or other cysteinyl-containing tetrapeptides in equal molar ratio (1.0 μM) with various additives (Tables 8 and 9) in a buffered routine of 5.6, 6.6, 7.2 and 7.6 were allowed to react at predetermined intervals at ambient temperature. Yields and prudent distribution were analyzed by RP-HPLC using a linear gradient of 0–85% B in 30 minutes (A and B; See General Method). Retention times (minutes) for products were: 1 22.7; 2 27.4; 3 23.5, 26; 4 14.2. α-, ε-, and α-, ε-acylated peptides were confirmed by independent synthesis. MALDMS 1 622.74 (calc.), 623.4 (found).

Thiol-thioester reaction of PN-37 with CA-17. PN-37 (0.43 mg, $1\times10^{-4}$ mM) and CA-17 (0.45 mg, $2.5\times10^{-4}$ mM) were first dissolved in 50 μl buffer B (60% $CH_3CN$ in $H_2O$/0.04%TFA) in a small (0.5 ml) plastic vial. TCPE (0.17 mg, 6×10–4 mM) and HOSu as a weak acid (~0.1 mg, $8.7\times10^{-4}$ mM) were then added. The pH was adjusted to about 6.5 by addition of solid sodium acetate. RP-HPLC monitoring showed that about 60% of ligation product was formed (peak 2 in FIG. 29), the peak corresponding to the starting material (peak 1) was found to contain around one-third of the hydrolysis product of the thioester as confirmed by MS. The identity of the broad peak at 23.5 minutes was not clear, since no detectable species were found by MS analysis. HPLC gradient was 40%–75%B for 35 minutes. The peptide CA-17 eluted immediately with the injection peak. MS $[M+H]^+$: ligation product (PA-54), m/z 5920.8 (calc.), 5919.6 (found); hydrolysis product of PN-37, m/z 4136.8 (calc.), 4136 (found).

Results

Preparation of Cysteinyl and acylated thioester segments. Unprotected amine segments containing an amino terminal cysteinyl residue were synthesized by the conventional solid-phase method (3) using either Boc- or Fmoc-chemistry. Acylated thioester segments and thiocarboxylic acid were also prepared by the stepwise solid phase synthesis using thioester resin developed by Aimoto et al. (14) and Yamashiro and Li (15). Because of the lability of thioesters to amine nucleophiles in the Fmoc-chemistry, acylated thioesters or thiocarboxylic segments were prepared by the Boc-chemistry. Unprotected acylated thioester segments were cleaved from the resin by a modified low-high HF (16) and purified by RP-HPLC. All peptide segments were vigorously characterized including mass-spectrographic analyses and gave the expected results.

Model reactions to study selectivity and product distribution of the thiol-thioester exchange. The rates, yields and product distribution of the thiol-thioester exchange were studied at four discrete pH, 5.6, 6.6, 7.2 and 7.6 with a model peptide, CFKA and Boc-Gly-SR (R=propionic acid). Due to the presence of thiols in both starting material and products, there are 16 possible products even with this simple model reaction and 11 of which would contain disulfides with one of the thiol-containing compounds: CFKA, BocGly-CFK, and thiopropionic acid derived from Boc-Gly-SR (FIG. 27). Rates of the thiol-thioester exchange increased about 1.5–2 fold with each unit increment of pH as the anionic thiolate concentration increased. The reaction was largely complete at pH 7.6 in 12 hours. However, three groups of byproducts were also obtained: α,S-diacylated 2, a mixture of α-acylated product with disulfide 3, and the hydrolysis product, Boc-Gly (Table 8). At pH 5.6 where the reaction was the slowest, hydrolysis of the thioester was the greatest at 78% and the lowest at pH 7.6 where the thiolate could significantly competed for the hydrolysis to yield 56% of the desired product 1.

TABLE 8

Effect of pH on Product Distribution in Thiol-thioester Exchange in 7 to 18 hours

| | Acylated Products (mol %)[1] | | | |
|---|---|---|---|---|
| pH | α(1) | α,S(2) | α,SSR(3)[2] | BocGlyOH[3] |
| 5.6 | 5 ± 2 | 2.5 ± 1 | 12 ± 1 | 78 ± 3 |
| 6.6 | 43 ± 2 | 3 ± 1 | 20 ± 1 | 34 ± 2 |
| 7.2 | 44 ± 1 | 3 ± 1 | 16 ± 1 | 38 ± 2 |
| 7.6 | 56 ± 1 | 4 ± 1 | 25 ± 1 | 15 ± 1 |

[1]Acylated products on α and thiol (S), see FIG. 27 for structure;
[2]α-acylated and thiol as mixed disulfide;
[3]Hydrolysis product.

These results prompted consideration for the use of a basic pH and a strong reducing environment containing large excess of an alkyl thiol and trialkylphosphine, $R_3P$, to inhibit hydrolysis of the thioester, and α,S-diacylated product 2, prevent disulfide formation and accelerate the reaction (Table 9). $R_3P$ was found to reduce disulfides and eliminate the disulfide byproducts 3 (Entry 2 and 3) while the excess thiol converted the α,S-diacyl byproduct 2 to the starting material 1 (Entry 4–6). Indeed, a combination of $R_3P$ and large excess of an alkyl thiol improved the yield to >95% with near no detectable hydrolysis of BocGlySR and few other byproducts (Entry 9 and 10) and appears to be an optimal condition for the thiol-thioester exchange. It was determined that a water-soluble phosphine, TCEP, was convenient to use, although others, such as triethylphosphine, were also effective. There is evidence that $R_3P$ activates the thioester as a phosphonium salt to accelerate the thiol-thioester exchange since the reaction was largely complete in 4 to 8 hours at pH 7.2 and $R_3P$ promoted α,S-acylated byproducts (Entry 2–4, 7). The combination of $R_3P$ and RSH was also studied at pH 6.6 and 7.6 with both two peptides CA-4 and CA4F (Table 10) and similar results and product distributions were obtained (data not shown).

TABLE 9

Effect of Alkyl Thiol and $R_3P$ on Thiol Thioester Exchange in 8 H at pH 7.2

| | | | Yield (mol %)[1] Acylated Products | | mixed disulfide |
|---|---|---|---|---|---|
| | Reagent | Equiv. | α(1) | α,S(2) | α,SSR(3) |
| 1 | None | | 44 | 4 | 17 |
| 2 | $R_3P^2$ | 2 | 87 | 13 | — |
| 3 | | 4 | 75 | 25 | — |
| 4 | $R_1SH^3$ | 1 | 35 | 14 | 51 |
| 5 | | 5 | 73 | 1 | 26 |
| 6 | | 10 | 82 | — | 18 |
| 7 | $R_3P + R_1SH$ | 2:2 | 80 | 6 | 14 |
| 8 | | 5:5 | 89 | 3 | 8 |
| 9 | | 2:5 | 95 | 3 | 2 |
| 10 | | 2:10 | 98 | <1 | 1 |

[1]Hydrolysis Product of BocGly < 2% except in 1;
[2]R = $CH_2CH_2COOH$;
[3]$R_1$ = $CH_2CH_2COOH$.

TABLE 10

Peptides Synthesized by Orthogonal Coupling through Thioester Capture

| | Acyl Segment | | Amine Segment | Method[1] | Yield (%)[2] |
|---|---|---|---|---|---|
| SG-5 | SRDFG[3] SEQ ID NO: 21 | CA-4 | CAKA SEQ ID NO: 17 | A | 88 |
| GL-6 | GERGAL[3] SEQ ID NO: 22 | CA-4F | CDHARHGFLPRHRD SEQ ID NO: 25 | A | 87 |
| AS-17 | AVSEINFMHNLG KHLSS[3] SEQ ID NO: 23 | CA-22 | CDHARHGFLPRHRD TGILDSC(Acm)A SEQ ID NO: 26 | A | 72 |
| PN-37 | PG1TLWQRPLVTI RIGGQLKEALLDT GADDTVLEEMN[3] SEQ ID NO: 24 | CA-17 | CHSGYVGARCEHA DLLA SEQ ID NO: 27 | A | 60[4] |
| SL-4 | SAKL[5] SEQ ID NO: 19 | BV-7 | BPGGNAC(Acm)V[6] | B | 60 |

[1]See FIG. 26;
[2]Based on Amine Segment with Acyl Segment in 1.2–1.5 fold excess and calculated from area ration corresponding to peaks of Amine Segment and product;
[3]as Thioester;
[4]in PN-37, yield was based on Acyl Segment with Amine Segment in 2.5 fold access;
[5]as Thiocarboxylic Acid;
[6]B = β-bromo-alanine.

The selectivity of aminolysis between α- and β-amine was also studied with model tetrapeptides CKFA SEQ ID NO:20, CAKA SEQ ID NO:17, and CFKA SEQ ID NO:18, containing a lysinyl amine near the amino terminal to compete for the acylation reaction. At pH 7.2 or lower, α-acylation was <1% and about 2% at pH 7.6, indicating the reaction is p-amine specific. Although the side reaction due to hydrolysis in Boc-Gly-SR was no longer a significant problem using our proposed condition, we found that it was still relatively significant with trifunctional amino acids whose side chain participated in assisted hydrolysis as in the case of PN-37 (Table 10) which contained a terminal Asn-SR. The covalent thioester intermediates leading to S to N-intramolecular acyl transfer was rapid and were not detectable by RP-HPLC. However, the proposed reaction scheme is consistent with the thiol side-chain initiated nucleophilic attack of the thioester rather than direct acylation by the α-amine. Tetrapeptides of S-protected CA-4 (Cys(Acm)-AKA SEQ ID NO:17), SAKA SEQ ID NO:30. GAKA SEQ ID NO:31 and LAKA SEQ ID NO:32 did not give any observable α-$N^{\epsilon}$-acylation in 18 hours at pH 6.6–7.6. Using these optimized conditions, four peptides ranging from 9 to 54 amino acids were prepared with 60–88% yield (Table 10). The synthesis of the 54-residue peptide was noteworthy because internal cysteine was unprotected and the coupling gave cleanly separable peaks for easy purification (FIG. 28). The disulfide bond of CA-17 was first reduced by TECP to allow productive thioester exchange of N-Cys thiol with the $C^{\alpha}$-acyl thioester of PN-37.

Thioesterification through thiocarboxylic acid and bromoalanine. Another orthogonal coupling method via thioesterification to capture amine and acyl segments (19) was also studied (FIG. 26). It was envisioned that a reverse directional nucleophilic capture of β-bromo alanine (BrAla) by a C-terminal thiocarboxylic acid would yield a similar covalent thioester. BrAla was obtained in good yield by triphenylphosine-mediated bromination of Boc-Ser either in solution (18) or in solid-phase. Boc-BrAla was incorporated in stepwise solid-phase synthesis scheme without much difficulty because it was the N-terminal amino acid residue as shown in the synthesis of BV-7 (Table 10).

For model reactions, the thioesterification of Leu-SH with BrAla at pH 5.2 to 6.2 was studied and two products with identical MW were obtained: the desired dipeptide 8 and its isomer 11 derived from the thiocarboxylic attack at the α-position of the aziridine ring (FIG. 29). The formation of aziridine ring of a N-terminal BrAla and the subsequent ring opening by the thiocarboxylate were expected due to the ease of 1,3-elimination of HBr, the highly labile proton on the α-amine as well as the ring strain to facilitate ring opening by LeuSH. Aziridine formation (19) was favored at pH>6 and under such a condition BrAla was converted in 1–2 hours. Thioesterification of aziridine or BrAla at pH>6 gave 8 and 11 in a ratio of 6:4 favoring ring opening at the less hindered β-position (21,22). At lower pH the aziridne formation was slow and the dominant thioesterification occurred by direct displacement of BrAla to reduce byproduct 11 to 18%.

BrAla is prone to β-elimination to give dehydroalanine and the thioesterification could occur by the Michael addition of the thiocarboxylic acid. This mechanism was ruled out because there was no racemization after comparing with authentic D-Leu-Cys and Leu-D-Cys samples in RP-HPLC. Furthermore, β-elimination of N-terminal Br-Ala could only occur at pH>11 with rapid decomposition to pyruvic acid. The feasibility of the thioesterification in our orthogonal coupling method was validated in the synthesis of sperm activating peptide ($Cys^5$-$Cys^{10}$, Ser-Ala-Lys-Leu-$Cys^5$-Pro-Gly-Gly-Asn-$Cys^{10}$-Val SEQ ID NO:33 in 60% yield (Table 10).

Discussion

There are three elements in the approach of the present Example: (1) the use of unprotected peptides, (2) orthogonal coupling methods, and (3) intramolecular acyl transfer. The use of unprotected peptide segments or protein domains as building blocks presents significant advantages and new challenges. Advantages include aqueous solubility, accessibility to protein purification methods, and readily available source of building blocks derived from solid-phase peptide syhthesis and recombinant DNA methodologies. More importantly, large unprotected peptides are likely folded into ordered structures which offer solvent-exposed N- and C-termini and the possibility of conformational assistance (21–22) in placing two segments in close proximity to overcome entropy in effecting the amide formation. Finally, there is no strong acid or other harsh treatment to denature the products after the coupling reaction since there are no protecting groups to be removed. These advantages are usually not found in the conventional convergent approaches (23–27) which use partially or fully protected peptide segments.

The use of unprotected peptides also necessitates the development of new methods to achieve high regioselectivity in peptide bond formation. Coupling reaction with such regioselectivity would require orthogonality by a capture step to form a covalent thioester between the acyl and amine segments subsequently leading to a proximity-driven S to N-intramolecular acyl transfer through a 5-member intermediate to give a peptide bond (FIG. 26). Our results show that this can be achieved efficiently by two methods. First, it can be formed by a nucleophilic attack of the side-chain thiol of a cysteinyl amine segment on an acylated thioester. This reaction becomes highly efficient in a strongly reducing and nucleophilic environment containing a combination of trialkylphosphine and alkyl thiol. $R_3P$ eliminates byproducts due to disulfide formation and accelerates the thiol-thioester exchange while the alkyl thiol converts the S-acyl byproducts to the desired product and the starting material. Second, the thioester can also be formed by the reverse direction through the nucleophilic attack of thiocarboxylic acid of the acyl segment on bromoalanine of the amine segment. Bromoalanine or the active form aziridine provides an alternative approach of preparing amine segments without the use of N-terminal Cys and may be useful for the use of those segments containing disulfides or thioester linkages.

The thiol-thioester exchange also provides an excellent example to illustrate the concept of orthogonal coupling method. Thioester is relatively stable to amines but reactive to thiols under aqueous condition at pH 5–7.5. Under the conditions containing $R_3P$ and excess alkylthiol, the equilibration is nonproductive between thioester and those thiols occurring as cysteinyl side chains in the internal sequence of the amine or acyl segments as shown in Table 10, but becomes productive with 1,2-aminothiol which occurs only in the N-terminus of the amine segment. Thus, even though the acylated thioester could react with many thiols, only N-terminal cysteine will yield a single thermodynamic stable product. Similar concept of orthogonality in coupling reactions are contemplated by the invention in capture steps mediated by thiazolidine and oxazolidine ring (6,7) and disulfide (8,9) formation.

Recently, a scheme based thioester exchange was reported (5) using $C^{\alpha}$-thiocarboxylic, Ellman's reagent and cysteinyl thiol at basic pH. The inventors have shown that this scheme does not proceed through a thiol-thioester exchange but rather a mixed acyl disulfide, a subsequent disulfide exchange with cysteinyl thiol, and eventually an intramolecular acyl transfer involving a six-member intermediate containing disulfide rather than a five-member intermediate of a thioester (FIG. 26) to yield a peptide containing a hydrodisulfide with the cysteine (9).

Intramolecular acyl transfer as a mechanism to obtain high effective molarity and to overcome entropy in coupling two peptide segments of high molecular weights has been advocated by Kemp and his co-workers (4, 28). Interconversion of intramolecular acyl transfer are well known in peptide synthesis as side reactions (7,29) and recently, have been found as a significant cellular process of post-translational protein splicing (31). Thus, the combination of orthogonal coupling through the amino terminal side chain and a subsequent intramolecular acyl transfer could be considered as a bio-organic approach to mimic the natural process in peptide synthesis and may hold potential promise for synthesis of large peptides and semi-synthesis of proteins.

The following list of publications is representative for this Example only:

1. Tam, J. P. (1988) *Proc. Natl. Acad. Sci. USA* 85, 5409–5413.
2. Mutter, M. and Vuilleumier, S. (1989) *Angew. Chem. Int. Ed. Engl.* 28, 535.

3. Merrifield, R. B. (1963) *J. Am. Chem. Soc.* 85, 2149–2154.
4. Fotouhi, N., Galakatos, N. G., Kemp, D. S. (1989) *J. Org. Chem.* 54, 2803.
5. Dawson, P. E., Muir, T. W., Clark-Lewis, I. & Kent, S. B. H. (1994) *Science* 266, 776–779.
6. Liu, C.-F. and Tam, J. P. (1994) *Proc. Natl. Acad. Sci. USA* 91, 6584–6588.
7. Liu, C.-F. and Tam, J. P. (1994) *J. Am. Chem. Soc.* 116, 4149.
8. Tam, J. P., Liu, C. F., Lu, Y. A., Shao, J., Zhang, L. and C. Rao (1995) Proceedings of the 14th American Peptide Society, (P. Kaumaya and R. Hodges, eds.). In press.
9. Liu, C. F., Rao, C. and Tam, J. P. (1995) Proceedings of the 14th American Peptide Society, (P. Kaumaya and R. Hodges, eds.). In press.
10. Barany, G. and Merrifield, R. B. (1977) *J. Am. Chem. Soc.* 99, 7363–7365.
11. Wang, S.-S. (1973)) *J. Am. Chem. Soc.* 95, 1328–1333.
12. Castro, B., Dormoy, J. R. G., Evin, G. & Selve, C. (1975) *Tetrahedron Lett.* 1219–1222.
13. Mitchell, A. R., Kent, S. B. H., Engelhard, M. & Merrifield, R. B. (1978) *J. Org. Chem.* 43, 2845–2852.
14. Hojo, H. and Aimoto, S. (1991) *Bull. Chem. Soc. Jpn.* 64, 111–117.
15. Yamashiro, D. and Li, C. H. (1988) *Int. J. Pept. Protein Res.* 31, 322.
16. Tam, J. P., Heath, W. F. & Merrifield, R. B. (1983) *J. Am. Chem. Soc.* 105, 6442–6455.
17. Sakakibara, S., Shin, K. H., Schneider, W. & Hess, G. P. (1962) *J. Am. Chem. Soc.* 84, 4921–4928.
18. Hayashi, H., Nakanishi, K., Brandon, C. and Marmur, J. (1973) *J. Am. Chem. Soc.* 95, 8749–8757.
19. Photaki, I. and Bardakos, V. (1965) *J. Am. Chem. Soc.* 87, 3489–3492.
20. Okawa, K. and Nakajima, K. (1981) *Biopolymers* 20, 1811–1821.
21. Homandberg, G. A. and Chaiken, I. M. (1980) *J. Biol. Chem.* 255, 4903.
22. Wallace, C. J. A. and Corthasy, B. E. (1986) *Protein Eng.* 1, 23.
23. Hirschmann, R., Nutt, R. F., Veber, D. F., Vitali, R. A., Varga, S. L., Jacob, T. A., Holly, F. W. & Denkewalter, R. C. (1969) *J. Am. Chem. Soc.* 91, 507–508.
24. Kiyama, S., Fujii, N., Yajima, H., Moriga, M. & Takagi, A. (1984) *Int. J. Pept. & Protein Res.* 23, 174–186.
25. Kuroda, H., Chen, Y.-N., Kimura, T. & Sakakibara, S. (1992) *Int. J. Pept. & Protein Res.* 40, 294–299.
26. Blake, J. and Li, C. H. (1981) *Proc. Natl. Acad. Sci. USA* 78, 4055.
28. Jackson D. Y., Burnier, J., Quan, C., Stanley, M., Tom, J. & Wells, J. A. (1994) *Science* 266, 243.
29. Kemp, D. S. and Carey, T. I. (1993) *J. Org. Chem.* 58, 2216.
30. Wieland, T. and Bokelmann, E. (1952) *Ann.* 576, 20.
31. Kane, P M., Yamashiro, C. T., Wolczyk, D. F., Neff, N., Goebl, M. And Stevens, T. H. (1990) *Science* 250, 651–657.

EXAMPLE 16

Orthogonal Coupling Method As An Approach to Capture and Acyl Activation in Protein Synthesis To achieve a high requirement of regioselectivity in amide bond formation, orthogonal coupling methods for $N^{\alpha}$-amine in the presence of other reactive functional groups were developed. Orthogonal coupling method is similar in concept to the orthogonal protecting group and proceeds independently of amines and other functional moieties. The present Example describes four orthogonal coupling methods which exploit reactions involving thiazolidine, thioester and disulfide.

Results and Discussion

Conceptual approach. Scheme 1 below consists of (1) an orthogonal coupling method as a capture step to bring the two segments to close proximity (generally, a bond is formed between the α-acyl and side chain of the two different segments) and (2) the amide bond formation through a proximity-driven intramolecular acyl transfer [1,2].

Aldehyde capture. Aldehyde capture is the first orthogonal coupling method developed by our laboratory in 1992 [1]. The orthogonality of this reaction exploits the thiazolidine or oxazolidine formation of aldehyde with 1,2-substituted aminothiol or 1,2-aminoethanol. Since only N-terminal amino acid Cys or Thr contains such an arrangement of functional groups, the side chain lysine or other p-amine is excluded from this reaction. The specificity of the aldehyde capture can be demonstrated with a dipeptide library containing 400 dipeptides and N-terminal cysteine reacted almost immediately with aldehyde to form thiazolidine [3]. This strategy was applied and resulted in the successful synthesis of cyclic, branched and large peptides including three analogs of HIV-1 protease.

Scheme 1

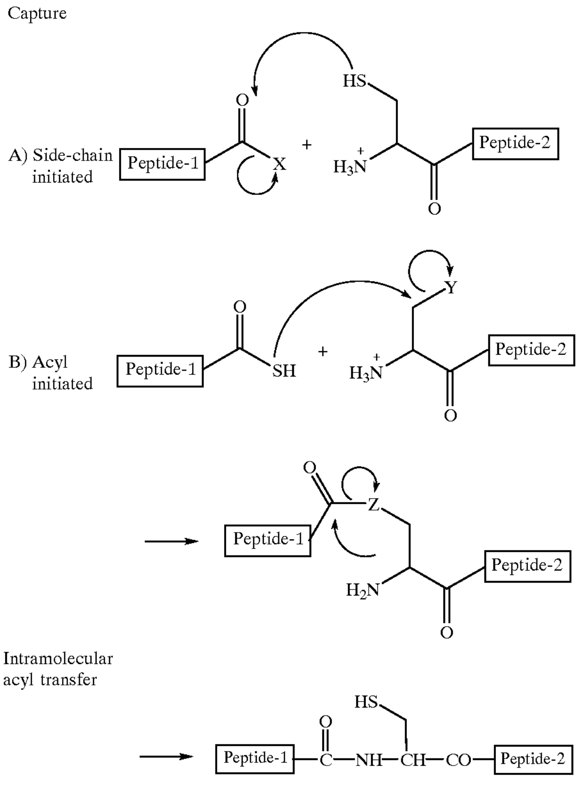

| X | Y | Z | R |
|---|---|---|---|
| SR | — | S | H |
| $SSR_1$ | — | SS | H |

-continued

Scheme 1

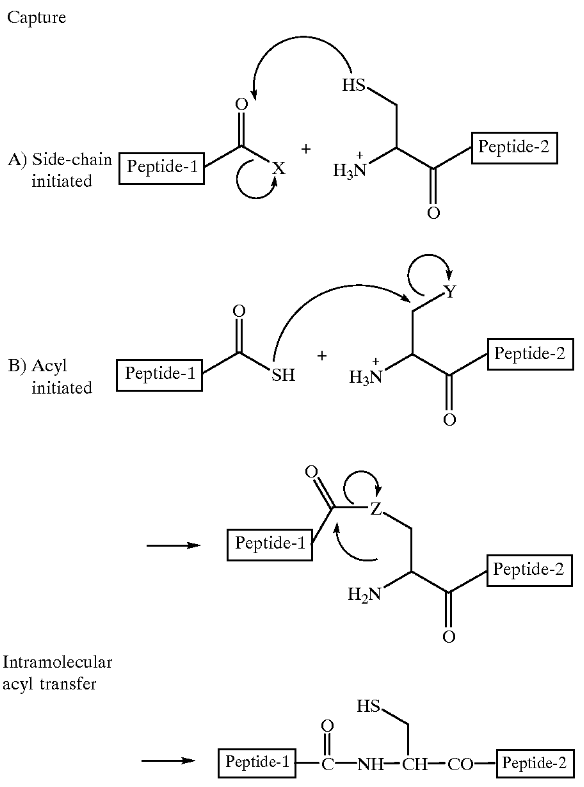

| X | Y | Z | R |
|---|---|---|---|
| — | Br, Tos | S | H |
| — | $SSR_2$ | SS | H |
| $OCH_2CHO$ | — | THz | |

A schematic representation of the orthogonal capture of the orthogonal capture and intramolecular acyl to peptide synthesis of unprotected segments. R1, R2 = Npys, Thz-4-hydroxymethal thiazolidine.

Thioester exchange. Another orthogonal coupling method is the thiol-thioester exchange in which the acyl segment containing a thioester exchanges with the amino terminal cysteine to form a covalent thioester. Thioester was relatively stable to aminolysis at acidic or neutral pH, but reacted preferentially with thiols at near neutral pH, as shown in several model peptides containing both an amino terninal cysteine and a lysine. At pH 5.6 to 7.6, the selectivity between the α- and β-acylation was relatively high with an α/β ratio of >100:1. Such selectivity was not found in the activated acyl forms such as the succimide ester which reacted with thiol and amine rather nondiscriminately. Although cysteinyl thiols in the internal amino acid sequence would react with thioester, their reaction is non-productive. Thus, only the $N^{\alpha}$-terminal with a 1,2-aminothiol would lead to a stable product and thioester. This type of selectivity illustrates the concept of orthogonal coupling method in which there is significant difference in the reaction among the N-terminal amino acid (Cys), the side chain, and other α-amine groups.

The reactivity of the sulfhydryl group is both an asset and a problem. Reactivity of the sulfhydryl is necessary for the thiol-thioester exchange, but it gives 16 other byproducts leading to low overall yield, 10–40%. The major side products are (1) α-s-diacylation, (2) disulfide of α-acylated products and (3) hydrolysis of thioester to carboxylic acid.

This reaction has been optimized by activating the thioester while maintaining high orthogonality and keeping the reaction under reducing condition by using trialkylphosphine and a large excess of reduced thiol.

Because of the strong affinity of trialkylphosphine for sulfur, $R_3P$ reduces disulfides to thiols and thus keeps the thiols in a reducing form and eliminates 11 of the possible 16 byproducts being formed. More importantly, it accelerates the thiol-thioester exchange so that the reaction is completed within 17 hours. The excess reduced thiol serves to convert the α-s diacyl peptide to the desired product and the starting material. With this mixture, the yield increased to >90%.

Thioesterification. The covalent thioester was also achieved by direct thioalkylation between a thiocarboxylic acid and bromoalanine. The difference between this method and the previously discussed thioester exchange is that this reaction is acyl-initiated rather than by the thiol side chain. The reaction was performed at pH 4 to 5.5. Under such a condition, the possible side reaction due to β-elimination to give dehydroalanine was not observed. However, the formation of the 3-member ring, aziridine, became significant and was found to be an active intermediate in the reaction pathway.

Disulfide exchange. Finally, disulfide formation was also exploited as an orthogonal coupling method. Mixed disulfides could be achieved between the thiocarboxylic acid and the amino terminal cysteine and is bidirectional, i.e., the capture could be initiated by either thiocarboxylic acid or cysteinyl side chain.

Although this capture method is bidirectional, there are distinctive differences and significant advantages of favoring one direction. In the acyl-initiated mixed-disulfide formation with an acyl disulfide such as Ellman's reagent, activation of the thiocarboxylic acid with the Ellman's reagent would form a mixed disulfide leading to a reactive species and the advantage of orthogonality due to its high reactivity with amines.

To avoid the premature acyl activation and to provide high orthogonality, it was determined that activation of the side chain of cysteine first by acyl disulfide has significant advantages but will form the desired mixed disulfide with acyl segment bearing the thiocarboxylic acid and the acyl mixed disulfide would undergo another disulfide exchange to give an acyl-cysteine mixed disulfide, subsequently mediated by a six-member ring rather than a five-member ring as in the thioester intermediate. It was confirmed that Scheme 1 above represents the reaction path by obtaining the final products prior to the reduction step.

The present Example demonstrates that the development of orthogonal coupling methods allows highly regioselective amide bond formation of the $N^{\alpha}$-amine and the α-carboxylic acid. With these approaches, proteins, particularly those proteins >200 amino acids, can be successfully chemically synthesized to usher us into a new era of synthetic protein preparation.

The following is a list of publications for the instant Example only:

1. Liu, C. F. and Tam, J. P., Proc. Natl. Acad. Sci. USA (1993) 6584.
2. Kemp, D. S. and Carey, R. I. J. Org. Chem. 58 (1993), 2216.
3. Tam, J. P., Rao, C., Shao, J. And Liu, C. F., Int. J. Pept. Prot. Res. 45 (1995) 209.
4. Dawson, P. E., Muir, T. W., Clark-Lewis, I. and Kent, S. B. H. Science 266 (1994) 776.
5. Tam, J. P. and Lu, Y. A., Proc. Natl. Acad. Sci. USA (1995), In press.

EXAMPLE 17

New Resins For Chemical Ligation and Cyclization Of Unprotected Peptides

Conformationally constrained peptides, particularly end-to-end cyclic peptides, are useful to enhance biological activity and proteolytic resistance. Although many methods for cyclizing peptides have been reported [1–3], none is known for end-to-end cyclization using unprotected peptides. In this Example such a strategy is demonstrated based on the domain ligation strategy [4] for intramolecular amide cyclization and the development of a new resin support to attain its application.

Results and Discussion

A key functional group in the domain ligation strategy of the present invention is the $C^{\alpha}$-ester glycoaldehyde 5. To provide such an ester aldehyde by solid phase synthesis a resin 3 was developed by linking a Fmoc Gly glyceric ester 1 to a benzaldehyde-polystyrene resin 2 [5] through an acetal handle (Scheme 2, below). The synthesis of the desired peptide was then performed using Fmoc-terbutyl chemistry with a N-terminal Cys containing S-terbutyl protecting group. Cleavage by TFA released the peptide ester diol 4. Oxidation with $NaIO_4$ generated the corresponding aldehyde 5. Deprotection of the S-terbutyl using $PBu_3$ at controlled pH gave the cyclized Peptide 6 in excellent yield. The neutralizing determinant of the V3 loop of gp 120 of HIV-1 containing the sequence PGRAFG SEQ ID NO:34 was used as a model. The linear peptide CGRAFG-$C^{\alpha}$-ester-diol SEQ ID NO:35 was obtained by Solid Phase Synthesis on resin 3. Cyclization at pH 4.5, as described in Scheme 2, below, gave the cyclic thiazolidine peptide ester 6 as a diasteroisomer. The amide bond formation was effected through an intramolecular O,N acyl transfer reaction 7, after adjusting the pH to 5.5. The reaction was completed in 4 days and afforded the cyclic peptide amide 8 in quantitative yield.

The strategy described in the present Example offers several advantages including convenient synthesis and purification of the linear peptide precursor, and allows the synthesis of large and complex cyclopeptides.

Scheme 2

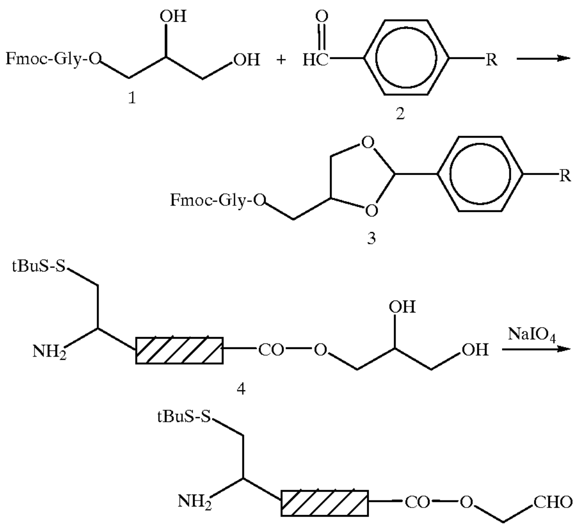

1 2 3 4 5

-continued

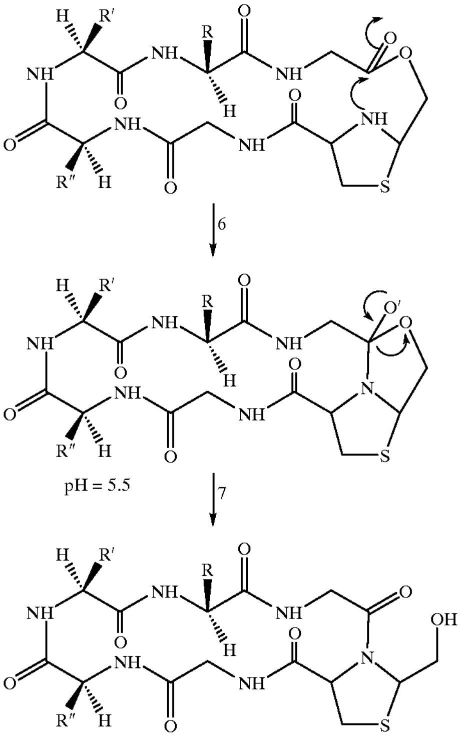

8

Synthesis of linear peptide precursor containing C-glycolaldehyde and cyclization to obtain an end-to-end cyclic peptide.

The following is a list of publications for this Example only:

1. Byk. G. and Gilon C. , J. Org. Chem 57 (1992) 5687–5692
2. Schiller, P. W., In The Peptides, Undenfriend, S. and Meienhofer, J.,(Eds) Academic Press, 1984, Vol. 6, p.254–268
3. Kaljuste K. and Unden A., Int. J. Peptide Protein Res., 43 (1994) 505–511
4. Liu C. F., and Tam J. P., J. Am. Chem. Soc. 116 (1994) 4149–41535
5. Frechet J. M. and Schuerch C., J. Am. Chem. Soc. 93 (1971) 492–496

EXAMPLE 18

Orthogonal Incorporation of Cyclic Peptides as Multiple Antigens Attached to Dendrimeric Cores The present Example outlines a general method for the synthesis of cyclic peptides in order to develop a new and wide ranging strategy for the formation of constrained peptides, and their use as building blocks for peptide dendrimers and unprotected proteins. The method is based on the Domain Ligation Strategy [1,2] where an intramolecular covalent bond is formed between a weak base and an aldehyde to give a cyclic oxime, oxazolidinone or thiazolidine. Such cyclizations would expand the conventional repertoire of disulfide or lactam formation. The reaction may be performed on a resin [3], or an unprotected linear peptide precursor may be cyclized in aqueous solution. Utilizing two weak bases it is possible to cyclize the peptide and to assemble the constrained peptides onto branched templates to investigate modifications in vaccine design and delivery.

Methods, Results and Discussion

Linear precursors (Scheme 3, below) were synthesized on a Wane resin using standard Fmoc chemistry and BOP activation. The lysine residue was introduced as Dde-Lys (Fmoc)-OH [4] and Boc-Ser(tBu)-OH coupled to the side chain.

For oxime cyclization, the peptide was cleaved from the resin to give the linear unprotected peptide precursor 1. Using sodium periodate at pH 7 an aldehyde was obtained [5] as the α-oxoacyl moiety 2 which spontaneously cyclized in >90% yield to give the cyclic oxime 3. The reaction, followed by HPLC, was complete within 2 minutes.

Similar results were obtained for thiazolidine formation when Z=Cys(StBu). Cys(StBu) was stable to the $NaIO_4$-mediated oxidation of serine (X=Ser, Scheme 3, below) to form the α-oxoacyl derivative. The StBu was then removed by a water soluble phosphine derivative at pH 5.5 and the resulting 1,2-aminothiol cyclized by thiazolidine formation. Cyclization was also accomplished on a resin where X=acetal [3]. Cys was deprotected with base and the acetal with mild acid. Following cyclization in DMF the peptide was cleaved from the resin to give the desired constrained peptide in 20% yield.

Finally, a 1,2-aminothiol in the presence of a hydroxylamine(4), would allow orthogonal cyclizations. The peptide can be first cyclized by oxime formation and then the thiol released by reduction of the S-t-butylsulphenyl. Control of the pH conditions then allow the 1,2-aminothiol to displace the hydroxylamine from the oxime to give a cyclic thiazolidine. The resulting hydroxylamine is now available for further condensation reactions with other peptide fragments containing aldehyde moieties. In this way constrained "building blocks" can be assembled on various dendrimeric cores to form multiple antigen peptides (MAPS).

Scheme 3

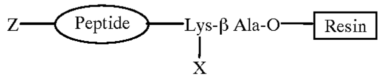

Aqueous cyclisation: Z = $H_2NOCH_2CO$, Cys(StBu), X = Serine
Resin cyclisation: Z = Cys(Fm), X = $(CH3O)_2CH(CH_2)_nCO$
Peptide sequence: GIGPGRAFG

1

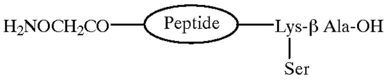

2

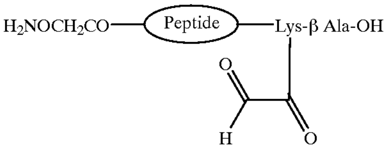

3

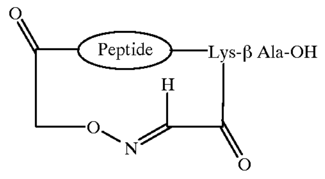

4

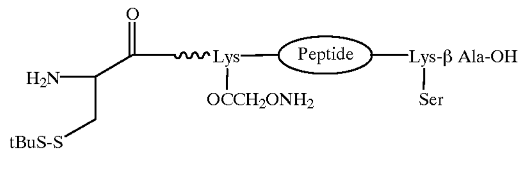

-continued

The formation of cyclic oximes and thiazolidines

The following is a list of publications for this Example only:

1. Liu, C-F and Tam, J. P., J. Am. Chem. Soc., 116 (1994) 4149.
2. Shao, J. and Tam, J. P., 3. Am. Chem. Soc., 117 (1995) 3893.
3. Chiang, L.-C., Cabezas, E., Calvo, J. and Satterthwait, A. C., In Hodges, R. S and Smith, J. A, (Eds) Peptides: Chemistry, Structure and Biology (The proceedings of the 11th American Peptide Symposium), Escom, Leiden, The Netherlands, 1994, p278.
4. Bycroft, B. W., Chan, W. C., Chhadra, S. R.,Hone, N. D., J. Chem. Soc. Chem. Comm., (1993) 778.
5. Rose, K., J. Am. Chem. Soc., 116 (1994) 30.

EXAMPLE 19

Entropy-driven Amide bond Ligation of Unprotected Peptide Segments for the Synthesis of HIV-1 Protease Analogs The present Example describes a side-chain initiated approach involving a capture-rearrangement strategy to the ligation of unprotected peptide segments in which the focus of the first bond formation is not directed to the α-amine, but rather between the amino segment side chain and the acyl segment (7, 8). In this approach, the amide bond is formed in two steps. First, it involves a capture step to form a non-amide bond, the thiazolidine (Thz) ring initiated by an addition reaction of the N-cysteinyl side chain of the amine segment to an ester aldehyde of the acyl segment at acidic pH. This also brings the p-amine close to the acyl segment, therefore increase their effective molar concentration. Second, the reactive carboxyl and amino termini in close proximity are positioned for spontaneous peptide bond formation through an entropy-driven intramolecular acyl transfer (7–11). Moreover, a thioproline (SPro) structure is formed at the ligation site which can be viewed as a proline surrogate (FIG. 30). This strategy obviates the need for protecting groups and overcomes the slow kinetics of conventional peptide bond formation. In the instant Example, the refinement and application of this chemoselective ligation strategy for the syntheses of three 99-residue HIV-1 protease analogs is described. These syntheses would provide a stringent test for this entropy-driven ligation approach and demonstrate the suitability of a thioproline as a replacement for Pro in protein synthesis.

Materials and Methods

Analytical HPLC was run on a Shimadzu system with a Vydac column (0.46 cm×25 cm, C18 reversed phase) at a flow rate of 1.5 ml/minutes with a linear gradient of buffer B (60% acetonitrile in $H_2O$/0.04% TFA) in buffer A (5% acetonitrile in $H_2O$/0.045% TFA), with UV detection at 225 m. Mass spectra were obtained with the Matrix-Assisted Laser Desorption Mass Spectrometry (MALDMS) with an accuracy of ±0.05%–0.1%. The calculated mass units were given as average values of the isotopic composition.

Recombinant HIV-1 PR was purchased in its highest grade, the affinity-purified, crystallizable grade from BACHEM Bioscience Inc., Switzerland. This material gave a $k_{cat}$≈6.9 $S^{-1}$ toward substrate IV at 37° C. Acetyl-pepstatin was also from the same company. All HIV-1 PR substrates were purchased from BACHEM Calif.

Snthesis of HIV-1 PR(1-37)-$S(CH)_2CO$-Gly-OH (1a) and [$Cys^{39}$, $Abu^{67,95}$]-HIV-1 PR (39–99) (Id). Both the thioester segment, FIG. 30, step a, and amine segment, FIG. 30, step d, were prepared by solid phase synthesis (12) using the conventional Boc-Benzyl type protection strategy and the BOP coupling protocol (13). FIG. 30, step a was synthesized on an $Asn^{37}$-$S(CH_2)_2CO$-Gly-$OCH_2$-Pam resin which was obtained through coupling of Boc-Asn-$S(CH_2)_2COOH$ to H-Gly-$OCH_2$-Pam resin as reported (6). FIG. 30, step d was synthesized on a $Phe^{99}$-$OCH_2$-Pam resin (14). The final cleavage was performed using the low-high HF cleavage procedure (15). After HF cleavage, the crude products were extracted with 50% AcOH/H,O and dialyzed against decreasing concentrations of AcOH to 10%, then purified by preparative HPLC with a Vydac $C_{18}$ column. The purified products gave a single peak in analytical RP HPLC (FIG. 31A and D, peak 1 and 4 respectively). MS $[M+H]^+$, m/z (FIG. 30, step a) 4281.8(calc.), 4282.0 (found); m/z (FIG. 30, step d) 6529.7(calc.), 6530.0 (found).

Preparation of α-aminoacyloxy and amido acetaldyde dimethyl acetal. α-aminoacyloxyacetaldyde dimethyl acetal was prepared by reaction of the Z-protected α-amino acid cesium salt with bromoacetaldehyde dimethyl acetal in DMF followed by catalytic hydrogenolysis as reported previously (7, 8). α-Aminoacylamidoacetaldehyde was prepared by coupling of Z-amino acid to aminoacetaldehyde dimethyl acetal followed by catalytic hydrogenolysis.

Aldehyde introduction. The thioester segment, FIG. 30, step a, was dissolved in DMSO (5–10 mM) containing 0.5–1.0 M of the small amino component, α-aminoacyloxy (or amido)acetaldehyde dimethyl acetal and HOSu (0.5–1.0 M) and $AgNO_3$ predissolved in DMSO (2 equivalents to the thioester segment) was added. In general, the reaction was completed in 20–60 minutes with a >80% yield as determined by HPLC. MS $[M+H]^+$, HIV-1 PR(1-38)-$OCH_2CH(CH_3)_2$, m/z 4337.9 (calc.), 4338.0 (found); $[Ala^{38}]$-HIV-1 PR(1–38)-$OCH_2CH(CH_3)_2$, m/z 4296.8 (calc.), 4296 (found); HIV-1 PR (1–38)-$NHCH_2CH(CH_3)_2$, m/z 4336.9 (calc.), 4338.0 (found).

The acetal deprotection was performed using 95% trifluoroacetic acid in $H_2O$ at 0° C. for 5–10 minutes to give the desired acyl segment of (1–38)-$XCH_2CHO$, 1c (FIG. 31C). The reaction mixture was immediately diluted with 10-fold 30% acetonitrile/$H_2O$ and applied immediately to an HPLC column for purification. The collected fractions were concentrated by a centrifuge vacuum and used immediately for the next step.

Ring formation and acyl transfer. The amine segment, $[Cys^{39}, Abu^{67.95}]$-HIV-1 PR (39–99), FIG. 30, step d, was dissolved in a minimal amount of 60% acetonitrile/$H_2O$ (0.1% TFA) and mixed with the above acyl segment containing a glycolaldehyde ester, FIG. 30, step c, and the solution was diluted with $H_2O$ (0.1% TFA) to the desired concentrations of the two segments (~50 mM for FIG. 30, step c and ~100 mM for FIG. 30, step d). Acetyl-pepstatin (0.5 mM) and EDTA (0.5 mM) were then added. The pH was adjusted by addition of solid sodium acetate to 3.0–4.0 (by pH paper). The thiazolidine ring product, FIG. 30, step e, was formed in 60–80% (by HPLC) in 5–10 hours based on the acyl segment of glycolaldehyde ester (the amino segment was used in 2–3 equivalents). The ring formation would be faster at higher pH as previously studied, but in the case of HIV-1 protease higher pH led to precipitation of both segments. Some precipitation (mostly of the ligation product) was indeed observed during the reaction which was dissolved by guanidine HCl before HPLC purification. The ligation product was isolated by HPLC, lyophilized and redissolved in the denaturing condition of 6 M guanidine HCl (pH 5.5)140% glycerol (v/v)solution to complete the O,N-acyl transfer reaction. The protein concentration was determined by UV spectroscopy in its 6 M Guanidine HCl solution prior to addition of glycerol using a $\epsilon_{280}=25{,}000$ $M^{-1}.cm^{-1}$ (16). This concentration then served as basis for determination of enzymatic activities and for calculation of kinetic parameters such as $k_{cat}$, assuming that 100% of the material was retained and remained active until enzymatic assay. The guanidine/glycerol solution served as a storage buffer for the protease and preserved enzymatic activity. More than 90% of the rearranged N-acyl product, FIG. 30, step f, was formed after 34 days incubation in the above buffer. Because of the large size of HIV-1 protease, the rearranged N-acyl product was indistinguishable from the unarranged O-acyl product by HPLC. However, studies on small model compounds and peptides have determined that the O,N-acyl transfer reaction occurred at an optimal pH of around 5 with a $t_{1/2}$ of about 20 hours (7, 8). These enzyme solutions were stored in freezer at −70° C. The enzyme sample was active immediately when diluted into the assay buffer as shown by the hydrolysis of the synthetic peptides derived from the HIV Gag protein sequences FIG. 33. MS $[M+H]^+$, $[SPro^{39}, Abu^{67.95}]$-HIV-1 PR (monomer), m/z 10803 (calc.), 10805 (found); $[Ala^{38}, SPro^{39}, Abu^{67.95}]$-HIV-1 PR, m/z 10761 (calc.), 10764 (found); [Leu-$NHCH_2$-$Thz^{38-39}$, $Abu^{67.95}$]-HIV-1 PR, m/z 10802 (calc.), 10806 (found).

HPLC analysis of the enzymatic hydrolysis of HIV-1 PR substrates by the synthetic protease analogs. Three different synthetic substrates derived from the Gag p17/p24 and p24/p15 cleavage sites were used for qualitative HPLC assays: H-Val-Ser-Gln-Asn-Tyr-Pro-Ile-Val-OH (substrate VIII SEQ ID NO:36) from the natural p17/p24 cleavage site, H-Lys-Ala-Arg-Val-Nle-Phe(p-$NO_2$)-Glu-Ala-Nle-$NH_2$ SEQ ID NO:37 (substrate IV) and 2-aminobenzoyl-Thr-Ile-Nle-Phe(p-$NO_2$)-Gln-Arg-$NH_2$ SEQ ID NO:38 (17) derived from the two p24/p15 cleavage sites. Synthetic protease analogs efficiently catalyzed the hydrolysis of these substrates preferably in a weakly acidic buffer. Typically, for HPLC assay, an aliquot of protease analog solution in 6 M guanidine HCl/40% Glycerol was directly added to an appropriate assay buffer with a substrate for an indicated time period at 22° C. and stopped with 20% TFA/$H_2O$ before applied to HPLC column (FIG. 33). The hydrolysis products were collected from analytic HPLC and confirmed by MS analysis.

Kinetic studies. Substrate IV, derived from the first cleavage site of the Gag p24/p15 (18), was used for all kinetic studies due to its excellent solubility in aqueous buffer. Assay buffer was 50 mM sodium acetate, pH 4.7, containing 5 mM DTT and 2 mM EDTA, with an ionic strength equal to 1 M NaCl and with glycerol added to 10% (v/v). DTT and EDTA were added to prevent the oxidation of the free $Cys^{67.95}$ residues in the recombinant HIV-1 protease. For comparison, this buffer was used for all kinetic studies. The enzyme sample was activated by simple dilution into the assay buffer. No further refolding/dialysis procedure was employed. The enzyme concentration typically used for kinetic assays was 0.02 μM to 0.05 μM and that of the substrate was between 5 μM and 60 μM. The reaction proceeded for 3 to 6 minutes during which less than 25% of the substrate was hydrolyzed and was stopped with 20% TFA in $H_2O$. Initial rates were calculated based on the UV absorption (area of HPLC peaks) at 225 nm of the substrate and hydrolyzed products (the ratio of UV absorption of the substrate to that of the hydrolyzed second half, H-Phe(p-$N_2O$)-Glu-Ala-Nle-$NH_2$ SEQ ID NO:39 was determined to be 1:0.68), calibrated in the presence of internal standards. Typically, five to six data points were used for each experiment. Kinetic parameters were obtained by fitting data into the Michaelis-Menten equation using the Lineweaver-Burk plotting method. All of the kinetic studies were performed at 22° C. Catalytic hydrolysis was significantly faster at higher temperatures.

Results

Overall synthetic scheme. HIV-1 protease (HIV-1 PR), a member of the aspartic protease family, is a homodimer in which each of the 99-residue monomers contributes one of the two aspartic acid residues to constitute the active site of the enzyme (19–23). Two proline residues are suitable for our ligating sites: $Pro^{39}$ at the broad loop (sequence 36–42) prior to the flap region and $Pro^{44}$ located within the first strand of the flap. In this study, $Pro^{39}$ was chosen as the ligating site to accommodate the pseudoproline structure. Because the $Cys^{67.95}$ are not involved in disulfide bridges, the strategy of Wlodawer et al. (23) was used and replaced these Cys residues with α-aminobutyric acid to give [$SPro^{39}$, $Abu^{67.95}$]-HIV-1 PR. Two other analogs, $Leu^{38}$→Ala, [$Ala^{38}$, $SPro^{39}$, $Abu^{67.95}$]-HIV-1 PR and a $Leu^{38}$-amidomethyl-$Thz^{39}$ analog with a non-peptide backbone, [Leu-$NHCH_2$-$Thz^{38-39}$, $Abu^{67.95}$]-HIV-1 PR, were also prepared.

The overall strategy for the syntheses of these HIV-1 protease analogs consists of ligating two unprotected segments: the (1–38)-acyl and the (39–99)-amine segments (FIG. 30). For the side-chain initiated capture, a glycolaldehyde ester (acyloxyacetaldehyde) was designed on the acyl segment to form a thiazolidine ring with an N-terminal cysteine of the amino segment. This reaction is highly chemoselective because it is performed under acidic condition to exclude other functional groups from the reaction. The ring formation brings together the carboxyl and amino components by a covalent structure allowing proximity-driven O,N-acyl transfer to form the amide bond.

Preparation of acyl segment bearing glycolaldehyde ester. The acyl glycolaldehyde ester was prepared by adding a single amino acid derivative, a $leucinyl^{38}$ methyl acetal masked glycolaldehyde (Leu-oxyacetaldehyde dimethyl acetal), onto the (1–37)-acyl segment containing a $C^{\alpha}$-thioester. Activation of thioester by $Ag^{+}$ (6) in the presence of a large excess of the masked $Leu^{38}$-oxyacetaldehyde efficiently yielded the (1–38)-acyl segment, FIG. 30, step b and FIG. 31B. No side reactions with other amines and nucleophiles were detectable because of their relatively low molar ratio when compared to the large excess of the small $Leu^{38}$-component.

The masked amino acid glycolaldehyde ester was previously introduced by enzymatic methods (7, 8). However, the chemical method via $Ag^{+}$ is more versatile because it overcomes the limitations imposed by the substrate specificity of an enzymatic reaction. This chemical activation was a crucial step to the successful synthesis of HIV-1 PR analogs. Because the formation of a peptide bond in a chemical synthesis always involves activation of a $C^{\alpha}$-COOH and its subsequent coupling to an α-amine, the silver ion distinguished the $C^{\alpha}$-thioester from other side-chain unprotected carboxylic groups to give an activated acyl segment. The selectivity and efficiency of the coupling step was driven by the overwhelming excess of the small amino acid derivative of the masked glycolaldehyde. This chemical activation method is also useful in introducing different functionalities onto an unprotected peptide for other site-specific modification purposes. For purposes of the present Example, the $Ala^{38}$ analog was prepared using the masked Ala-oxyacetaldehyde and the $Leu^{38}$-amidomethyl-$Thz^{39}$ analog by the masked Leu-amidoacetaldehyde. The latter is an isosteric but stable analog of the intermediate ester product prior to intramolecular acyl rearrangement and provides an opportunity to compare the rearranged with the unrearranged product. Treatment of the obtained acetal, FIG. 30, step b, by TFA at low temperature quickly released the free aldehyde, FIG. 30, step 1c. The demasked aldehyde could give side products in the case of HIV-1 PR segments as revealed by HPLC if longer reaction time and/or higher temperature was applied, although it was found to be quite stable in previous cases (7, 8).

Ligation of the amine and acyl segments. Ligation between unmasked acyl segment (1–38) containing a glycolaldehyde, FIG. 30, step c, and [$Cys^{39}$]-amine segment, FIG. 30, step d, immediately gave the HIV-1 PR thiazolidine product FIG. 30, step e. This ring formation was efficient and 80% was completed within 5 hours at pH 4 (FIG. 31E) under optimal conditions even when the concentrations of both segments were low (0.05–0.2 mM). It was such high reactivity that provided the driving force to overcome the entropy barrier of the conventional intermolecular reaction between large peptide molecules. The high efficiency could be attributed to the high chemoreactivity of an aldehyde with 1,2-aminothiol and it could also be attributed possibly to the complementarity between the two structurally folded unprotected peptides of the HIV-1 PR. Such complementarity is usually not possible for protected peptide segments and points to the unique advantage of using unprotected peptide segments as building blocks in our strategy. This ring forming reaction has also found its application in the preparation of large peptide dendrimers with high density (24).

Unlike the conventional method, the strategy outlined in the present Example generates an active product because the O,N-acyl transfer reaction also occurs at acidic condition and is the slow step in our scheme (7, 8). This greatly simplifies the scheme by eliminating the harsh deprotection and the necessity of the refolding steps. In the synthesis of the instant Example, autoproteolytic cleavages (25) of synthetic HIV-proteases and degradation of synthetic segments occurred almost immediately. To prevent enzymatic cleavages, an aspartic protease inhibitor, acetyl-pepstatin which has been shown to inhibit the HIV-1 protease at a $K_i$=20 mM, was added to the ligation solution. The product obtained after HPLC purification was further incubated in 6 M guanidine HCl (pH 5.5)/glycerol solution for 3–4 days to assure the completion of the O,N-acyl transfer. All the three analogs were prepared in a similar way except for $Leu^{38}$-amidomethyl-$Thz^{39}$, which did not involve an acyl rearrangement. All three protease analogs were analyzed by MALDMS, which gave the expected molecular weight. For example, the [$SPro^{39}$, $Abu^{67,95}$]-HIV-1 PR gave a mass unit of 10,805 that agreed closely with the calculated mean unit of 10,803 (FIG. 32).

Enzymatic activity of the synthetic HIV-1 PR analogs. HPLC analysis was performed to determine whether these synthetic protease analogs were active against the HIV-1 PR substrates. As shown in FIG. 33, these HIV-1 PR analogs were active in catalyzing the hydrolysis of three different substrates. Further kinetic studies (Table 11) showed that these protease analogs exhibited similar binding affinity ($K_m$), as the native enzyme, to the Gag p24/p15 synthetic peptide substrate (substrate IV) (FIG. 33C) but showed different catalytic activity ($k_{cat}$): 100% with [$SPro^{39}$, $Abu^{67.95}$]-HIV-1 PR, ~70% with $Ala^{38}$ and ~30% with the $Leu^{38}$-amidomethyl-$Thz^{39}$ analog.

TABLE 11

Kinetic parameters of the synthetic HIV-1 PR analogs on the hydrolysis of substrate IV in comparison with recombinant HIV-1 PR

| Protease | $K_m$, μM | $k_{cat}$, $S^{-1}$ | $k_{cat}/K_m$, $M^{-1}$, $S^{-1}$ |
|---|---|---|---|
| rHIV-1 PR | 10.1 | 1.23 | $1.21 \times 10^5$ |
| [$SPro^{39}$,$Abu^{67,95}$]-HIV-1 PR | 11.9 | 1.42 | $1.19 \times 10^5$ |

TABLE 11-continued

Kinetic parameters of the synthetic HIV-1 PR analogs on the hydrolysis of substrate IV in comparison with recombinant HIV-1 PR

| Protease | $K_m$, $\mu M$ | $k_{cat}$, $S^{-1}$ | $k_{cat}/K_m$, $M^{-1}$, $S^{-1}$ |
|---|---|---|---|
| [$Ala^{38}$,$SPro^{39}$,$Abu^{67,95}$]-HIV-1 PR | 8.2 | 0.81 | $9.84 \times 10^4$ |
| [Leu-$NHCH_2$-$Thz^{38-39}$,$Abu^{67,95}$]-HIV1-PR | 11.4 | 0.41 | $3.63 \times 10^4$ |

Kinetic studies were performed at 22° C. under steady state conditions and substrate hydrolysis was analyzed by RP HPLC. See Materials and Methods for experimental details.
$k_{cat}$ was calculated from $V_{max}$, using an enzyme concentration measured by UV spectrophotometry (16). The estimated accuracy of each experiment was within the range of ±5–15%.

The $K_{cat}$ values obtained for the native enzyme as well as for our synthetic analogs in this study are lower than some recently reported data in the literature determined by continuous spectrophotometric approaches (26, 27). This may result from different assay conditions. For example, the assay temperature (22° C.) in our study was lower than that (37° C.) usually used by others. One other reason may be due to the way that the enzyme concentration was determined. In this experiment, UV absorption was used, rather than active site titration, to determine enzyme concentration in its denatured solution in assuming that all the material would be refolded to the active form when diluted in the assay buffer, which usually leads to overestimation of the actual active concentration. However, provided the assay procedures and conditions were parallel for each of the enzyme samples tested in this Example, the obtained data would provide a reasonable basis for comparison.

It is not surprising that [$SPro^{39}$, $Abu^{67.95}$]-HIV-1 PR retained activity as full as the native enzyme because hydroxymethyl thioproline is structurally close to the normal Pro residue. The epimeric hydroxymethyl group is on the side chain Pro ring and would not change the overall backbone conformation of a Proline-containing peptide chain. In the $Ala^{38}$ analog, the change of the isobutyl side chain to a methyl may result in loss of hydrophobic interaction. This loss leads to an increase in the activation energy for the catalytic hydrolysis and accounts for the decrease in this analog's catalytic activity. In the case of $Leu^{38}$-amidomethyl-$Thz^{39}$ analog, there are three atoms inserted between the natural $Leu^{38}$ C═O and $Pro^{39}$ >NH and this nonpeptide backbone may cause conformational distortion. Surprisingly, this analog still exhibited about 30% activity and comparable binding affinity toward substrate IV. The relatively flexible structure of the broad loop (22, 23) apparently can tolerate this structural modification.

These results show that the protease analogs with a pseudoproline structure in the sequence were able to fold, dimerize correctly into its active conformation, and retain nearly full catalytic activity. It is also interesting to note that the HIV-1 protease analogs of the present Example already acquired certain enzymatic activity at their O-acyl ester stage as one can deduce from data on the $Leu^{38}$-$NHCH_2$-$Thz^{39}$ analog. However, the O,N-acyl transfer was necessary to render the analogs fully active. These findings confirmed that the SPro structure has the same inducing effect on the refolding of the protein backbone as the natural Pro residue.

Discussion

The focus of the strategy described in the present Example on the side-chain nucleophile capture for the initial bond formation is an important contributing factor in the use of unprotected peptide segments because all amines are protonated and excluded from this phase of the reaction. The subsequent entropy-driven amide bond formation by intramolecular acyl transfer is naturally observed in the post-translational protein splicing (28–30) in which the ultimate excision of an intervening sequence involves an N,O(S)-acyl transfer between the amide and ester linkages of Ser, Thr, or Cys residue. Similar N,O-acyl interconversions are observed in peptides with Gly-Ser/Thr sequences in strongly acidic and mild basic conditions (31). Thus, the ester formation of an acyl component with the side chains of Ser, Thr, or Cys in the amine component leads to amide bond formation through the proximity-driven O(S),N-acyl transfer. This principle was first put into practice for peptide synthesis by Kemp et al. (9, 10) and was recently adopted by us (7, 8) and Dawson et al. (11). In general, there are three strategies that utilize the proximity-driven principle besides the conformation-assisted approaches (32–34). First, Kemp used a tricyclic aromatic template containing an acyl-ester-acyl-thiol to capture an activated cysteinyl side chain through a disulfide exchange to place both the p-amine and acyl component in close proximity to effect the amide bond formation. The tricyclic template is then removed by reduction (9, 10). Second, as shown in this work, the strategy described above uses a side-chain directed strategy to capture an acyl segment containing an aldehyde group (7, 8). The third strategy uses either thioester or disulfide exchange without template to facilitate the proximity-driven S,N-acyl transfer. Dawson et al. have developed a thioester exchange between an acyl thioester and a cysteinyl segment (11) while we have developed a similar scheme through a phosphine-assisted reaction. A more facile disulfide exchange strategy through an acyl thiocarboxylic acid and an activated unsymmetrical disulfide of the N-Cys amino segment has also been developed by the inventors. A common theme among these strategies is the use of the N-Cys side chain for initial attack to form a covalent bond between the acyl and the side-chain of the amine segment and then an entropy-driven amide bond formation. Unlike the strategy of Kemp et al. (9, 10) or Dawson et al. (11), which produces a cysteine residue at the ligation site, the strategy described in the present Example produces a proline-like backbone that may have the advantage of being more accessible because of the high frequency of proline residues recurring mostly at reverse turns in protein sequences. Furthermore, by varying the aldehyde moiety, other non-genetically coded amino acids can be generated. The thiazolidines are also reversible to give cysteinyl bonds. Such chemical approaches, together with the recently developed enzymatic method (35), represent an important advance in the synthesis of proteins by non-genetic ways.

With large unprotected peptide segments and protein domains readily accessible either by solid phase synthesis or recombinant techniques, a chemical ligation method to form an amide backbone between these high molecular-weight building blocks would greatly expand the ability of one skilled in the art to synthesize and modify proteins with non-coded amino acids as well as to design artificial proteins with unusual architectures (36, 37). The syntheses of HIV-1 protease analogs clearly demonstrate the ease and efficiency of our chemical ligation approach. Moreover, the instant method demonstrates that a pseudoproline structure can be used to replace a proline residue in the sequence of a protein without altering its biological activity. Most importantly, this strategy employs the principle of chemoselectivity of the side-chain participation in the initial formation of a covalent complex and the subsequent intramolecular acyl transfer to overcome the problems of the conventional segment condensation method. In the future, it should open new avenues for other chemical approaches in forming peptide bonds between very large peptide segments.

The following is a list of publications for the present Example only:

1. Hirschmann, R., Nutt, R. F., Veber, D. F., Vitali, R. A., Vary, S. L., Jacob, T. A., Holly, F. W. & Denkewalter, R. C. (1969) *J. Am. Chem. Soc.* 91, 507–508.
2. Kiyama, S., Fujii, N., Yajima, H., Moriga, M. & Takagi, A. (1984) *Int. J. Pept. & Protein Res.* 23, 174–186.
3. Kuroda, H., Chen, Y.-N., Kimura, T. & Sakakibara, S. (1992) *Int. J. Pept. & Protein Res.* 40, 294–299.
4. Blake, J. and Li, C. H. (1981) *Proc. Natl. Acad. Sci. USA* 78, 4055.
5. Yamashiro, D. and Li, C. H. (1988) *Int. J. Pept. Protein Res.* 31, 322.
6. Hojo H. and Aimoto S.(1991) *Bull. Chem. Soc. Jpn.* 64, 111.
7. Liu, C.-F. and Tam, J. P. (1994) *J. Am. Chem. Soc.* 116, 4149.
8. Liu, C.-F. and Tam, J. P. (1994) *Proc. Natl. Acad. Sci. USA* 91, 6584–6588.
9. Fotouhi, N., Galakatos, N. G., Kemp, D. S. (1989) *J. Org. Chem.* 54, 2803.
10. Kemp, D. S. and Carey, T. I. (1993) *J. Org. Chem.* 58, 2216.
11. Dawson, P. E., Muir, T. W., Clark-Lewis, I. & Kent, S. B. H. (1994) *Science* 266, 776–779.
12. Merrifield, R. B. (1963) *J. Am. Chem. Soc.* 85, 2149–2154.
13. Castro, B., Dormoy, J. R. G., Evin, G. & Selve, C. (1975) *Tetrahedron Lett.* 1219–1222.
14. Mitchell, A. R., Kent, S. B. H., Engelhard, M. & Merrifield, R. B. (1978) *J. Org. Chem.* 43, 28452852.
15. Tam, J. P., Heath, W. F. & Merrifield, R. B. (1983) *J. Am. Chem. Soc.* 105, 6442–6455.
16. Baca, M. and Kent, S. B. H. (1993) *Proc. Natl. Acad. Sci. USA* 90, 11638–11642.
17. Toth, M. V. & Marshall, G. R. (1990) *Int. J. Pept. & Protein Res.* 36, 544–550.
18. Richards, A. D., Phylip, L. H., Farmerie, W. G., Scarborough, P. E., Alvarez, A., Dunn, B. M., Hire, P.-H., Konvalinka, J., Strop, P., Pavlickova, L., Kostka, V. & Kay, J. (1990) *J. Biol. Chem.* 265, 7733–7736.
19. Debouck, C., Gorniak, J. G., Strickler, J. E., Meek, T. D., Metcalf., B. W. & Rosenberg, M. (1987) *Proc. Natl. Acad. Sci. USA* 84, 8903–8906.
20. Kohl, N. E., Emini, E. A., Schleif, W. A., Davis, L. J., Heimbach, J. C., Dixon, R. A. F., Scolnick, E. M. & Sigal, I. S. (1988) *Proc. Natl. Acad. Sci. USA* 85, 4686—4690.
21. Pearl, L. H. and Taylor, W. R. (1987) *Nature* (London) 329, 351–354.
22. Navia, M. A., Fitzgerald, P. M. D., McKeever, B. M., Leu, C., Heimbach, J. C., Herber, W. K., Sigal, I. S., Darke, P. L. & Springer, J. P. (1989) *Nature* (London) 337, 615–620.
23. Wlodawer, A., Miller, M., Jaskolski, M., Sathyanarayana, B. K., Baldwin, E., Weber, I. T., Selk, L. M., Calwson, L., Schneider, J. & Kent, S. B. H. (1989) *Science* 245, 616–621.
24. Rao, C. and Tam, J. P. (1994) *J. Am. Chem. Soc.* 116, 6975–6976.
25. Mildner, A. M., Rothrock, D. J., Leone, J. W., Bannow, C. A., Lull, J. M., Reardon, I. M., Sarcich, J. L., Howe, W. J., Tomich, C.-S. C., Smith, C. W., Heinrikson, R. L. and Tomasselli, A. G. (1994) *Biochemistry* 33, 9405–9413.
26. Tumnmino, P. J., Ferguson, D., Hupe, L. and Hupe, D. (1994) *Biochem. & Biophys. Res. Comm.* 200, 1658–1664.
27. Polgar, L., Szeltner, Z. and Boros, I. (1994) *Biochemistry* 33, 9351–9357.
28. Kane, P. M., Yamashiro, C. T., Wolczyk, D. F., Neff, N., Goebl, M. & Stevens, T. H. (1990) *Science* 250, 651–657.
29. Davis E. O., Jenner, P. J., Brooks, P. C., Colston, M. J. & Sedgwick, S. G. (1992) *Cell* 71, 201–210.
30. Hodges R. A., Perler, F. B., Noren, C. J. & Jack, W. E. (1992) *Nucleic Acids Res.* 20, 6153–6157.
31. Sakakibara, S., Shin, K. H., Schneider, W. & Hess, G. P. (1962) *J. Am. Chem. Soc.* 84, 4921–4928.
32. Homandberg, G. A. and Chaiken, I. M. (1980), *J. Biol. Chem.* 255, 4903.
33. Wallace C. J. A. and Corthasy B. E. (1986), *Protein Eng.* 1, 23.
34. Proudfoot, A. E. I., Rose, K., Wallace, C. J. A. (1989) *J. Biol. Chem.* 264, 8764–8770.
35. Jackson D. Y., Burnier, J., Quan, C., Stanley, M., Tom, J. & Wells, J. A. (1994) *Science* 266, 243.
36. Tam, J. P.(1988) *Proc. Natl. Acad. Sci. USA* 85, 5409–5413.
37. Mutter, M. and Vuilleumier, S. (1989) *Angew. Chem. Int. Ed. Engl.* 28, 535.

EXAMPLE 20

Intramolecular Acylation for Chemical Ligation of Large. Unprotected Peptide Segments Methods that utilize the proximity-driven intramolecular acylation as an alternative for the formation of peptide bonds (1–4) allow the intrinsic entropic barrier of the intermolecular peptide bond-forming process to be bypassed. Additionally, the need for protection is avoided due to the high chemoselectivity and regiospecificity of the reactions involved. A ligation method using an acyl glycoaldehyde ester for the capture with an $N^{\alpha}$-Cys-peptide and O,N-acyl transfer to generate a proline-like structure at the ligation site, developed by the inventors (2,3), has been successfully applied to the syntheses of several active analogs of the HIV-1 protease through ligation at an Xaa-Pro bond. The present Example describes a new ligation method in which the key step is the specific capture of the $C^{\alpha}$-thiol carboxylic acid of the first peptide by the activated side chain thiol of the Cys residue of the second peptide, thereby bringing the two reacting groups engaged in peptide bond formation into close proximity to allow fast intramolecular acylation through a 6-member ring transition state. The resulting S-sulfhydryl (S-SH) is then removed by reduction to give the native Cys residue at the ligation (scheme 4, below).

Results and Discussion

The first capture step involves a reaction used for the formation of unsymmetrical disulfides in peptide synthesis. The subsequent intramolecular acylation involving a 6-member ring intermediate is an extremely fast reaction and has not been exploited so far for peptide bond formation. Model studies have demonstrated the high efficiency of this ligation scheme. For example, reaction of Z-Gly-SH with TfapH-Cys(Npys)-Ala-OMe at pH 5–7 gave immediately Z-Gly-Cys(SH)-Ala-OMe. The intermediate acyl-disulfide was not detected because of the high rate of rearrangement. Z-Gly-Cys-Ala-OMe with a free SH was easily obtained by treating, Z-Gly-Cys(SH)-Ala-OMe with DTT or trialkyl phosphine. It is worthwhile to emphasize the high efficiency of this ligation scheme. In the syntheses of moderate to large peptides according to the present invention, it was determined that the reaction of a thiol carboxylic acid with a Npys- or Scm-modified thiol was extremely fast and completed almost Scheme 4

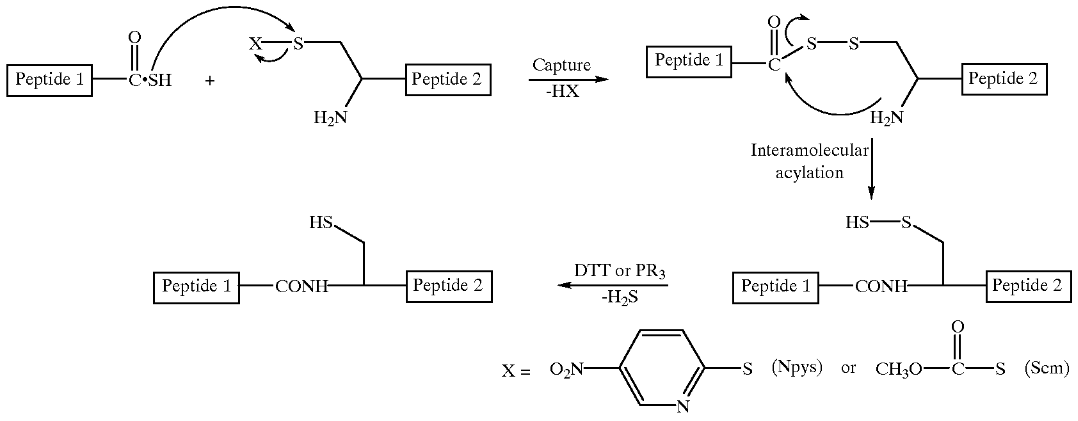

A chemical ligation scheme involving intramolecular acylation.

instantly upon mixture of the two components even at pH as low as 1.5–2, while the molar concentrations of the two components were in the micro molar range. This high reactivity is due both to the activated feature of a disulfide formed with the Scm or Npys groups and to the low pKa value of the thiol carboxylic acid. For the intramolecular acylation, the efficiency is due, first, to the close proximity of the α-acyl and α-amine and, second, to the activated feature of the α-acyl carbonyl once the acyl disulfide was formed (Scheme 4, above). The final reduction step was indispensable to afford the native Cys residue at the end of synthesis. Another interesting property of the S-SH product after rearrangement was its tendency to form tri- and tetra-sulfides through disulfide exchange and oxidation. However, these side products had no effect on ligation yield since they were all convened to the desired Cys product upon reduction. The efficiency and specificity of this strategy makes it an attractive approach for the synthesis of proteins involving ligation of very large unprotected peptide segments of which relative low molar concentrations are expected. Although it is strategically close to the thibl-capture scheme developed by Kemp et at. who used a tricyclic dibenzofuran template to mediate the O,N-acyl transfer (1), the method described in the present Example does not use a template, and is therefore a thiol-capture strategy in the simplest form.

The following is a list of publications for the present Example only:

1. Kemp et al., 1993, J. Org. Chem. 58:2216.
2. Liu and Tam, 1994, J. Am. Chem. Soc. 116:4149.
3. Liu and Tam, 1994, Proc. Natl. Acad. Sci. USA 91:6584.
4. Dawson et al., 1994, Science 266:776.

Thus, although there have been described particular embodiments and examples of the present invention, it is not intended that such references be construed as limitations upon the scope of this invention except as set forth in the following claims.

What is claimed is:

1. A method of forming an amide bond between a first molecule and a second molecule, said first and second molecule independently selected from the group consisting of an amino acid, peptide, peptide mimetic, peptide scaffolding matrix and protein, said method comprising coupling said first molecule to said second molecule by means of an acyl rearrangement reaction through a five to seven membered ring intermediate without aid of a template, said coupling selected from the group consisting of (A) a thioesterification reaction comprising reacting a thiocarboxylic acid on either said first molecule or said second molecule with a 1,2-aminohaloethane moiety on either said second molecule or said first molecule, respectively;

(B) a thioesterification reaction comprising reacting a thiocarboxylic acid on either said first molecule or said second molecule with a aziridine moiety on either said second molecule or said first molecule, respectively;

(C) a disulfide exchange reaction comprising reacting an acyl mixed disulfide on either said first molecule or said second molecule with a 1,2-aminothiol moiety on either said second molecule or said first molecule, respectively;

(D) a disulfide exchange reaction comprising reacting a thiocarboxylic moiety on either said first molecule or said second molecule with a 1,2-aminoethane moiety on either said second molecule or said first molecule, respectively;

(E) an N-acylation reaction comprising reacting a 1,2-aminoethane imidazole moiety on either said first molecule or said second molecule with an acyl mixed disulfide moiety on either said second molecule or said first molecule, respectively; and (F) an O-acylation reaction comprising reacting a 1,2-aminoethane carboxylic moiety on either said first molecule or said second molecule with an acyl mixed disulfide moiety on either said second molecule or said first molecule, respectively.

2. A method of forming an amide bond between a first molecule and a second molecule, said first and second molecule independently selected from the group consisting of an amino acid, peptide, peptide mimetic, peptide scaffolding matrix, and protein, said method comprising coupling said first molecule to said second molecule by means of an acyl rearrangement reaction through a five to seven membered ring intermediate without aid of a template, said coupling performed by an aldehyde capture reaction comprising reacting a weak base moiety on either said first molecule or said second molecule with an aldehyde moiety on either said second molecule or said first molecule, respectively.

3. The method of claim 1 wherein said forming an amide bond results in the formation of a circular peptide.

4. The method of claim 2 wherein said forming an amide bond results in the formation of a circular peptide.

5. The method of claim 1 or 2 wherein said peptide is selected from the group consisting of a long straight chain peptides, a branched chain peptides and a synthetic peptide.

6. The method according to claim 1 or 2, wherein the functional groups of said first molecule and said second molecule are minimally protected, partially protected, globally protected, or not protected.

7. The method according to claim 2, wherein said reaction of the weak base moiety with the aldehyde moiety is performed under acidic conditions.

8. The method according to claim 2, wherein the weak base moiety is selected from the group consisting of a 1,2-aminothiol of cysteine, a 1,2-aminoethanol of serine, a 1,2-aminoethanol of threonine, an aminooxyacetyl function, a mono-hydrazine succinyl function, a 4-hyrazinobenzoyl, and mixtures thereof.

9. The method of claim 2, comprising reacting two weak base moieties, one weak base moiety being β-functionalized with the other weak base moiety, on either the first molecule or the second molecule with an aldehyde moiety on either the second molecule or the first molecule, respectively.

10. The method according to claim 9, wherein said reaction of the weak base moieties with the aldehyde moiety is performed under acidic conditions.

11. The method according to claim 9, wherein one of the weak base moieties is an amino group.

12. The method according to claim 9, wherein the other weak base moiety is selected from the group consisting of amino, sulfhydryl, hydroxy, carboxamide, indole, imidazole, and mixtures thereof.

13. The method according to claim 11, wherein the carboxylic group is chemically ligated with the amino group by the interaction of the aldehyde with a 1,3-disubstituted α-amino acid of the formula

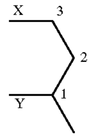

to form a 6-member ring of the formula

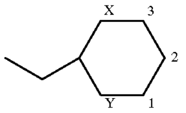

where X is

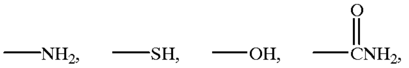

indole, imidazole, and Y is —$NH_2$, and where the substituent numbers correspond to the numbers set forth in the structures.

* * * * *

SEQUENCE LISTING

<160> NUMBER OF SEQ ID NOS: 41

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: synthetic
peptide

<400> SEQUENCE: 1

Cys Tyr Thr Ser Gly Cys Val Arg Ala Pro Thr Phe Asp Leu Lys
1 5 10 15

<210> SEQ ID NO 2
<211> LENGTH: 50
<212> TYPE: PRT
<213> ORGANISM: Artificial Sequence
<220> FEATURE:
<223> OTHER INFORMATION: Description of Artificial Sequence: synthetic
peptide -continued

<400> SEQUENCE: 2

```
Val Val Ser His Phe Asn Lys Cys Pro Asp Ser His Thr Gln Tyr Cys
  1               5                  10                  15

Phe His Gly Thr Cys Arg Phe Leu Val Gln Glu Glu Lys Pro Ala Cys
             20                  25                  30

Thr Cys His Ser Gly Tyr Val Gly Val Arg Cys Glu His Ala Asp Leu
         35                  40                  45

Leu Ala
     50
```

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: synthetic peptide

<400> SEQUENCE: 3

```
Cys Tyr Thr Ser Gly Cys Val Arg
  1               5
```

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: synthetic peptide

<400> SEQUENCE: 4

```
Cys Tyr Thr Ser Gly Cys Val Arg Ala
  1               5
```

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: synthetic peptide

<400> SEQUENCE: 5

```
Cys Thr Phe Asp Leu Lys
  1               5
```

<210> SEQ ID NO 6
<211> LENGTH: 32
<212> TYPE: PRT
<213> ORGANISM: Artificial Sequence
<220> FEATURE:
<223> OTHER INFORMATION: Description of Artificial Sequence: synthetic peptide

<400> SEQUENCE: 6

```
Val Val Ser His Phe Asn Lys Cys Pro Asp Ser His Thr Gln Tyr Cys
  1               5                  10                  15

Phe His Gly Thr Cys Arg Phe Leu Val Gln Glu Glu Lys Pro Ala Cys
             20                  25                  30
```

<210> SEQ ID NO 7
<211> LENGTH: 18
<212> TYPE: PRT
<213> ORGANISM: Artificial Sequence
<220> FEATURE:

-continued

<223> OTHER INFORMATION: Description of Artificial Sequence: synthetic peptide

<400> SEQUENCE: 7

Thr Cys His Ser Gly Tyr Val Gly Val Arg Cys Glu His Ala Asp Leu
1 5 10 15

Leu Ala

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence: synthetic peptide

<400> SEQUENCE: 8

Val Met Glu Tyr Lys Ala Arg Arg Lys Arg Ala Ala Ile His Val Met
1 5 10 15

Leu Ala Leu Ala
20

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: synthetic peptide
<223> OTHER INFORMATION: Phe is p-nitro
<223> OTHER INFORMATION: Xaa is norleucine

<400> SEQUENCE: 9

Thr Ile Xaa Phe Gln Arg
1 5

<210> SEQ ID NO 10
<211> LENGTH: 24
<212> TYPE: PRT
<213> ORGANISM: Artificial Sequence
<220> FEATURE:
<223> OTHER INFORMATION: Description of Artificial Sequence: synthetic peptide

<400> SEQUENCE: 10

Cys Asn Tyr Asn Lys Arg Lys Arg Ile His Ile Gly Pro Gly Arg Ala
1 5 10 15

Phe Tyr Thr Thr Lys Asn Ile Ile
20

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: synthetic peptide

<400> SEQUENCE: 11

Val Ser Gln Asn Tyr Pro Ile Val
1 5

<210> SEQ ID NO 12
<211> LENGTH: 9
<212> TYPE: PRT
<213> ORGANISM: Artificial Sequence -continued

```
<220> FEATURE:
<223> OTHER INFORMATION: Description of Artificial Sequence: synthetic
      peptide
<223> OTHER INFORMATION: Phe is p-nitro
<223> OTHER INFORMATION: Xaa is norleucine

<400> SEQUENCE: 12

Lys Ala Arg Val Xaa Phe Glu Ala Xaa
  1               5


<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 13

Cys Asn Tyr Asn Lys Arg Lys Arg Ile His Ile Pro Gly Pro Arg Ala
  1               5                  10                  15


<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 14

Ser Ser Gln Phe Gln Ile His Gly Pro Arg
  1               5                  10


<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 15

Cys Asn Thr Asn Lys Arg Lys Arg Ile His Ile Pro Gly Pro Arg Ala
  1               5                  10                  15


<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 16

Thr Met Lys Ala
  1


<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 17

Cys Ala Lys Ala
```

-continued

1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: synthetic
peptide

<400> SEQUENCE: 18

Cys Phe Lys Ala
1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: synthetic
peptide

<400> SEQUENCE: 19

Ser Ala Lys Leu
1

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: synthetic
peptide

<400> SEQUENCE: 20

Ala Pro Gly Gly Asn Cys Val
1 5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: synthetic
peptide

<400> SEQUENCE: 21

Ser Arg Asp Phe Gly
1 5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: synthetic
peptide

<400> SEQUENCE: 22

Gly Glu Arg Gly Ala Leu
1 5

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: synthetic -continued

```
      peptide

<400> SEQUENCE: 23

Ala Val Ser Glu Ile Asn Phe Met His Asn Leu Gly Lys His Leu Ser
  1               5                  10                  15

Ser


<210> SEQ ID NO 24
<211> LENGTH: 36
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 24

Pro Gly Thr Leu Trp Gln Arg Pro Leu Val Thr Ile Arg Ile Gly Gly
  1               5                  10                  15

Glx Leu Lys Glu Ala Leu Leu Asp Thr Gly Ala Asp Asp Thr Val Leu
             20                  25                  30

Glu Glu Met Asn
         35


<210> SEQ ID NO 25
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 25

Cys Asp His Ala Arg His Gly Phe Leu Pro Arg His Arg Asp
  1               5                  10


<210> SEQ ID NO 26
<211> LENGTH: 22
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 26

Cys Asp His Ala Arg His Gly Phe Leu Pro Arg His Arg Asp Thr Gly
  1               5                  10                  15

Ile Leu Asp Ser Cys Ala
             20


<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 27

Cys His Ser Gly Tyr Val Gly Ala Arg Cys Glu His Ala Asp Leu Leu
  1               5                  10                  15

Ala


<210> SEQ ID NO 28
<211> LENGTH: 8
```

-continued

<212> TYPE: PRT
<213> ORGANISM: Artificial Sequence
<220> FEATURE:
<223> OTHER INFORMATION: Description of Artificial Sequence: synthetic
peptide

<400> SEQUENCE: 28

Asx Pro Gly Gly Asn Ala Cys Val
1 5

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: synthetic
peptide

<400> SEQUENCE: 29

Cys Lys Phe Ala
1

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: synthetic
peptide

<400> SEQUENCE: 30

Ser Ala Lys Ala
1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: synthetic
peptide

<400> SEQUENCE: 31

Gly Ala Lys Ala
1

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: synthetic
peptide

<400> SEQUENCE: 32

Leu Ala Lys Ala
1

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: synthetic
peptide

<400> SEQUENCE: 33

Ser Ala Lys Leu Cys Pro Gly Gly Asn Cys Val

-continued 1 5 10

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: synthetic peptide

<400> SEQUENCE: 34

Pro Gly Arg Ala Phe Gly
1 5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: synthetic peptide

<400> SEQUENCE: 35

Cys Gly Arg Ala Phe Gly
1 5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: synthetic peptide
<223> OTHER INFORMATION: Xaa is norleucine

<400> SEQUENCE: 36

Val Ser Gln Asn Tyr Pro Ile Val
1 5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: synthetic peptide
<223> OTHER INFORMATION: Phe is p-nitro

<400> SEQUENCE: 37

Lys Ala Arg Val Xaa Phe Glu Ala Xaa
1 5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: synthetic peptide
<223> OTHER INFORMATION: Phe is p-nitro
<223> OTHER INFORMATION: Xaa is norleucine

<400> SEQUENCE: 38

Thr Ile Xaa Phe Gln Arg
1 5

<210> SEQ ID NO 39
<211> LENGTH: 4

-continued

```
<212> TYPE: PRT
<213> ORGANISM: Artificial Sequence
<220> FEATURE:
<223> OTHER INFORMATION: Description of Artificial Sequence: synthetic
      peptide
<223> OTHER INFORMATION: Phe is p-nitro
<223> OTHER INFORMATION: Xaa is norleucine

<400> SEQUENCE: 39

Phe Glu Ala Xaa
  1


<210> SEQ ID NO 40
<211> LENGTH: 99
<212> TYPE: PRT
<213> ORGANISM: HIV-1 PROTEASE

<400> SEQUENCE: 40

Pro Gln Ile Thr Leu Trp Gln Arg Pro Leu Val Thr Ile Arg Ile Gly
  1               5                  10                  15

Gly Gln Leu Lys Glu Ala Leu Leu Asp Thr Gly Ala Asp Asp Thr Val
             20                  25                  30

Leu Glu Glu Met Asn Leu Pro Gly Lys Trp Lys Pro Lys Met Ile Gly
         35                  40                  45

Gly Ile Gly Gly Phe Ile Lys Val Arg Gln Tyr Asp Gln Ile Pro Val
     50                  55                  60

Glu Ile Cys Gly His Lys Ala Ile Gly Thr Val Leu Val Gly Pro Thr
 65                  70                  75                  80

Pro Val Asn Ile Ile Gly Arg Asn Leu Leu Thr Gln Ile Gly Cys Thr
                 85                  90                  95

Leu Asn Phe


<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<223> OTHER INFORMATION: Xaa is norleucine

<400> SEQUENCE: 41

Lys Ala Arg Val Xaa
  1               5
```